(12) United States Patent
Golub et al.

(10) Patent No.: US 11,564,832 B2
(45) Date of Patent: Jan. 31, 2023

(54) DEVICE AND METHODS FOR FLOW CONTROL OF OPHTHALMIC FORMULATIONS

(71) Applicant: TearClear Corp., Copley, OH (US)

(72) Inventors: Howard L. Golub, Copley, OH (US); Srini Venkatesh, Copley, OH (US); Edward Browka, Morrisville, NC (US); Joe Ranalletta, Morrisville, NC (US); Eli Nichols, Morrisville, NC (US); Peter Smith, Morrisville, NC (US); Theodore Mosler, Morrisville, NC (US); Kristin Benokraitis, Morrisville, NC (US)

(73) Assignee: TearClear Corp., Copley, OH (US)

( * ) Notice: Subject to any disclaimer, the term of this patent is extended or adjusted under 35 U.S.C. 154(b) by 0 days.

(21) Appl. No.: 16/833,368

(22) Filed: Mar. 27, 2020

(65) Prior Publication Data

US 2020/0337895 A1    Oct. 29, 2020

Related U.S. Application Data

(60) Provisional application No. 62/993,418, filed on Mar. 23, 2020, provisional application No. 62/825,176, filed on Mar. 28, 2019.

(51) Int. Cl.
*A61F 9/00* (2006.01)

(52) U.S. Cl.
CPC ................. *A61F 9/0008* (2013.01)

(58) Field of Classification Search
CPC ........ A61F 9/0008; B65D 47/20; B65D 47/18
See application file for complete search history.

(56) References Cited

U.S. PATENT DOCUMENTS

| 4,925,017 A | 5/1990 | Jessen |
| 4,934,402 A | 6/1990 | Tarnay et al. |

(Continued)

FOREIGN PATENT DOCUMENTS

| EP | 0439999 A1 | 8/1991 |
| EP | 0631770 A1 | 1/1995 |

(Continued)

OTHER PUBLICATIONS

Baudouin, et al. Short term comparative study of topical 2% carteolol with and without benzalkonium chloride in healthy volunteers. Br J Ophthalmol. Jan. 1998; 82(1): 39-42.

(Continued)

*Primary Examiner* — Benjamin J Klein
*Assistant Examiner* — Hans Kaliher
(74) *Attorney, Agent, or Firm* — Wilson Sonsini Goodrich & Rosati

(57) ABSTRACT

A flow control device for a compressible bottle may include a reservoir, the reservoir comprising an ophthalmic formulation disposed therein, the ophthalmic formulation comprising an ophthalmic agent and a preservative; a reservoir interface, disposed at a mouth of the reservoir, the reservoir interface comprising one or more apertures, the one or more apertures in the reservoir interface fluidically connecting an interior of the reservoir and an exterior of the reservoir; a nozzle, the nozzle comprising: an outlet and a nozzle cap, the nozzle cap comprising one or more apertures, the one or more apertures in the nozzle cap fluidically connecting the outlet and a reservoir-facing surface of the nozzle; and an axis of rotation, wherein rotation of the nozzle about the axis of rotation relative to the reservoir aligns the one or more apertures in the reservoir interface with the one or more apertures in the nozzle cap.

26 Claims, 24 Drawing Sheets

(56) References Cited

U.S. PATENT DOCUMENTS

| | | | |
|---|---|---|---|
| 5,056,689 A | | 10/1991 | Heyl et al. |
| 5,154,325 A | | 10/1992 | Ryder et al. |
| 5,249,712 A | * | 10/1993 | Lontrade ............... B65D 51/24 222/189.08 |
| 5,499,751 A | | 3/1996 | Meyer |
| 5,588,559 A | | 12/1996 | Vallet et al. |
| 5,681,463 A | | 10/1997 | Shimizu et al. |
| 5,730,322 A | | 3/1998 | Iba et al. |
| 6,478,788 B1 | * | 11/2002 | Aneas .................... A61J 1/2089 604/86 |
| 10,123,904 B2 | | 11/2018 | Chauhan et al. |
| 11,045,390 B2 | | 6/2021 | Golub et al. |
| 2004/0074925 A1 | | 4/2004 | Faurie |
| 2006/0192164 A1 | * | 8/2006 | Korogi ............... A61B 5/15003 251/149 |
| 2006/0243696 A1 | | 11/2006 | Spada et al. |
| 2009/0236445 A1 | | 9/2009 | Lintern et al. |
| 2012/0305599 A1 | * | 12/2012 | Painchaud .......... B05B 11/0064 222/189.06 |
| 2015/0043958 A1 | * | 2/2015 | Painchaud .............. B05B 15/52 401/262 |
| 2017/0144178 A1 | * | 5/2017 | Deng ..................... B65D 47/20 |
| 2017/0224531 A1 | | 8/2017 | Chauhan et al. |
| 2018/0346208 A1 | * | 12/2018 | Painchaud ........... B65D 51/228 |
| 2019/0269575 A1 | * | 9/2019 | Chauhan ............... A61J 1/1475 |
| 2019/0307641 A1 | * | 10/2019 | Golub .................... B05B 15/40 |
| 2021/0267846 A1 | | 9/2021 | Golub et al. |

FOREIGN PATENT DOCUMENTS

| | | |
|---|---|---|
| GB | 2021429 B | 8/1982 |
| WO | WO-2016025560 A1 | 2/2016 |
| WO | WO-2018102817 A1 | 6/2018 |
| WO | WO-2019060846 A1 | 3/2019 |
| WO | WO-2019195734 A1 | 10/2019 |
| WO | WO-2020198655 A1 | 10/2020 |

OTHER PUBLICATIONS

Ishibashi, et al. Comparison of the short-term effects on the human corneal surface of topical timolol maleate with and without benzalkonium chloride. J Glaucoma. Dec. 2003;12(6):486-90.

Jaenen, et al. Ocular symptoms and signs with preserved and preservative-free glaucoma medications. Eur J Ophthalmol. May-Jun. 2007;17(3):341-9.

Nuzzi, et al. Conjunctiva and subconjunctival tissue in primary open-angle glaucoma after long-term topical treatment: an immunohistochemical and ultrastructural study. Graefes Arch Clin Exp Ophthalmol. Mar. 1995;233(3):154-62.

PCT/US2019/026070 International Search Report and Written Opinion dated Aug. 1, 2019.

PCT/US2019/20670 Invitation to Pay Additional Fees dated Jun. 7, 2019.

Rolando, et al. The Effect of Different Benzalkonium Chloride Concentrations on Human Normal Ocular Surface. The Lacrimal System. Kugler and Ghedini, New York 1991, 87-91.

U.S. Appl. No. 16/376,387 Final Office Action dated Apr. 27, 2020.

U.S. Appl. No. 16/376,387 First Action Interview Summary dated Nov. 26, 2019.

Aug. 13, 2019 Restriction Requirement U.S. Appl. No. 16/376,387, 5 pages.

Sep. 17, 2019 First Action Interview Pilot Program Pre-Interview Communication U.S. Appl. No. 16/376,387, 4 pages.

Extended European Search Report dated Nov. 24, 2021 for European Application No. 19780970.0.

PCT/US2019/026070 International Preliminary Report on Patentability dated Oct. 6, 2020.

PCT/US2020/025412 International Preliminary Report on Patentability dated Sep. 28, 2021.

PCT/US2020/025412 International Search Report and Written Opinion dated Aug. 12, 2020.

U.S. Appl. No. 16/376,387 Restriction Requirement dated Aug. 13, 2019.

* cited by examiner

DEVICE AND METHODS FOR FLOW CONTROL OF OPHTHALMIC FORMULATIONS

CROSS-REFERENCE

This application claims the benefit of U.S. Provisional Application No. 62/825,176, filed Mar. 28, 2019, and U.S. Provisional Application No. 62/993,418, filed Mar. 23, 2020, each of which are incorporated herein by reference in their entireties.

BACKGROUND

The present disclosure generally relates to systems and methods for removal of preservatives and removing a preservative from a fluid comprising a therapeutic agent.

Other approaches to removing a preservative from a fluid comprising a therapeutic agent to an eye may be less than ideal in at least some respects. Patients suffering from chronic diseases may use daily eye drop instillations, for example for the treatment of glaucoma. In order to prevent bacterial growth, commercially available eye drop formulations typically use a preservative, in order to address possible bacterial contamination.

Although preservative removal devices have been proposed, the such approaches can be less than ideal and overly complex in at least some instances. For example, the concentration of a preservative may not be stable over repeated use.

SUMMARY

The present disclosure relates to apparatuses and methods for removing a preservative from a fluid comprising a therapeutic agent. These apparatuses and methods provide various advantages and improvements for removing a preservative from a fluid comprising a therapeutic agent compared to other approaches. For example, preservative removal devices may be overly complex and inadvertently reduce the concentration of the preservative within the formulation in the reservoir and/or remove the therapeutic agent during administration. Therefore, disclosed herein are apparatuses and methods that provide a technical solution to address at least some of the above drawbacks of other approaches and reduce preservatives in eye drops while substantially retaining the therapeutic agent.

The apparatuses can be configured in many ways and may comprise a nozzle configured to deliver the therapeutic agent to an eye with a nozzle. The presently disclosed methods and apparatuses can reduce preservatives in eye drops while substantially retaining the therapeutic agent with very little change in the concentration of a preservative in the bottle. This can be achieved with a nozzle that fits on the end of a squeeze bottle that controls the flow eye drops to a patient. Although reference is made to the treatment of eyes with nozzles coupled to containers, the methods and apparatuses disclosed herein can be configured in many ways to deliver therapeutic agents to many locations of the body, such as with implantable devices, syringes coupled to needles and intravenous drug delivery.

In an aspect, a flow control device for a compressible bottle is provided. The flow control device may comprise: a reservoir, the reservoir comprising an ophthalmic formulation disposed therein, the ophthalmic formulation comprising an ophthalmic agent and a preservative; a reservoir interface, disposed at a mouth of the reservoir, the reservoir interface comprising one or more apertures, the one or more apertures in the reservoir interface fluidically connecting an interior of the reservoir and an exterior of the reservoir; a nozzle, the nozzle comprising: an outlet and a nozzle cap, the nozzle cap comprising one or more apertures, the one or more apertures in the nozzle cap fluidically connecting the outlet and a reservoir-facing surface of the nozzle; and an axis of rotation, wherein rotation of the nozzle about the axis of rotation relative to the reservoir aligns the one or more apertures in the reservoir interface with the one or more apertures in the nozzle cap.

In some embodiments, the flow control device further comprises a polymeric matrix disposed in an interior volume of the nozzle, the polymeric matrix comprising absorbed molecules of the preservative from the ophthalmic formulation. In some embodiments, rotation of the reservoir interface prevents flow of the ophthalmic formulation between the interior of the nozzle and the reservoir, thereby stabilizing a concentration of the preservative in the ophthalmic formulation. In some embodiments, the flow control device further comprises a bottle cap, wherein rotation of the bottle cap about the axis of rotation relative to the reservoir rotates the nozzle about the axis of rotation relative to the reservoir. In some embodiments, the nozzle comprises a first one or more ridges on a bottle-cap facing surface, the first one or more ridges receivable by the bottle cap. In some embodiments, the bottle cap comprises one or more alignment channels on an interior surface of the bottle cap, the first one or more ridges on the bottle-cap facing surface of the nozzle cap received within the one or more alignment channels. In some embodiments, the nozzle comprises a second one or more ridges on a reservoir facing surface, the second one or more ridges receivable by the reservoir. In some embodiments, the reservoir comprises one or more rotation guides, the second one or more ridges on a reservoir facing surface received by the one or more rotation guides. In some embodiments, the second one or more ridges on the bottle-facing surface received by the rotation guides limits an angle of rotation of the nozzle relative to the reservoir. In some embodiments, the bottle cap comprises a screw cap.

In some embodiments, the reservoir interface further comprises one or more alignment tabs and wherein the mouth of the reservoir comprises one or more alignment channels, wherein the one or more alignment tabs are received within the one or more alignment channels thereby rotationally fixing an orientation of the reservoir interface relative to the reservoir. In some embodiments, the nozzle cap is rotationally fixed relative to the nozzle. In some embodiments, the flow control device further comprises a filter disposed within the nozzle. In some embodiments, the polymeric matrix comprises poly hydroxyl ethyl methacrylate (pHEMA), poly hydroxyl ethyl methacrylate-co-methacrylic acid, or a combination thereof. In some embodiments, the polymeric matrix comprises at least one monomer selected from the group consisting of hydroxyethyl methacrylate (HEMA), methacrylic acid (MAA), N-vinyl-pyrrolidone (NVP), dimethylacrylamide (DMA), t-butyl methacrylate (TBM), and Methacryloxypropyltris(trimethylsiloxy)silane (TRIS). In some embodiments, the ophthalmic agent comprises at least one of Timolol Maleate, Levofloxacin, Dorzolamide, Brimonidine Tartrate, Bimatoprost, Tetrahydrozolin, or Olopatadine. In some embodiments, the ophthalmic agent comprises Timolol Maleate and Brimonidine Tartrate. In some embodiments, the preservative comprises at least one of benzalkonium chloride, SofZia, or Purite. In some embodiments, the reservoir comprises less than 100 milliliters of an ophthalmic formulation.

In another aspect, the present disclosure provides a method of controlling a preservative concentration within an ophthalmic formulation. The method may comprise: receiving the bottle of any aspect or embodiment herein and rotating the nozzle or the bottle cap relative to the reservoir.

In another aspect, the present disclosure provides a method of fabricating the flow control device of any aspect or embodiment herein. The method may comprise: filling the reservoir with the ophthalmic formulation; placing the reservoir interface on the reservoir; placing the nozzle cap on the nozzle; and placing the nozzle at the mouth of the reservoir. In some embodiments, the method further comprises placing a bottle cap on the nozzle.

In another aspect a kit comprising the flow control device of any aspect or embodiment herein and a packaging is provided. In some embodiments, the kit further comprises a label, wherein the label comprises an indication of a contents of the ophthalmic formulation disposed within the reservoir.

In another aspect, the present disclosure provides a flow control device for delivering an ophthalmic formulation. The device may comprise: a reservoir, the reservoir comprising the ophthalmic formulation disposed therein, the ophthalmic formulation comprising an ophthalmic agent and a preservative; a nozzle, the nozzle comprising: an outlet, an interior volume comprising a preservative removing device, and one or more nozzle apertures fluidically connecting the interior volume with an exterior of the nozzle; and a reservoir interface comprising one or more reservoir apertures, wherein upon rotation or translation of the nozzle relative to the reservoir interface, the one or more nozzle apertures are fluidically connected with the one or more reservoir apertures.

In some embodiments, the preservative removing device comprises a polymeric matrix comprising absorbed molecules of the preservative from the ophthalmic formulation. In some embodiments, upon rotation or translation of the nozzle, the one or more nozzle apertures are fluidically disconnected from the one or more reservoir apertures, thereby preventing flow of the ophthalmic formulation between the interior volume of the nozzle and the reservoir and stabilizing a concentration of the preservative in the ophthalmic formulation.

In some embodiments, the device further comprises a bottle cap, wherein rotation of the bottle cap relative to the reservoir rotates or translates the nozzle relative to the reservoir interface. In some embodiments, the bottle cap produces an audible or tactile click when moved into a closed state. In some embodiments, the bottle cap comprises a closure assembly which is resistant to manipulation from a child.

In some embodiments, the nozzle comprises an outlet filter adjacent the outlet. In some embodiments, the outlet filter comprises a mesh or a screen. In some embodiments, the nozzle comprises an inlet filter adjacent the one or more nozzle apertures. In some embodiments, the inlet filter comprises a mesh or a screen.

In some embodiments, the device further comprises a bottle cap, wherein one or more nozzle apertures are aligned with the one or more reservoir apertures when the bottle cap is removed and wherein one or more nozzle apertures are not aligned with the one or more reservoir apertures when the bottle cap is coupled to the nozzle. In some embodiments, the bottle cap is removed, the nozzle is in an aligned rotational position. In some embodiments, rotation of the bottle cap about the axis of rotation relative to the reservoir rotates the nozzle about an axis of rotation relative to the reservoir. In some embodiments, the nozzle comprises a first one or more ridges on a bottle-cap facing surface, the first one or more ridges receivable by the bottle cap. In some embodiments, the bottle cap comprises one or more alignment channels on an interior surface of the bottle cap, the first one or more ridges on the bottle-cap facing surface of the nozzle received within the one or more alignment channels.

In some embodiments, the nozzle comprises a second one or more ridges on a reservoir interface facing surface, the second one or more ridges receivable by the reservoir interface. In some embodiments, the reservoir interface comprises one or more rotation guides, the second one or more ridges on a reservoir interface facing surface received by the one or more rotation guides. In some embodiments, the second one or more ridges on the reservoir interface facing surface received by the one or more rotation guides limits an angle of rotation of the nozzle relative to the reservoir interface.

In some embodiments, the bottle cap is removed, the nozzle is in an aligned translational position. In some embodiments, a spring is disposed between the nozzle and the reservoir interface and wherein a restoring force of the spring translates the nozzle to the aligned translational position when the bottle cap is removed. In some embodiments, when the bottle cap is in a closed state, the nozzle is not in the aligned position. In some embodiments, when the bottle cap is in a closed state, the spring is at least partially compressed.

In some embodiments, the device further comprises a translation stop. In some embodiments, the translation stop comprises a plug configured to seal the one or more nozzle apertures. In some embodiments, the translation stop comprises a rotation stop for the bottle cap.

In some embodiments, the nozzle comprises a housing configured to contain the preservative removing device, wherein the housing is translated in relation to an exterior surface of the reservoir interface. In some embodiments, a gasket provides a fluidic seal between the reservoir interface and the nozzle. In some embodiments, an interference fit provides a fluidic seal between the reservoir interface and the nozzle.

In another aspect, the present disclosure provides a flow control device for delivering an ophthalmic formulation. The device may comprise: a reservoir, the reservoir comprising an ophthalmic formulation disposed therein, the ophthalmic formulation comprising an ophthalmic agent and a preservative; a reservoir interface, disposed at a mouth of the reservoir, the reservoir interface comprising one or more apertures, the one or more apertures in the reservoir interface fluidically connecting an interior of the reservoir and an exterior of the reservoir; a nozzle, the nozzle comprising: an outlet and a nozzle seal, the nozzle seal comprising one or more apertures, the one or more apertures in the nozzle cap fluidically connecting the outlet and a surface of the nozzle oriented toward the reservoir interface; and an axis of rotation, wherein rotation of the nozzle about the axis of rotation relative to the reservoir aligns the one or more apertures in the reservoir interface with the one or more apertures in the nozzle seal.

In some embodiments, the device comprises a polymeric matrix disposed in an interior volume of the nozzle, the polymeric matrix comprising absorbed molecules of the preservative from the ophthalmic formulation. In some embodiments, rotation of the nozzle prevents flow of the ophthalmic formulation between the interior of the nozzle and the reservoir, thereby stabilizing a concentration of the preservative in the ophthalmic formulation.

In some embodiments, the device further comprises a bottle cap, wherein rotation of the bottle cap about the axis of rotation relative to the reservoir rotates the nozzle about the axis of rotation relative to the reservoir. In some embodiments, the nozzle comprises a first one or more ridges on a bottle-cap facing surface, the first one or more ridges receivable by the bottle cap. In some embodiments, the bottle cap comprises one or more alignment channels on an interior surface of the bottle cap, the first one or more ridges on the bottle-cap facing surface of the nozzle seal received within the one or more alignment channels.

In some embodiments, the nozzle comprises a second one or more ridges on a reservoir facing surface, the second one or more ridges receivable by the reservoir. In some embodiments, the reservoir comprises one or more rotation guides, the second one or more ridges on a reservoir facing surface received by the one or more rotation guides. In some embodiments, the second one or more ridges on the bottle-facing surface received by the rotation guides limits an angle of rotation of the nozzle relative to the reservoir.

In some embodiments, the bottle cap comprises a screw cap. In some embodiments, the reservoir interface further comprises one or more alignment tabs and wherein the mouth of the reservoir comprises one or more alignment channels, wherein the one or more alignment tabs are received within the one or more alignment channels thereby rotationally fixing an orientation of the reservoir interface relative to the reservoir. In some embodiments, the nozzle seal is rotationally fixed relative to the nozzle. In some embodiments, the device further comprises a filter disposed within the nozzle.

In some embodiments, the polymeric matrix comprises poly hydroxyl ethyl methacrylate (pHEMA), poly hydroxyl ethyl methacrylate-co-methacrylic acid, or a combination thereof. In some embodiments, the polymeric matrix comprises at least one monomer selected from the group consisting of hydroxyethyl methacrylate (HEMA), methacrylic acid (MAA), N-vinyl-pyrrolidone (NVP), dimethylacrylamide (DMA), t-butyl methacrylate (TBM), and Methacryloxypropyltris(trimethylsiloxy)silane (TRIS). In some embodiments, the ophthalmic agent comprises at least one of Timolol Maleate, Levofloxacin, Dorzolamide, Brimonidine Tartrate, Bimatoprost, Tetrahydrozolin, or Olopatadine. In some embodiments, the ophthalmic agent comprises Timolol Maleate and Brimonidine Tartrate. In some embodiments, the preservative comprises at least one of benzalkonium chloride, SofZia, or Purite. In some embodiments, the reservoir comprises less than 100 milliliters of an ophthalmic formulation.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
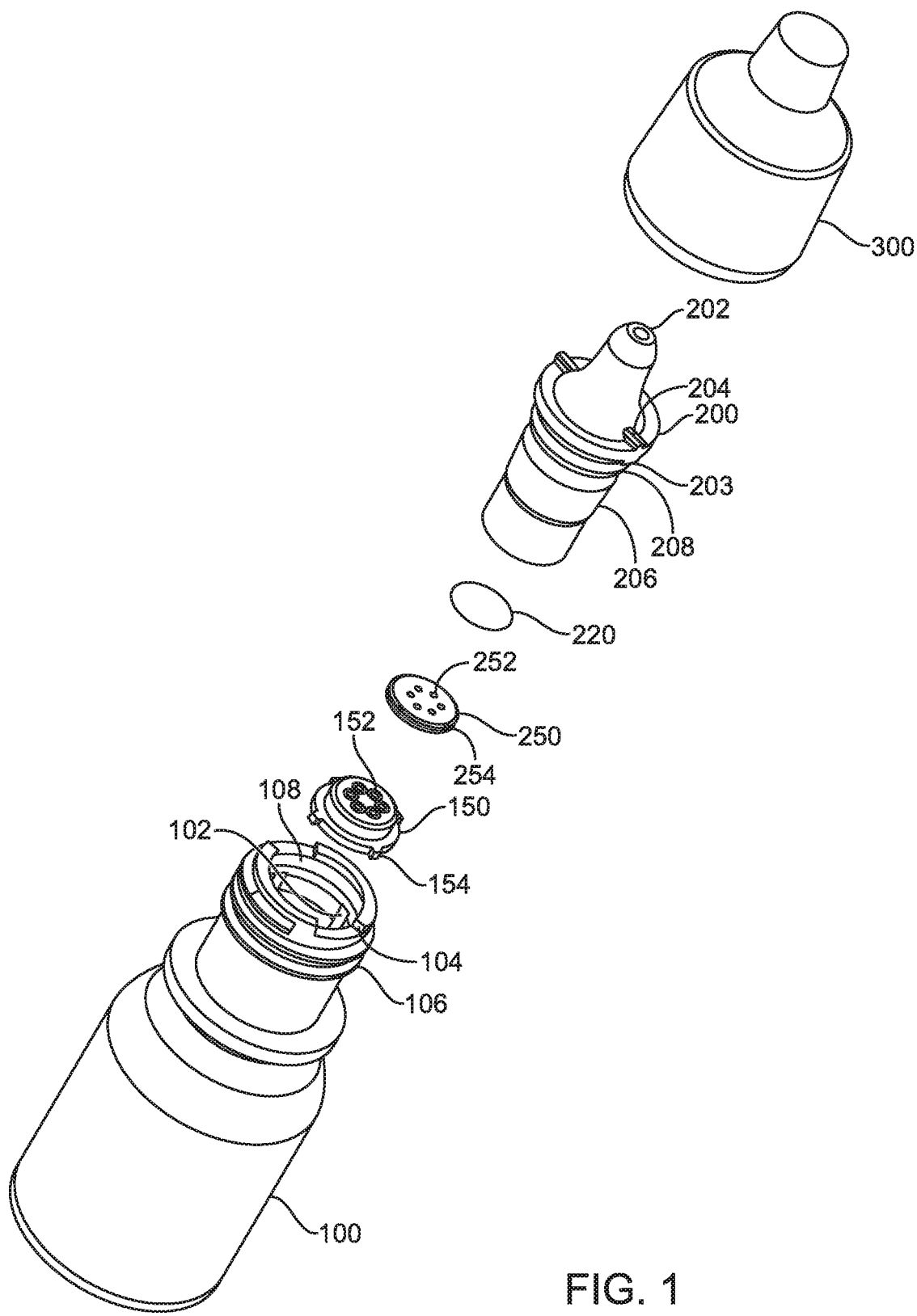
FIG. 1 illustrates an exploded view of a flow control device, in accordance with some embodiments.

Unless defined otherwise, all technical and scientific terms used herein have the same meaning as is commonly understood by one of skill in the art to which this invention belongs. All patents and publications referred to herein are incorporated by reference.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm, or 0.1 mm of a given value or range.

As used herein, the terms "comprises," "comprising," or any other variation thereof, are intended to cover a nonexclusive inclusion, such that a process, method, article, or apparatus that comprises a list of elements does not include only those elements but may include other elements not expressly listed or inherent to such process, method, article, or apparatus.

As used herein, the terms "user", "subject" or "patient" are used interchangeably. As used herein, the terms "subject" and "subjects" refers to an animal (e.g., birds, reptiles, and mammals), a mammal including a primate (e.g., a monkey, chimpanzee, and a human) and a non-primate (e.g., a camel, donkey, zebra, cow, pig, horse, cat, dog, rat, and mouse). In certain embodiments, the mammal is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85years old, 85 to 90 years old, 90 to 95 years old or 95 to 100. In some embodiments, the subject or patient is a pig. In certain embodiments, the pig is 0 to 6 months old, 6 to 12 months old, 1 to 5 years old, 5 to 10 years old or 10 to 15 years old. The natural lifespan of a pig is 10-15 years.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms may be based on objective or subjective parameters; including the results of a physical examination, neuropsychiatric exams, and/or a psychiatric evaluation. The term "treating" and conjugations thereof, include prevention of an injury, pathology, condition, or disease.

In some embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction of" a symptom or symptoms (and grammatical equivalents of this phrase) means decreasing of the severity or frequency of the symptom(s), or elimination of the symptom(s). The exact amounts may depend on the purpose of the treatment and may be ascertainable by one skilled in the art using known techniques.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Aspects of the present disclosure relate to systems, methods, devices, and kits for controlling the flow of an ophthalmic formulation through a delivery device. Aspects of the present disclosure may reduce, prevent, or eliminate instability in the concentration of a preservative within an ophthalmic formulation over time. Aspects of the present disclosure may comprise or may be used in connection with a compressible bottle, such as an eye drop bottle.

Disclosed herein is a flow control device for delivering an ophthalmic formulation. A device may comprise a reservoir. The reservoir may comprise an ophthalmic formulation disposed with the reservoir. The ophthalmic formulation may comprise an ophthalmic agent and a preservative. The flow control device may comprise a nozzle. The nozzle may comprise an outlet. The nozzle may comprise an interior volume comprising a preservative removing device. The nozzle may comprise one or more nozzle apertures fluidically connecting the interior volume with an exterior of the nozzle. The device may comprise a reservoir interface. The reservoir interface may comprise one or more reservoir apertures. Upon rotation or translation of the nozzle relative to the reservoir interface, the one or more nozzle apertures may be fluidically connected with the one or more reservoir apertures.

FIG. 1 illustrates an exploded view of an example flow control device, in accordance with some embodiments. Other views and components of the example flow control device of FIG. 1 are illustrated in FIG. 2, FIG. 3A, FIG. 3B, FIG. 4A, FIG. 4B, FIG. 5A, FIG. 5B, FIG. 6A, FIG. 6B, FIG. 7A, FIG. 7B, FIG. 8A, FIG. 8B, FIG. 9A, and FIG. 9B. FIG. 10 illustrates a partially exploded view of another example flow control device, in accordance with some embodiments. Other views and components of the example flow control device of FIG. 10 are illustrated in FIG. 11, FIG. 12, FIG. 13A, and FIG. 13B. FIG. 14 illustrates an exploded view of another example flow control device, in accordance with some embodiments. Other views and components of the example flow control device of FIG. 14 are illustrated in FIG. 15A, FIG. 15B, FIG. 16A, FIG. 16B, FIG. 17A, FIG. 17B, FIG. 18A, FIG. 18B, FIG. 19A, FIG. 19B, FIG. 20, FIG. 21, FIG. 22A, FIG. 22B, FIG. 22C, FIG. 23A, FIG. 23B, and FIG. 23C. FIG. 24A and FIG. 24B illustrate view section views of another example flow control device, in accordance with some embodiments.

Except where context would conflict, the various parts of the flow control devices of the present disclosure may be made of various materials such as plastics, metals, glasses, etc. The plastic parts may include one or a combination of various polyolefins, polypropylenes, polyethylenes, etc. The parts may be molded, machined, extruded, 3D printed, cast, vacuum formed, etc. and as appropriate for the type of plastic. Alignment features, tabs, ridges, and spring elements may be optionally reinforced with polycarbonate, as needed, for example as reinforcement.

Devices, systems, and methods of the present disclosure may be combined with various geometries of flow diverters, for example, as disclosed in International Publication No. WO2019/195734, which is incorporated herein by reference. For example, the interior volumes of the nozzles as disclosed herein may comprise an example of a flow diverter of WO2019/195734 disposed within the volume.

FIG. 1 illustrates an exploded view of an example flow control device, in accordance with some embodiments. The flow control device may comprise a reservoir 100. The reservoir may comprise an ophthalmic formulation disposed therein. The ophthalmic formulation may comprise an ophthalmic agent and a preservative, as described elsewhere herein for example in the sections "Ophthalmic Agent" and "Preservative". The ophthalmic formulation may comprise any of the example formulations disclosed herein, for example in the section "Solution, Emulsion, or Suspension". Reservoir 100 may comprise a compressible bottle, for example the reservoir of a commercial eyedrop bottle. In some cases, reservoir 100 may utilize a commonly available commercial bottle. In other cases, reservoir 100 may be a proprietary bottle designed for a specific application, such as the systems, methods, devices, and kits disclosed herein.

A reservoir of the present disclosure may comprise an interior volume which may contain an ophthalmic formulation as disclosed herein. A reservoir may comprise an interior volume of about 2.5 cc. A reservoir may comprise an interior volume of about 8 cc. A reservoir may comprise an interior volume of at least about 0.2 cubic centimeters (cc), at least about 0.5 cc, at least about 1 cc, at least about 1.5 cc, at least about 2 cc, at least about 2.5 cc, at least about 3 cc, at least about 4 cc, at least about 5 cc, at least about 6 cc, at least about 7 cc, at least about 8 cc, at least about 10 cc, or more. A reservoir may comprise an interior volume between about 0.1 cc and about 10 cc, between about 1 cc and about 10 cc, between about 2 cc and about 10 cc, between about 2.5 cc and about 10 cc, etc. For example, an 8 cc bottle may dispense about 5 cc of an ophthalmic formulation. For example, a 2.5 cc about, may dispense about 2 cc of an ophthalmic formulation.

In some cases, an ophthalmic formulation may at least partially fill an interior volume of a reservoir. An ophthalmic formulation may fill at least about 1%, at least about 2%, at least about 5%, at least about 10%, at least about 20%, at least about 50%, at least about 70%, at least about 80%, at least about 90%, at least about 95%, or more of an interior volume of the reservoir. An ophthalmic formulation may fill between about 1% and about 99%, about 10% and about 98%, about 25% and about 50%, about 10% and about 50%, etc. of an interior volume of the reservoir.

A reservoir of the present disclosure may be made of a plastic. A plastic may be compressible. A plastic may comprise one or a combination of various polyolefins, polypropylenes, polyethylenes, etc. A reservoir may comprise a low-density polyethylene (e.g. Nalgene™). A reservoir may comprise a reservoir of a compressible bottle. The bottle may be made of a material which is sufficiently flexible for a person to at least partially collapse the sides of the reservoir, thereby increasing a pressure within the reservoir. Reservoir 100 may comprise threads 106.

The flow control device may comprise a reservoir interface 150, disposed at a mouth 108 of the reservoir. The reservoir interface may comprise one or more apertures 152. The one or more apertures in the reservoir interface may fluidically connect an interior of the reservoir with an exterior of the reservoir. The one or more aperture may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

As illustrated in FIG. 1, the reservoir interface 150 may comprises one or more alignment tabs 154. The mouth 108 of the reservoir may comprises one or more alignment channels 102 which may receive the one or more alignment tabs. When the alignment tabs are received within the one or more alignment channels an orientation of the reservoir interface relative to the reservoir may be rotationally fixed.

The flow control device may comprise a nozzle 200. The nozzle may comprise at least one outlet 202 and a nozzle cap 250. The nozzle may comprise an interior volume, which interior volume may comprise a preservative removing device. A preservative removing device may comprise any example of a preservative removing device as disclosed herein, for example, the preservative removal agent and matrices as disclosed in the section "Preservative Removal Agent" elsewhere herein. A nozzle may comprise an interior volume of about 0.5 cc. A nozzle may comprise an interior volume of about 0.1 cc. A nozzle may comprise an interior volume of about 1 cc. A nozzle may comprise an interior volume of at least about 0.05 cubic centimeters (cc), at least about 0.1 cc, at least about 0.2 cc, at least about 0.3 cc, at least about 0.4 cc, at least about 0.5 cc, at least about 0.6 cc, at least about 0.7 cc, at least about 0.8 cc, at least about 1 cc, at least about 1.5 cc, at least about 2 cc, at least about 5 cc, or more. A reservoir may comprise an interior volume between about 0.01 cc and about 5 cc, between about 0.1 cc and about 5 cc, between about 0.5 cc and about 1.5 cc, between about 0.5 cc and about 5 cc, etc.

In some cases, a preservative removing device may at least partially fill an interior volume of a nozzle. For example, a preservative removing device may comprise a polymeric matrix. A preservative removing device may fill at least about 1%, at least about 2%, at least about 5%, at least about 10%, at least about 20%, at least about 50%, at least about 70%, at least about 80%, at least about 90%, at least about 95%, or more of an interior volume of the nozzle. A preservative removing device may fill between about 1% and about 99%, about 10% and about 98%, about 25% and about 50%, about 10% and about 50%, etc. of an interior volume of the nozzle.

The nozzle 200 may comprise and outlet 202. The outlet may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The outlet may comprise an aperture diameter of between about 10 and about 5000 microns, between about 10 and about 2500 microns, between about 10 and about 1000 microns, between about 10 and about 500 microns, etc.

The nozzle cap 250 may comprise one or more apertures 252. The one or more apertures in the nozzle cap may fluidically connect the outlet 202 and an exterior of the nozzle. The one or more apertures in the nozzle cap may fluidically connect to a reservoir-facing surface of the nozzle. The one or more aperture may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

In some cases, the nozzle cap 250 is rotationally fixed relative to the nozzle 200. In some cases, the nozzle cap is rotationally fixed relative to the nozzle by one or more retention features 254. The retention features 254 may comprise a snap fit, an interference fit, a press fit, a screw, etc. Rotational fixation of the nozzle cap may be aided by a glue, a weld, a heat seal, etc. In some cases, the nozzle cap may be removable. The nozzle cap may aid in retention of a preservative removing device within an interior volume of the nozzle.

In some cases, a nozzle cap may comprise a filter 220. A filter may comprise a mesh or a screen. A filter may comprise a polyester mesh. A filter may comprise a paper mesh. A filter 220 may be disposed within nozzle cap 250. A filter may be disposed adjacent a nozzle cap 250. A filter may comprise a mesh size of about 25 microns. A filter may comprise a mesh size of at least about 1 micron, at least about 2 microns, at least about 5 microns, at least about 10 microns, at least about 20 microns, at least about 50 microns, at least about 100 microns or more. A filter may comprise a mesh size of at most about 1 mm, at most about 500 microns, at most about 250 microns, at most about 100 microns, at most about 50 microns, at most about 25 microns, or less. A filter may comprise a mesh size of between about 1 and about 50 microns, between about 10 and about 50 microns, between about 1 and about 30 microns, between about 20 and about 30 microns, etc.

In some embodiments, the nozzle 200 may comprise one or more retention features on an exterior surface of the nozzle. The retention features 206, 208 may interface with the mouth of the reservoir to retain the nozzle in the mouth of the reservoir. The retention features 206, 208 may comprise a snap fit, an interference fit, a press fit, a screw, etc. In some cases, the retention features may allow for rotation of the nozzle relative to the reservoir interface. In some cases, the nozzle may be removable. The nozzle may be removable with a nozzle cap in place.

Figure 2:
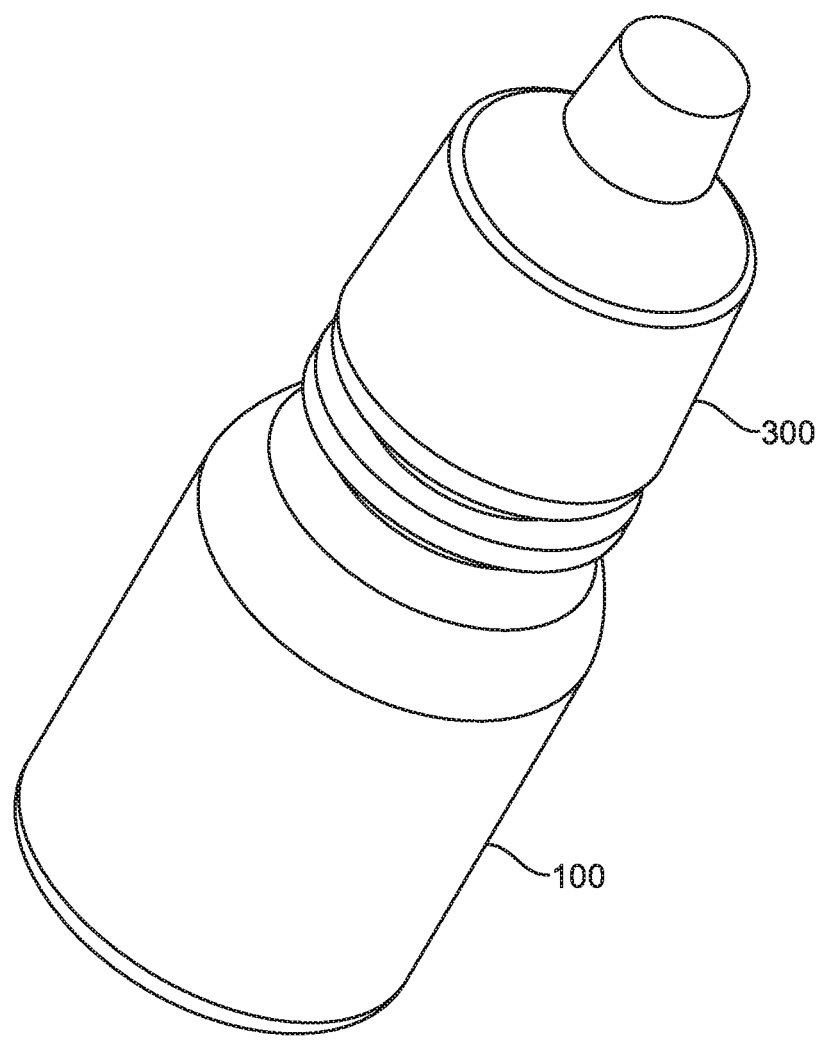
FIG. 2 illustrates an exterior view of a flow control device integrated with a compressible bottle, in accordance with some embodiments.

FIG. 2 illustrates an exterior view of a flow control device integrated with a compressible bottle, in accordance with some embodiments. FIG. 2 illustrates reservoir 100 and cap 300. As illustrated cap 300 may be screwed on or off of threads 106 of reservoir 100.

Figure 3A:
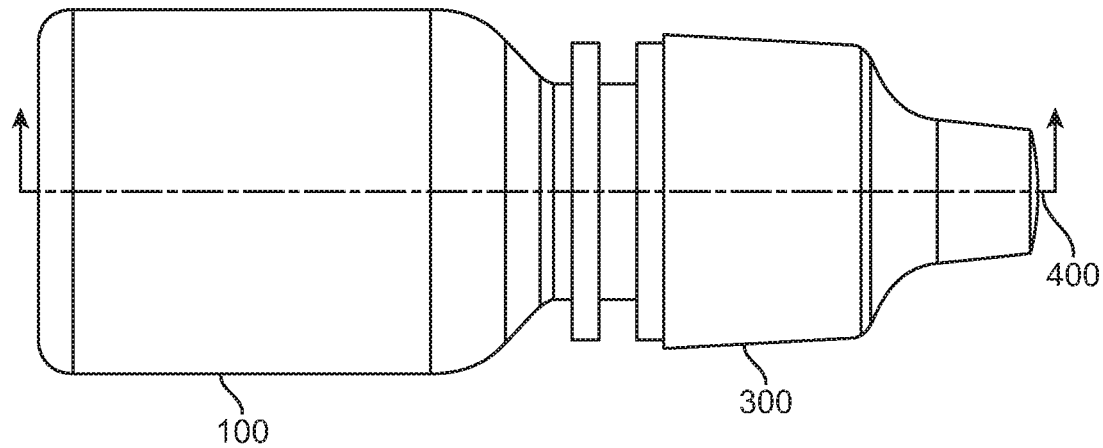
FIG. 3A and FIG. 3B illustrate an exterior view and a slice view, respectively, of a flow control device in an open position, in accordance with some embodiments.
Figure 3B:
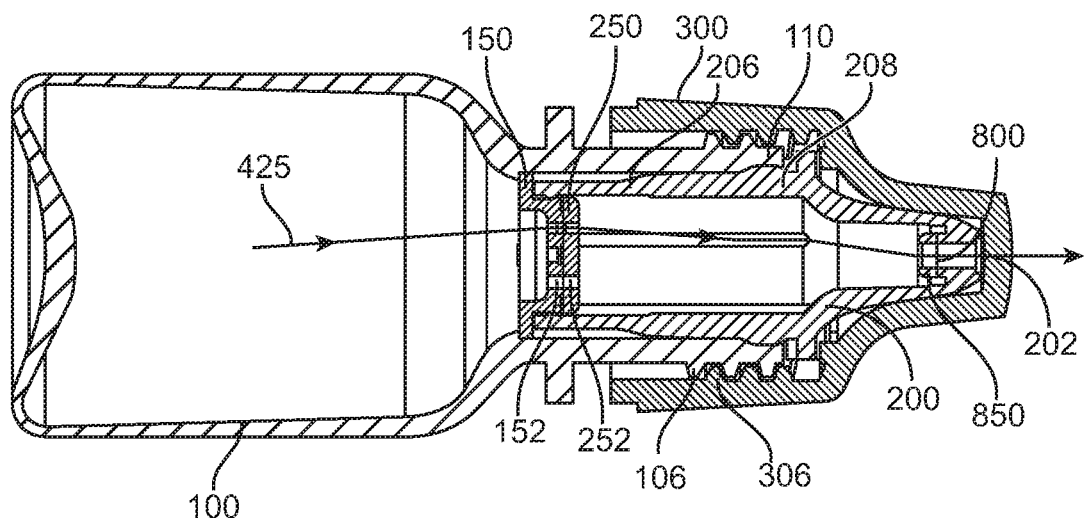
Figure 4A:
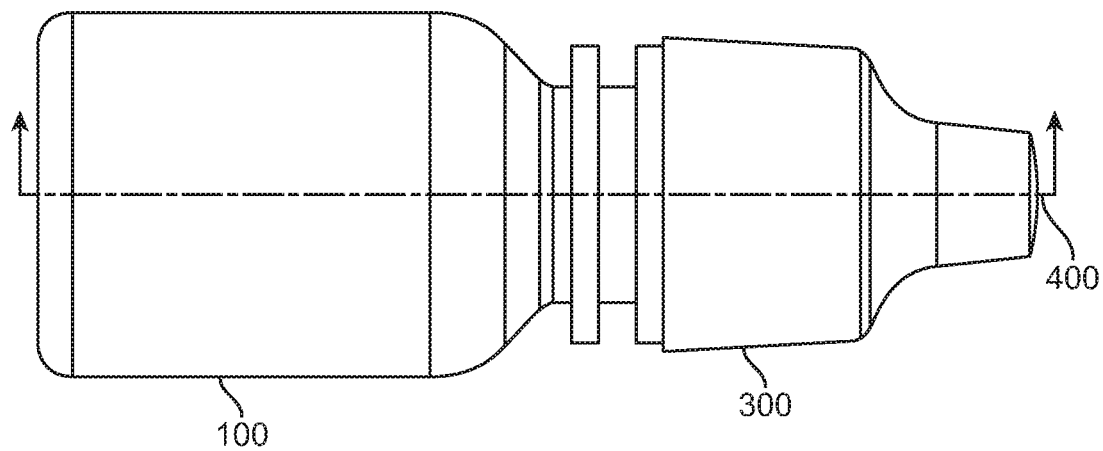
FIG. 4A and FIG. 4B illustrate an exterior view and a slice view, respectively, of a flow control device in a closed position, in accordance with some embodiments.
Figure 4B:
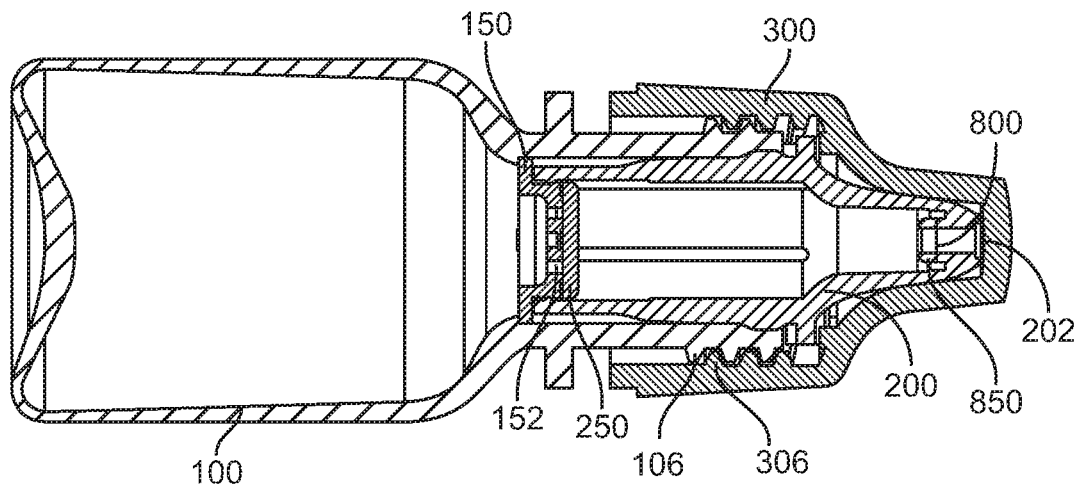

FIG. 3A and FIG. 3B illustrate an exterior view and a slice view, respectively, of a flow control device in an open position, in accordance with some embodiments. FIG. 4A and FIG. 4B illustrate an exterior view and a slice view, respectively, of a flow control device in a closed position, in accordance with some embodiments. Rotation of the nozzle may prevent flow of the ophthalmic formulation between the interior of the nozzle and the reservoir, thereby stabilizing a concentration of the preservative in the ophthalmic formulation. In some cases, the flow control device may comprise an axis of rotation 400. Rotation of the nozzle about the axis of rotation 400 relative to the reservoir may align the one or more apertures in the reservoir interface 152 with the one or more apertures in the nozzle cap 252. Looking at apertures 152 and apertures 252, in FIG. 3B, it is illustrated that both apertures are aligned allowing for fluid passage between reservoir 100 and nozzle 200. Looking at apertures 152 and nozzle cap 250, in FIG. 4B, it is illustrated that both apertures are not aligned thereby impeding fluid passage between reservoir 100 and nozzle 200. FIG. 3B illustrates flow path 425 through the device.

Also illustrated in FIG. 3B is outlet filter 800. A filter may comprise a mesh or a screen. A filter may comprise a polyester mesh. A filter may comprise a paper mesh. A filter 800 may be disposed within outlet cap 850. A filter may be disposed adjacent outlet cap 850. A filter may comprise a mesh size of about 25 microns. A filter may comprise a mesh size of at least about 1 micron, at least about 2 microns, at least about 5 microns, at least about 10 microns, at least about 20 microns, at least about 50 microns, at least about 100 microns or more. A filter may comprise a mesh size of at most about 1 mm, at most about 500 microns, at most about 250 microns, at most about 100 microns, at most about 50 microns, at most about 25 microns, or less. A filter may comprise a mesh size of between about 1 and about 50 microns, between about 10 and about 50 microns, between about 1 and about 30 microns, between about 20 and about 30 microns, etc.

Outlet filter 800 may be held in place by outlet cap 850. In some cases, the outlet cap 250 is rotationally fixed relative to the nozzle 200. In some cases, the outlet cap is rotationally fixed relative to the nozzle by one or more retention features. The retention features may comprise a snap fit, an interference fit, a press fit, a screw, etc. Rotational fixation of the outlet cap may be aided by a glue, a weld, a heat seal, etc. In some cases, the outlet cap may be removable. The outlet cap may aid in retention of a preservative removing device within an interior volume of the nozzle. In some cases, outlet cap 850 may be insert molded into a nozzle.

Also, illustrated in FIG. 3B is the interaction between retention features 206, 208 with the mouth 108 of the reservoir to retain the nozzle in the mouth of the reservoir. The retention features 206, 208 may comprise a snap fit, an interference fit, a press fit, a screw, etc. In some cases, the retention features may allow for rotation of the nozzle relative to the reservoir interface. In some cases, the nozzle may be removable. The nozzle may be removable with a nozzle cap in place. The reservoir 100 may comprise one or more retention features 110 to aid in a fit between the nozzle and a reservoir. FIG. 3B illustrates an interference fit between the reservoir 100 and nozzle 200. The seal between reservoir 100 and nozzle 200 may be water tight.

Figure 5A:
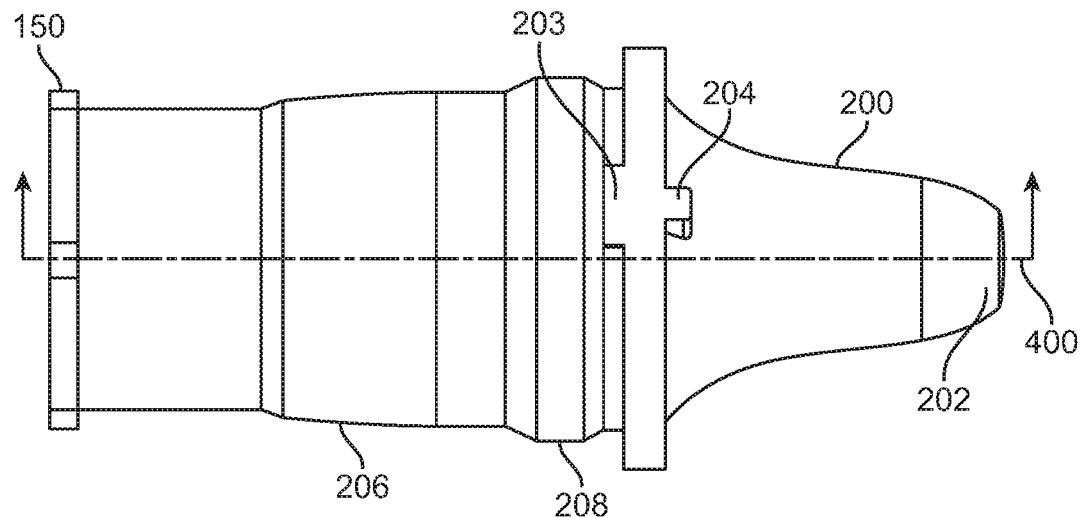
FIG. 5A and FIG. 5B illustrate an exterior view and a slice view, respectively of a nozzle and a nozzle cap in a closed position, in accordance with some embodiments.
Figure 5B:
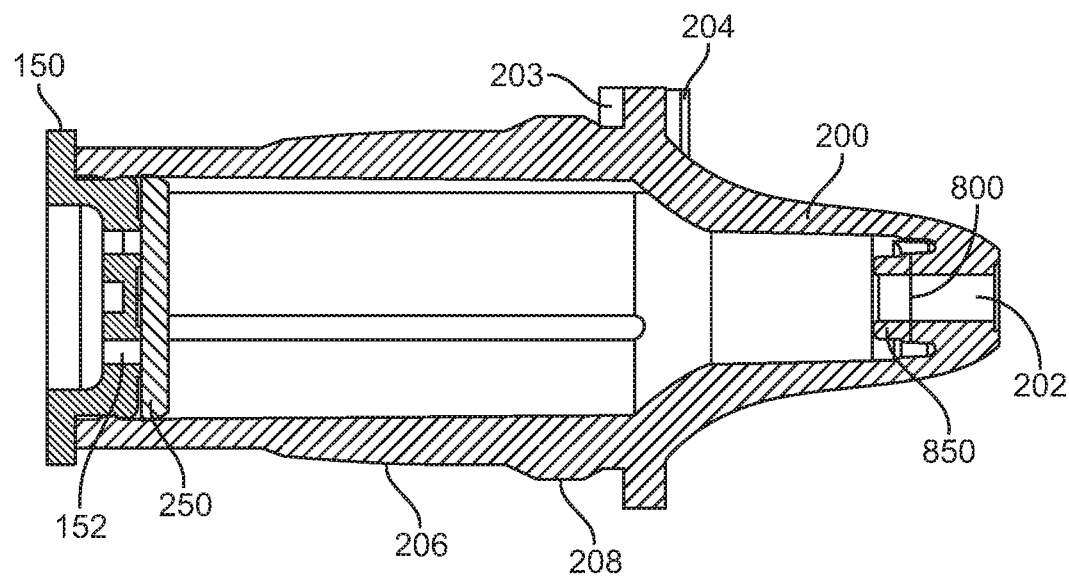
Figure 6A:
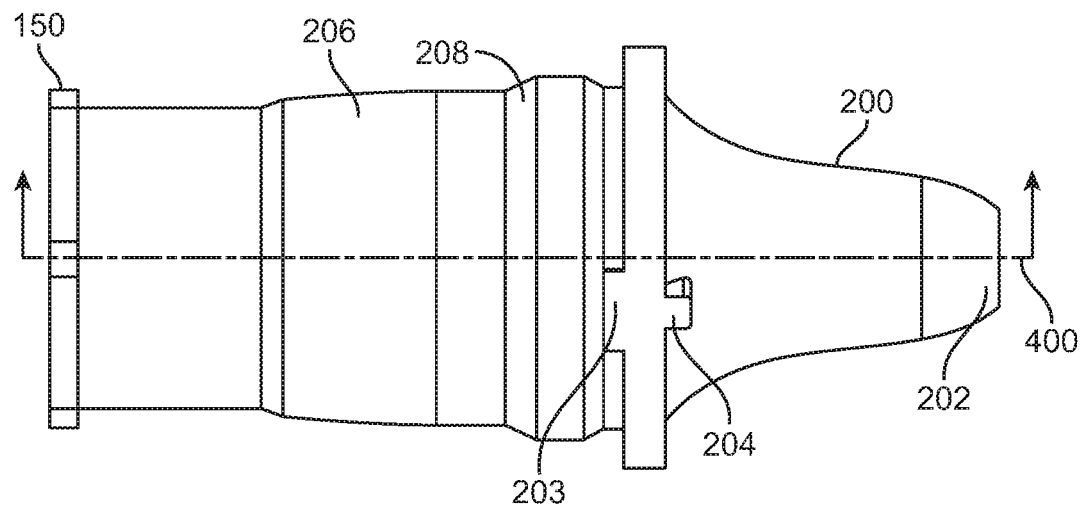
FIG. 6A and FIG. 6B illustrate an exterior view and a slice view, respectively of a nozzle and a nozzle cap in an open position, in accordance with some embodiments.
Figure 6B:
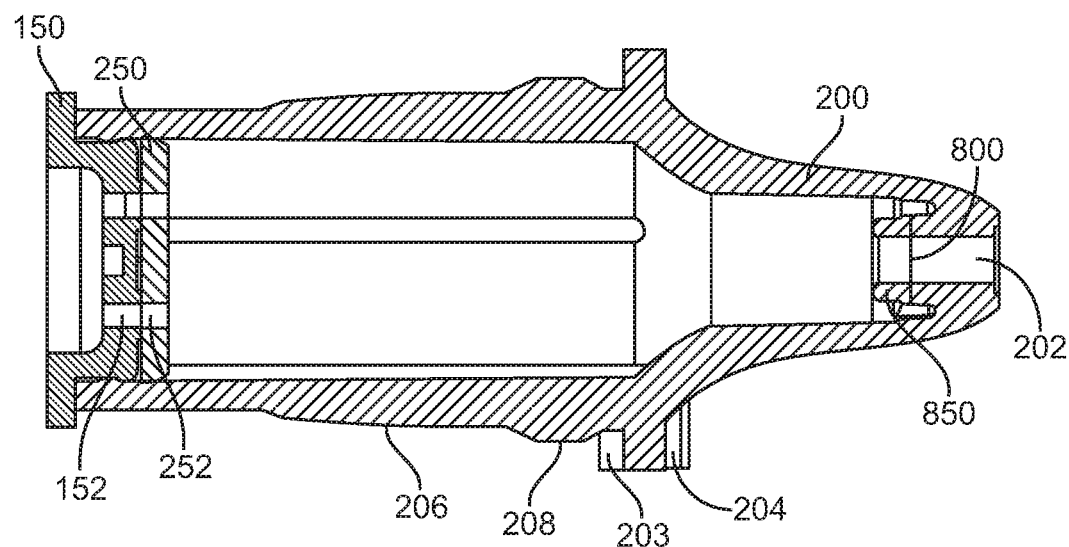

FIG. 5A and FIG. 5B illustrate an exterior view and a slice view, respectively, of a nozzle and a nozzle cap in a closed position, in accordance with some embodiments. FIG. 6A and FIG. 6B illustrate an exterior view and a slice view, respectively, of a nozzle and a nozzle cap in an open position, in accordance with some embodiments. In some cases, the flow control device may comprise an axis of rotation 400. Rotation of the nozzle about the axis of rotation 400 relative to the reservoir may align the one or more apertures in the reservoir interface 152 with the one or more apertures in the nozzle cap 252.

FIG. 5A, FIG. 5B, FIG. 6A, and FIG. 6B illustrate an interaction between a nozzle 200, nozzle cap 250, and reservoir interface 150. As illustrated, nozzle cap 250 may be rotationally fixed relative to nozzle 200 while reservoir interface 150 may be rotationally free relative to nozzle 200. In some cases, reservoir interface 150 may be axially fixed relative to nozzle 200 but rotationally free. In some cases, a nozzle 200, nozzle cap 250, and reservoir interface 150 may comprise portions of a nozzle assembly which may be removable from a reservoir in order to fill a reservoir. A nozzle cap 250 may be axially fixed to nozzle 200 by way of a snap fit, an interference fit, a press fit, a screw, etc. In some cases, once a reservoir interface 150 is attached to a nozzle 200, it may not be removed. A filter 220 may disposed in between reservoir interface 150 and nozzle 200, thereby securing filter 220. Looking at apertures 152 and nozzle cap 250, in FIG. 5B, it is illustrated that both apertures are not aligned thereby impeding fluid passage between reservoir 100 and nozzle 200. Looking at apertures 152 and apertures 252, in FIG. 6B, it is illustrated that both apertures are aligned allowing for fluid passage between reservoir 100 and nozzle 200.

Figure 7A:
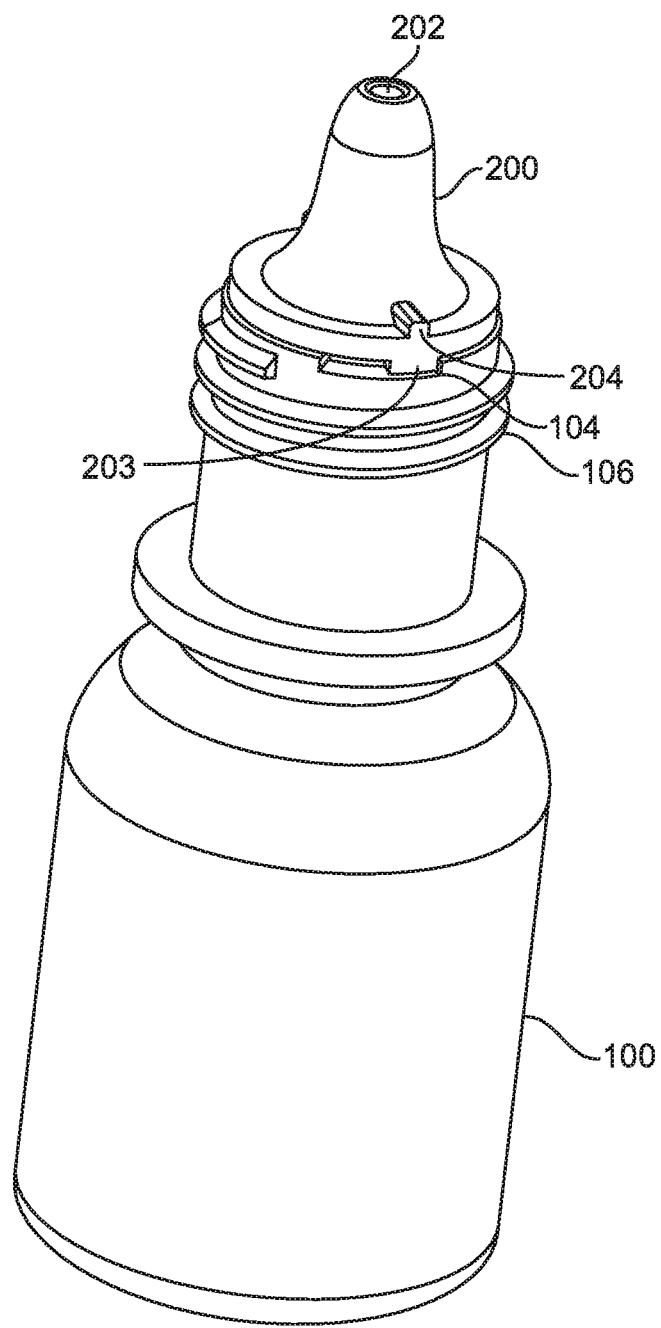
FIG. 7A and FIG. 7B illustrate ridges on a reservoir facing surface of a nozzle received by rotation guides on a reservoir in an open position and a closed position, respectively, in accordance with some embodiments.
Figure 7B:
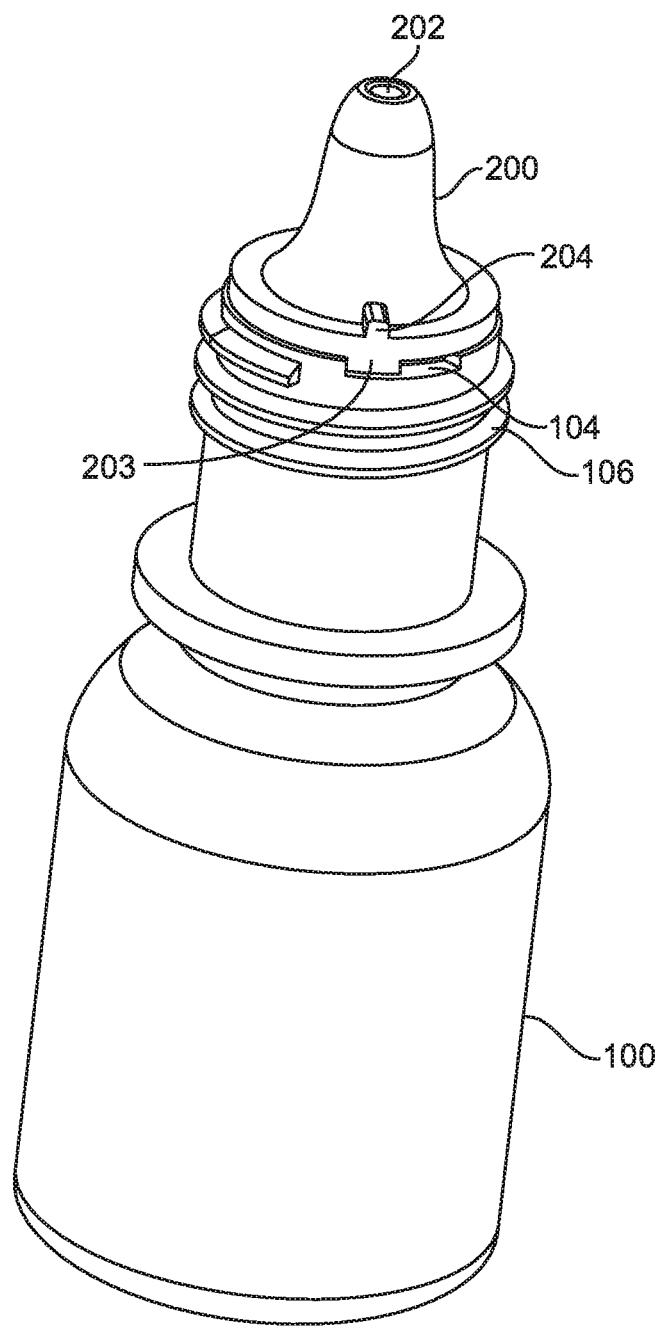

FIG. 7A and FIG. 7B illustrate ridges on a reservoir facing surface of a nozzle received by rotation guides on a reservoir in an open position and a closed position, respectively, in accordance with some embodiments. In some embodiments, the nozzle comprises a second one or more ridges on a reservoir facing surface 203, the second one or more ridges receivable by the reservoir. In some embodiments, the reservoir comprises one or more rotation guides 104, the second one or more ridges on a reservoir facing surface received by the one or more rotation guides. In some embodiments, the second one or more ridges on the bottle-facing surface received by the rotation guides limits an angle of rotation of the nozzle relative to the reservoir.

The interaction of rotation guides 104 and ridges 203 may serve to limit an angle over which a nozzle assembly may be rotated. In the illustrated example, an angle of rotation may be limited to about 30 degrees. An angle of rotation may be limited based on a number a geometry of apertures in a nozzle cap. For example, there may be a rotational stop at a fully open and full closed positions. For example, if a nozzle cap had 4 apertures which were equally spaced radially about an axis of rotation, an angle of rotation may be limited to 45 degrees. Looking at ridges 203 relative to rotation guide 104 in FIG. 7A, the position of the nozzle may be at a first rotational stop, such that the nozzle is in an open position. Looking at ridges 203 relative to rotation guide 104 in FIG. 7B, the position of the nozzle may be at a second rotational stop, such that the nozzle is in a closed position.

Figure 8A:
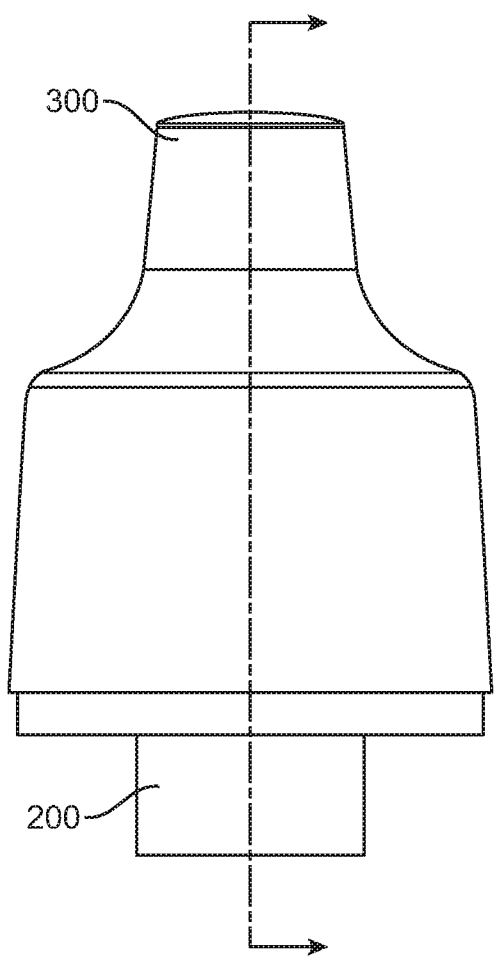
FIG. 8A and FIG. 8B illustrate an exterior view and a slice view, respectively, of a nozzle and a bottle cap, in accordance with some embodiments.
Figure 8B:
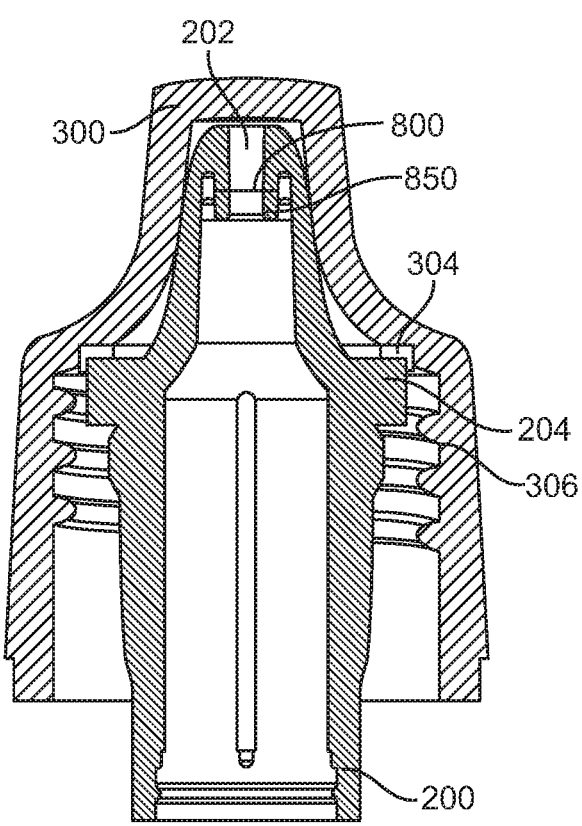

FIG. 8A and FIG. 8B illustrate an exterior view and a slice view, respectively, of a nozzle and a bottle cap, in accordance with some embodiments. In some embodiments, the flow control device further comprises a bottle cap 300. Rotation of the bottle cap about the axis of rotation 400 relative to the reservoir may rotate the nozzle 200 about the axis of rotation 400 relative to the reservoir 100. In some embodiments, the bottle cap comprises a screw cap. The exterior of the reservoir may comprise threads 106. The interior of a bottle cap may comprise threads 306. As illustrated, ridges 204 on a cap facing surface of nozzle 200 may be received within alignment channels 304 within an interior of the bottle cap 300. As the cap is screwed on, the alignment channels 304 may catch the ridges 204 thereby rotating the nozzle assembly placing the flow control device in a rotationally closed position. As illustrated, when the cap is fully screwed on, the cap may seal outlet 202.

Figure 9A:
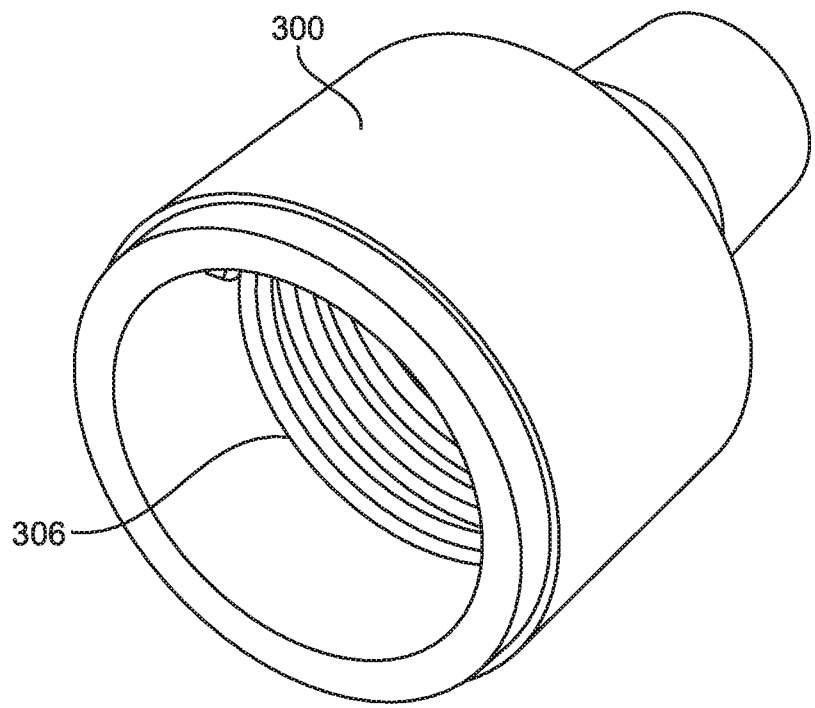
FIG. 9A and FIG. 9B illustrate two views of a bottle cap, in accordance with some embodiments.
Figure 9B:
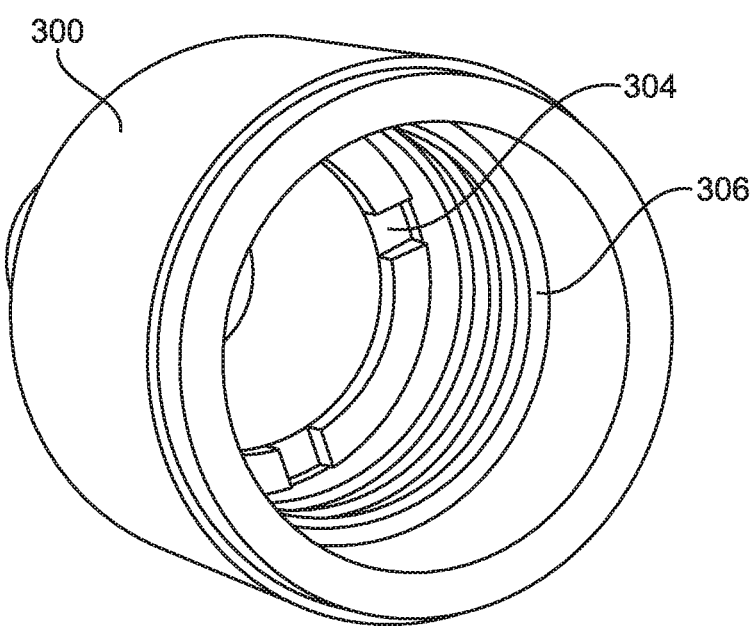
Figure 10:
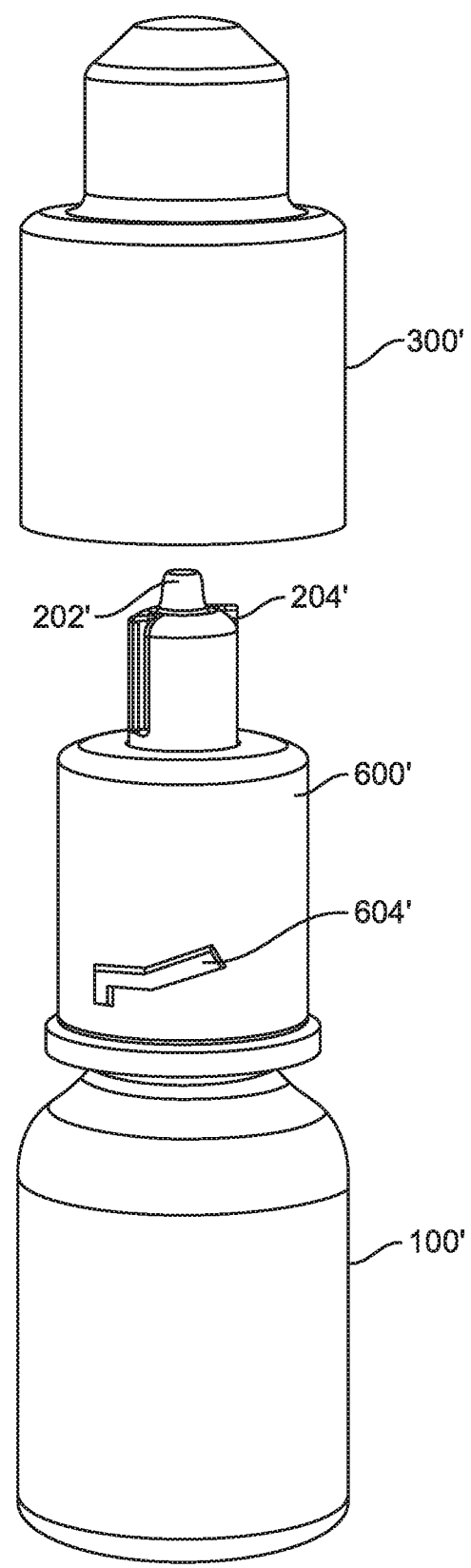
FIG. 10 illustrates a partially exploded view of another example flow control device, in accordance with some embodiments.

FIG. 9A and FIG. 9B illustrate two views of a bottle cap, in accordance with some embodiments. In some embodiments, the nozzle comprises a first one or more ridges on a bottle-cap facing surface 204, the first one or more ridges receivable by the bottle cap. In some embodiments, the bottle cap 300 comprises one or more alignment channels 304 on an interior surface of the bottle cap, the first one or more ridges on the bottle-cap facing surface of the nozzle cap received within the one or more alignment channels. Bottle cap 300 may also comprise threads 306.

FIG. 10 illustrates a partially exploded view of another example flow control device, in accordance with some embodiments. As illustrated, the flow control device may comprise a reservoir 100', a nozzle 200', and a cap 300'. The flow control device may comprise a nozzle interface 600'. As illustrated a nozzle interface 600' may have one or more alignment guides 604'. As illustrated the one or more alignment guides 604' may be configured to be received by screw threads within an interior of a bottle cap 300'. The alignment guides 604' may provide a rotational stop when a cap 300' is screwed on. The alignment guides 604' may provide a guide to allow tightening of the nozzle interface 600' relative to the reservoir 100'. The nozzle 200' may comprise an outlet 202'. The nozzle 200' may have one or more ridges 204' on a cap facing side. The one or more ridges 204' may be received by one or more alignment channels on an interior of a bottle cap 300' to rotate a nozzle relative to the reservoir 100'.

Figure 11:
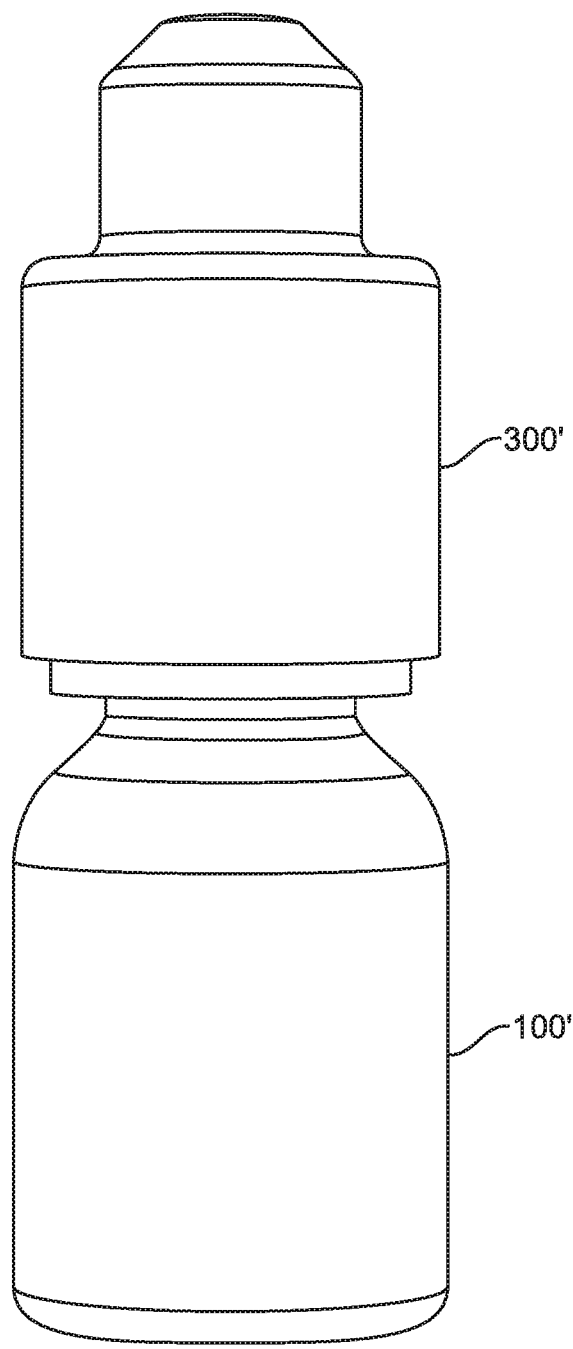
FIG. 11 illustrates an exterior view of the flow control device of FIG. 10 integrated with a compressible bottle, in accordance with some embodiments.

FIG. 11 illustrates an exterior view of the flow control device of FIG. 10 integrated with a compressible bottle, in accordance with some embodiments. FIG. 11 illustrates reservoir 100' and cap 300'.

Figure 12:
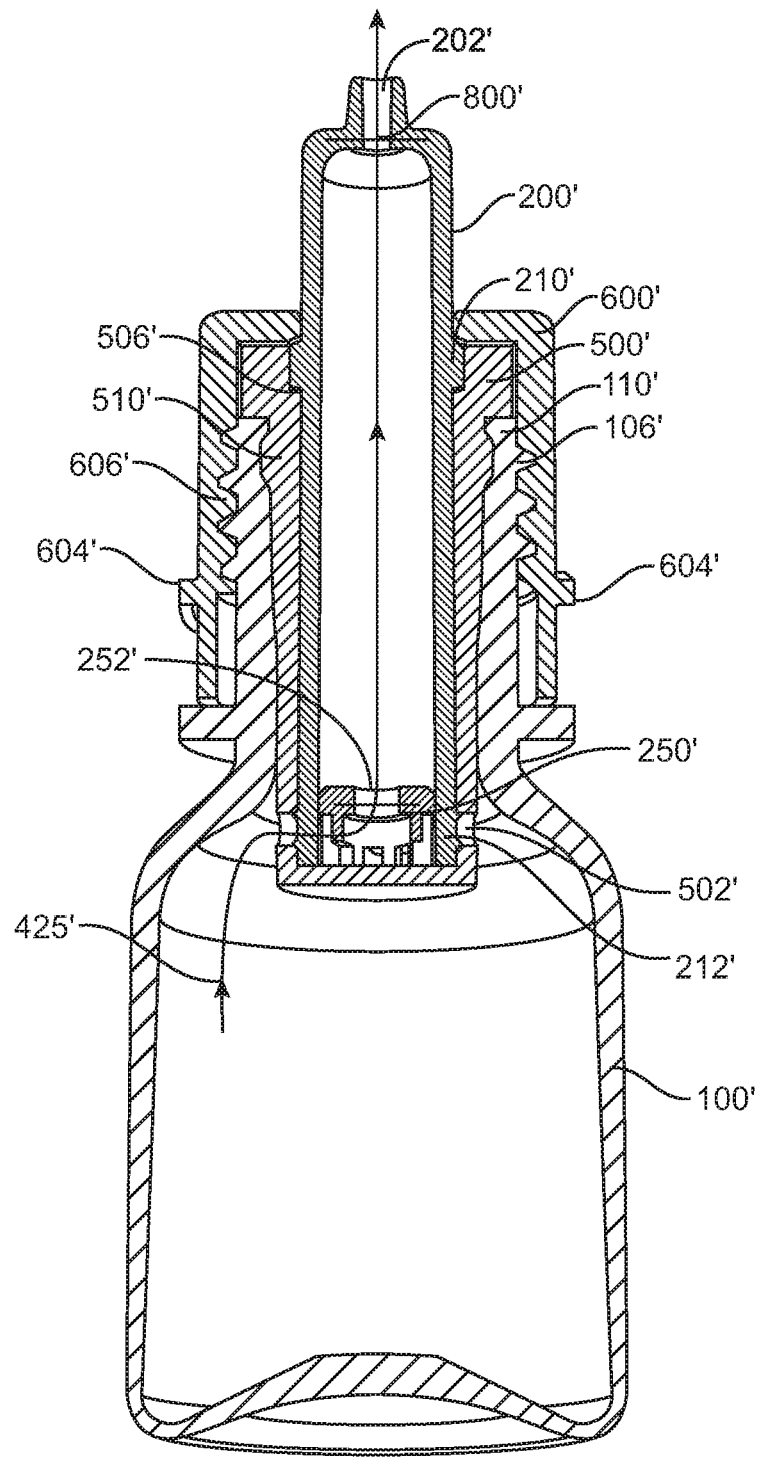
FIG. 12 illustrates a slice view of the flow control device of FIG. 10 integrated with a compressible bottle, in accordance with some embodiments.

FIG. 12 illustrates a slice view of the flow control device of FIG. 10 integrated with a compressible bottle, in accordance with some embodiments.

The flow control device may comprise a reservoir 100'. The reservoir may comprise an ophthalmic formulation disposed therein. The ophthalmic formulation may comprise an ophthalmic agent and a preservative, as described elsewhere herein for example in the sections "Ophthalmic Agent" and "Preservative". The ophthalmic formulation may comprise any of the example formulations disclosed herein, for example in the section "Solution, Emulsion, or Suspension". Reservoir 100' may comprise a compressible bottle, for example the reservoir of a commercial eyedrop bottle. In some cases, reservoir 100' may utilize a commonly available commercial bottle. In other cases, reservoir 100' may be a proprietary bottle designed for a specific application, such as the systems, methods, devices, and kits disclosed herein.

A reservoir of the present disclosure may comprise an interior volume which may contain an ophthalmic formulation as disclosed herein. A reservoir may comprise an interior volume of about 2.5 cc. A reservoir may comprise an interior volume of about 8 cc. A reservoir may comprise an interior volume of at least about 0.2 cubic centimeters (cc), at least about 0.5 cc, at least about 1 cc, at least about 1.5 cc, at least about 2 cc, at least about 2.5 cc, at least about 3 cc, at least about 4 cc, at least about 5 cc, at least about 6 cc, at least about 7 cc, at least about 8 cc, at least about 10 cc, or more. A reservoir may comprise an interior volume between about 0.1 cc and about 10 cc, between about 1 cc and about 10 cc, between about 2 cc and about 10 cc, between about 2.5 cc and about 10 cc, etc. For example, an 8 cc bottle may dispense about 5 cc of an ophthalmic formulation. For example, a 2.5 cc about, may dispense about 2 cc of an ophthalmic formulation.

In some cases, an ophthalmic formulation may at least partially fill an interior volume of a reservoir. An ophthalmic formulation may fill at least about 1%, at least about 2%, at least about 5%, at least about 10%, at least about 20%, at least about 50%, at least about 70%, at least about 80%, at least about 90%, at least about 95%, or more of an interior volume of the reservoir. An ophthalmic formulation may fill between about 1% and about 99%, about 10% and about 98%, about 25% and about 50%, about 10% and about 50%, etc. of an interior volume of the reservoir.

A reservoir of the present disclosure may be made of a plastic. A plastic may be compressible. A plastic may comprise one or combination of various polyolefins, polypropylenes, polyethylenes, etc. A reservoir may comprise a low-density polyethylene (e.g. Nalgene™). A reservoir may comprise a reservoir of a compressible bottle. The bottle may be made of a material which is sufficiently flexible for a person to at least partially collapse the sides of the reservoir, thereby increasing a pressure within the reservoir.

The flow control device may comprise a reservoir interface 500', disposed at a mouth of the reservoir. The reservoir interface may comprise one or more apertures 502'. The one or more apertures in the reservoir interface may fluidically connect an interior of the reservoir with an exterior of the reservoir. The one or more aperture may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

As illustrated in FIG. 12, the reservoir interface 500' may comprise one or more retention features 510' and 518'. The mouth of the reservoir may comprise one or more retention features 110' which may receive the one or more retention features 510' of the reservoir interface 500. When the reservoir interface is in place within a mouth of the reservoir, an orientation of the reservoir interface relative to the reservoir may be rotationally fixed. The retention features 510' may comprise a snap fit, an interference fit, a press fit, a screw, etc. Rotational fixation of the reservoir interface may be aided by a glue, a weld, a heat seal, etc. In some cases, the reservoir interface may be removable. The reservoir interface 500' may comprise a cavity in which a nozzle 200' may rotate.

The flow control device may comprise a nozzle 200'. The nozzle may comprise at least one outlet 202' and a nozzle cap 250'. The nozzle may comprise an interior volume, which interior volume may comprise a preservative removing device. A preservative removing device may comprise any example of a preservative removing device as disclosed herein, for example, the preservative removal agent and matrices as disclosed in the section "Preservative Removal Agent" elsewhere herein. A nozzle may comprise an interior volume of about 0.5 cc. A nozzle may comprise an interior volume of about 0.1 cc. A nozzle may comprise an interior volume of about 1 cc. A nozzle may comprise an interior volume of at least about 0.05 cubic centimeters (cc), at least about 0.1 cc, at least about 0.2 cc, at least about 0.3 cc, at least about 0.4 cc, at least about 0.5 cc, at least about 0.6 cc, at least about 0.7 cc, at least about 0.8 cc, at least about 1 cc, at least about 1.5 cc, at least about 2 cc, at least about 5 cc, or more. A reservoir may comprise an interior volume between about 0.01 cc and about 5 cc, between about 0.1 cc and about 5 cc, between about 0.5 cc and about 1.5 cc, between about 0.5 cc and about 5 cc, etc.

In some cases, a preservative removing device may at least partially fill an interior volume of a nozzle. For example, a preservative removing device may comprise a polymeric matrix. A preservative removing device may fill at least about 1%, at least about 2%, at least about 5%, at least about 10%, at least about 20%, at least about 50%, at least about 70%, at least about 80%, at least about 90%, at least about 95%, or more of an interior volume of the nozzle. A preservative removing device may fill between about 1% and about 99%, about 10% and about 98%, about 25% and about 50%, about 10% and about 50%, etc. of an interior volume of the nozzle.

The nozzle 200' may comprise and outlet 202'. The outlet may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The outlet may comprise an aperture diameter of between about 10 and about 5000 microns, between about 10 and about 2500 microns, between about 10 and about 1000 microns, between about 10 and about 500 microns, etc.

The nozzle cap 250' may comprise one or more apertures 252'. The one or more apertures in the nozzle cap may fluidically connect the outlet 202' and an exterior of the nozzle. The one or more apertures in the nozzle cap may fluidically connect to a reservoir-facing surface of the nozzle. The one or more aperture may comprise at least 1 aperture, at least 2 apertures, at least 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

In some cases, the nozzle cap 250' is rotationally fixed relative to the nozzle 200'. In some cases, the nozzle cap is rotationally fixed relative to the nozzle by one or more retention features. The retention features may comprise a snap fit, an interference fit, a press fit, a screw, etc. Rotational fixation of the nozzle cap may be aided by a glue, a weld, a heat seal, etc. In some cases, the nozzle cap may be removable. The nozzle cap may aid in retention of a preservative removing device within an interior volume of the nozzle.

In some cases, a nozzle cap may comprise a filter. A filter may comprise a mesh or a screen. A filter may comprise a polyester mesh. A filter may comprise a paper mesh. A filter may be disposed within nozzle cap 250'. A filter may be disposed adjacent a nozzle cap 250'. A filter may comprise a mesh size of about 25 microns. A filter may comprise a mesh size of at least about 1 micron, at least about 2 microns, at least about 5 microns, at least about 10 microns, at least about 20 microns, at least about 50 microns, at least about 100 microns or more. A filter may comprise a mesh size of at most about 1 mm, at most about 500 microns, at most about 250 microns, at most about 100 microns, at most about 50 microns, at most about 25 microns, or less. A filter may comprise a mesh size of between about 1 and about 50 microns, between about 10 and about 50 microns, between about 1 and about 30 microns, between about 20 and about 30 microns, etc.

In some embodiments, the nozzle 200' may comprise one or more retention features on an exterior surface of the nozzle. The retention features 210' may abut a shelf 506' of the reservoir interface 500'. In some cases, the retention features may allow for rotation of the nozzle relative to the reservoir interface while limiting translation of the nozzle along an axis of rotation. In some cases, the nozzle may be removable. The nozzle may be removable with a nozzle cap in place.

Also illustrated in FIG. 12 is outlet filter 800'. A filter may comprise a mesh or a screen. A filter may comprise a polyester mesh. A filter may comprise a paper mesh. A filter 800' may be disposed within outlet cap. A filter may be disposed adjacent outlet cap. A filter may be disposed within an outlet cap. A filter may comprise a mesh size of about 25 microns. A filter may comprise a mesh size of at least about 1 micron, at least about 2 microns, at least about 5 microns, at least about 10 microns, at least about 20 microns, at least about 50 microns, at least about 100 microns or more. A filter may comprise a mesh size of at most about 1 mm, at most about 500 microns, at most about 250 microns, at most about 100 microns, at most about 50 microns, at most about 25 microns, or less. A filter may comprise a mesh size of between about 1 and about 50 microns, between about 10 and about 50 microns, between about 1 and about 30 microns, between about 20 and about 30 microns, etc.

Also illustrated in FIG. 12 is nozzle interface 600'. Nozzle interface 600' may comprise an interior thread 606', which may screw on to the threads 106' of the reservoir 100'. When the nozzle interface 600' is screwed in place, the nozzle interface may limit axial translation of the nozzle 200' along the axis of rotation 400'. When the nozzle interface 600' is screwed in place, the nozzle interface may allow rotation of the nozzle 200' along the axis of rotation. The nozzle interface may provide a retaining force to retention feature 110'. In some cases, the nozzle interface may be screwed on or off. In some cases, once a nozzle interface is screwed on to a reservoir, it may be difficult to remove a nozzle interface. FIG. 12 also illustrates a flow path 425' through the device.

Figure 13A:
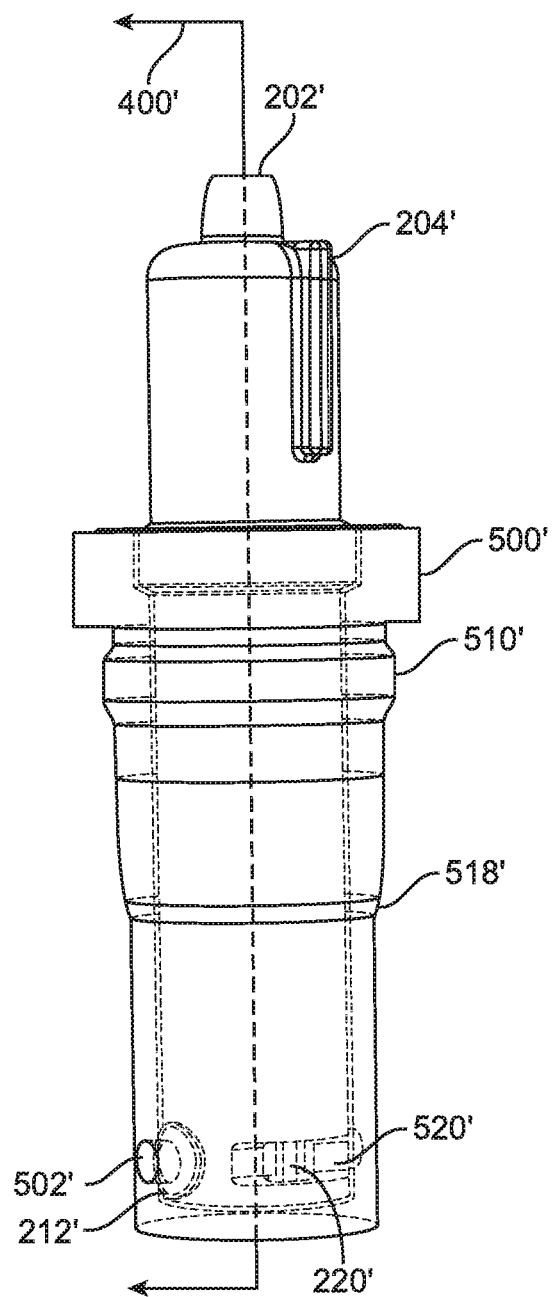
FIG. 13A and FIG. 13B illustrate side views of an interaction between a nozzle and reservoir interface of the flow control device of FIG. 10 integrated with a compressible bottle, in accordance with some embodiments.
Figure 13B:
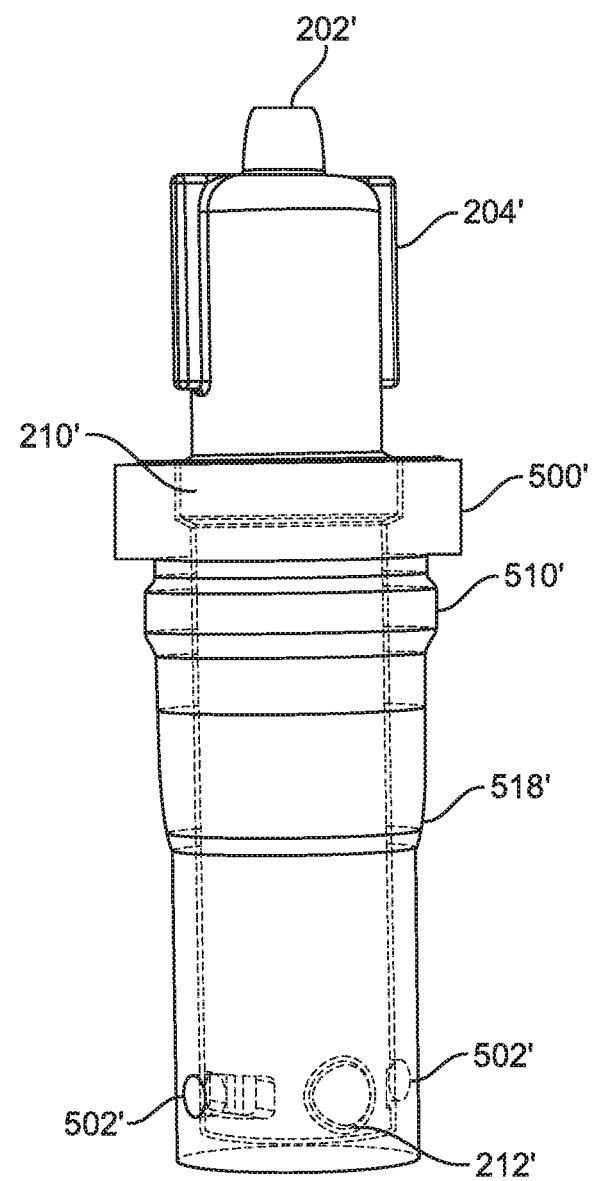
Figure 14:
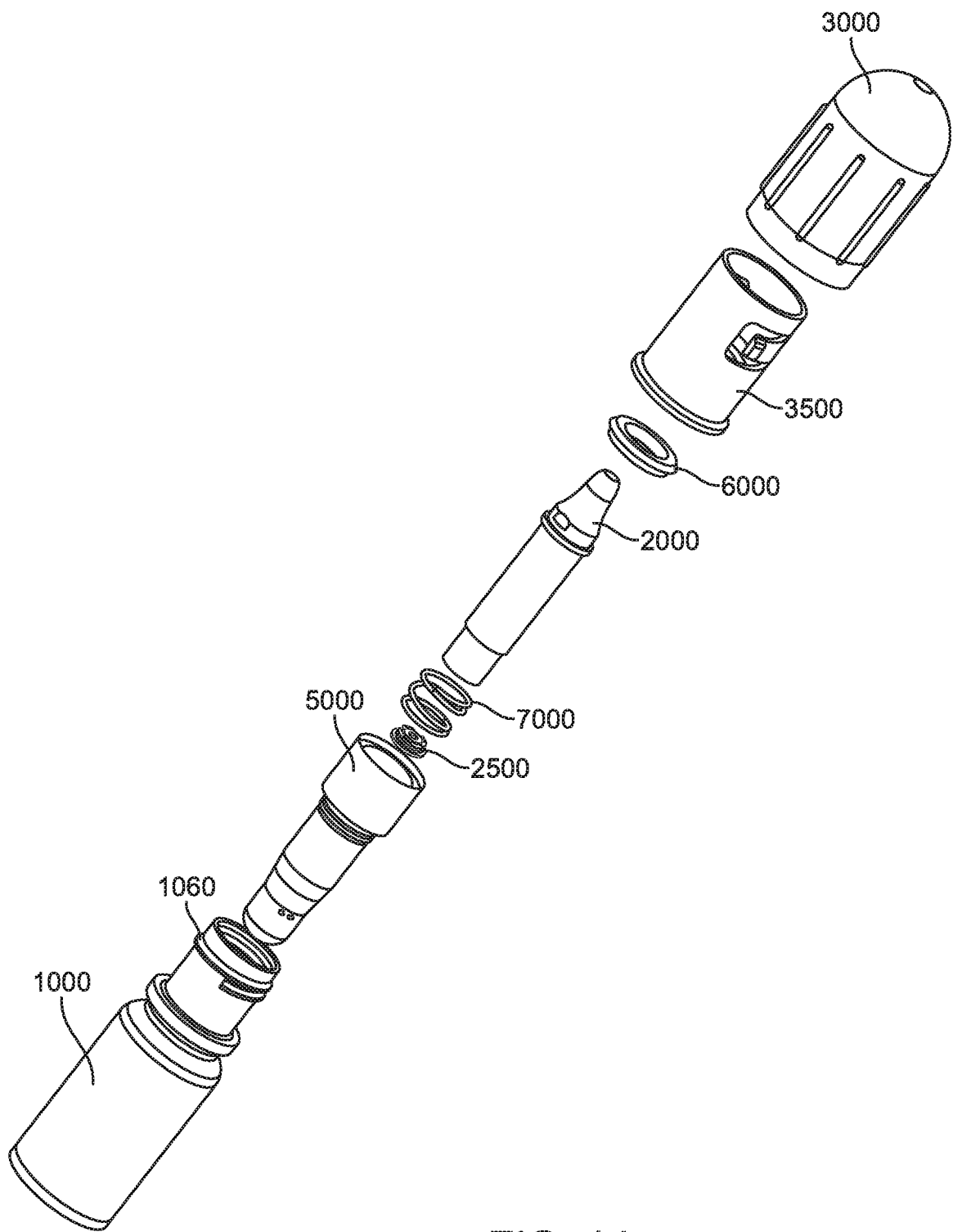
FIG. 14 illustrates a partially exploded view of another example flow control device, in accordance with some embodiments.

FIG. 13A and FIG. 13B illustrate an interaction between a nozzle 200' and reservoir interface 500'. As illustrated, reservoir interface 500' may be rotationally free relative to nozzle 200'. In some cases, reservoir interface 500' may be axially fixed relative to nozzle 200' but rotationally free. In some cases, a nozzle 200' and reservoir interface 500' may comprise portions of a nozzle assembly which may be removable from a reservoir in order to fill a reservoir. In some cases, once a reservoir interface 500' is attached to a nozzle 200', it may not be removed. Reservoir interface 500' may comprise retention features 510' and 518'. Reservoir interface 500' may also comprise one or more apertures 502'. When the nozzle 200' is rotated about an axis 400', one or more inlet apertures 212' in the nozzle 200' may be aligned with the one or more apertures 502' in the reservoir interface.

The one or more apertures 502' in the reservoir interface may fluidically connect the outlet 202' and an exterior of the nozzle via the one or more apertures in the nozzle cap 252' and the one or more inlet apertures in the nozzle 212'. The one or more apertures in the reservoir interface may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures in the reservoir interface may comprise a diameter of at least about 1 microns, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

The one or more inlet apertures 212' in the nozzle 200' may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more inlet apertures 212' in the nozzle 200' may comprise a diameter of at least about 1 microns, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

FIG. 13A and FIG. 13B also illustrate rotation guides in reservoir interface 500' in an open position and a closed position, respectively. In some embodiments, the nozzle comprises one or more alignment features 220', the one or more alignment features receivable within the rotation guides 520'. In some embodiments, the reservoir interface comprises one or more rotation guides 520'. In some embodiments, the one or more alignment features receivable within the rotation guides 520 limit an angle of rotation of the nozzle relative to the reservoir.

The interaction of rotation guides 520' and alignment features 220' may serve to limit an angle over which a nozzle assembly may be rotated. In the illustrated example, an angle of rotation may be limited to about 20 degrees. An angle of rotation may be limited based on a number and geometry of apertures in a nozzle cap. For example, there may be a rotational stop at a fully open and full closed positions. For example, in the illustrated example, there may be two equally spaced apertures 212', so an angle of rotation may be less than 180 degrees. Looking at alignment feature 220' relative to rotation guide 520' in FIG. 13A, the position of the nozzle may be at a first rotational stop, such that the nozzle is in an open position. Looking at alignment feature 220' relative to rotation guide 520' in FIG. 13B, the position of the nozzle may be at a second rotational stop, such that the nozzle is in a closed position.

FIG. 14 illustrates a partially exploded view of another example flow control device, in accordance with some embodiments. As shown, the example flow control device may comprise a reservoir 1000, reservoir interface 5000, nozzle 2000, nozzle cap 2500, spring element 7000, nozzle interface 6000, and a two-part cap comprising exterior 3000 and interior 3500. As shown in the illustrated example, rather than rotating, a nozzle may translate in order to control a flow through the device. The flow control device may comprise a spring element 7000 which may provide a restoring force to oppose a compressing motion along an axis of translation. A spring element may be metal, for example, alloy steel, chrome silicon, carbon steel, cobalt-nickel, copper alloys, nickel alloys, stainless steel, titanium, etc.

Figure 15A:
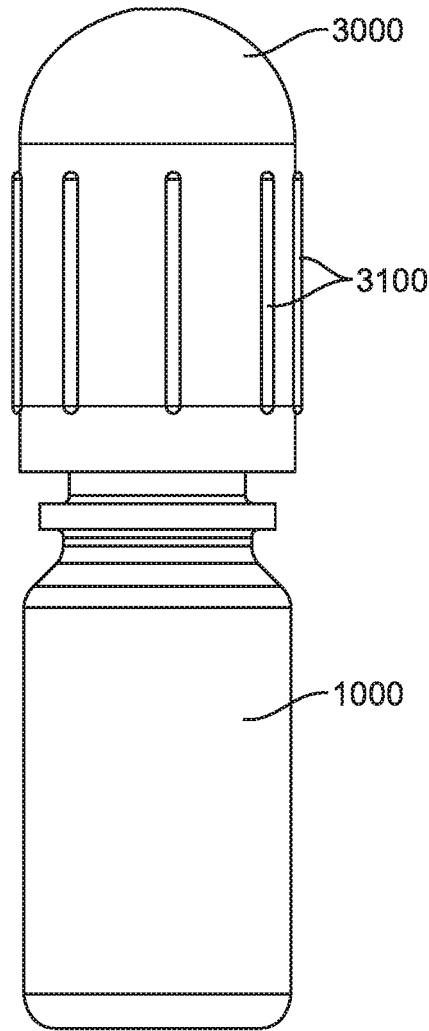
FIG. 15A and FIG. 15B illustrate exterior views with a cap on and a cap off of the flow control device of FIG. 14, in accordance with some embodiments.
Figure 15B:
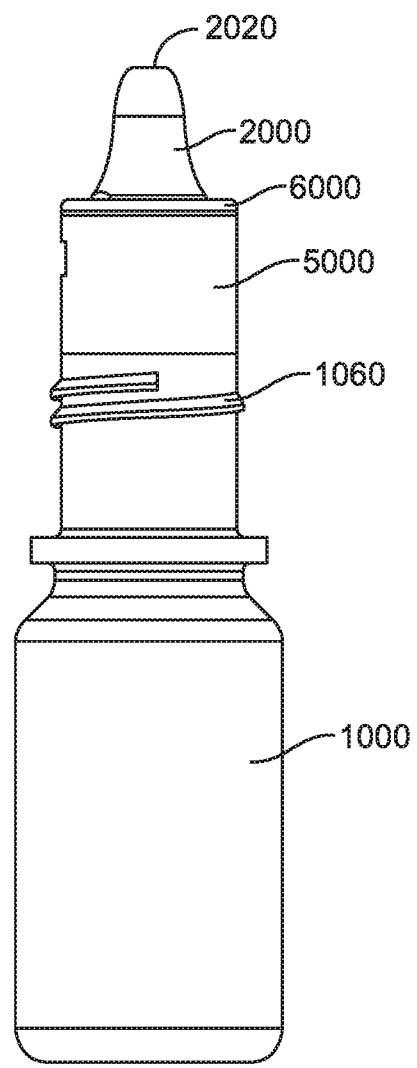

FIG. 15A and FIG. 15B illustrate an exterior view of the flow control device of FIG. 14, in accordance with some embodiments. FIG. 15A and FIG. 15B illustrate reservoir 1000 and cap 3000. As illustrated cap 3000 may be screwed on or off of threads 1060 of reservoir 1000. When a cap is in place, cap 3000 may cover outlet 2020 of nozzle 2000. Cap 3000 may have exterior features 3100 which may aid in removing or applying the cap. In some cases, cap 3000 comprises a closure assembly which is resistant to manipulation from a child. In some cases, cap 3000 produces an audible or tactile click when moved into a closed state.

Figure 16A:
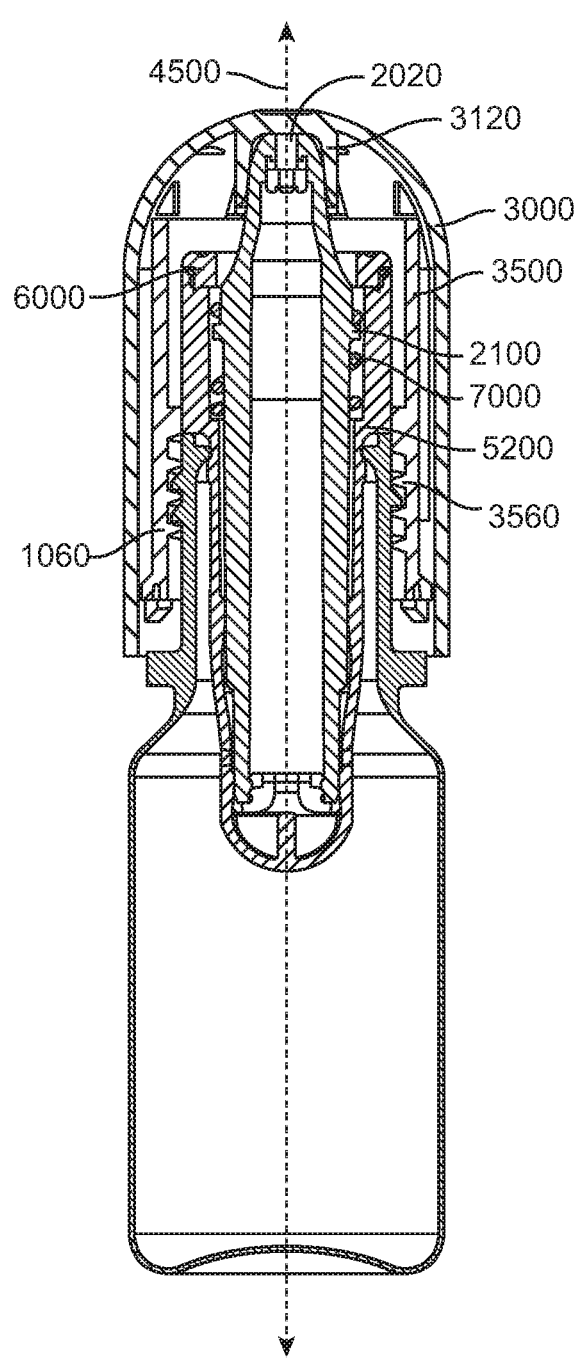
FIG. 16A, FIG. 16B illustrate slice views of the flow control device of FIG. 14 with a cap on and a cap off, respectively, in accordance with some embodiments.
Figure 16B:
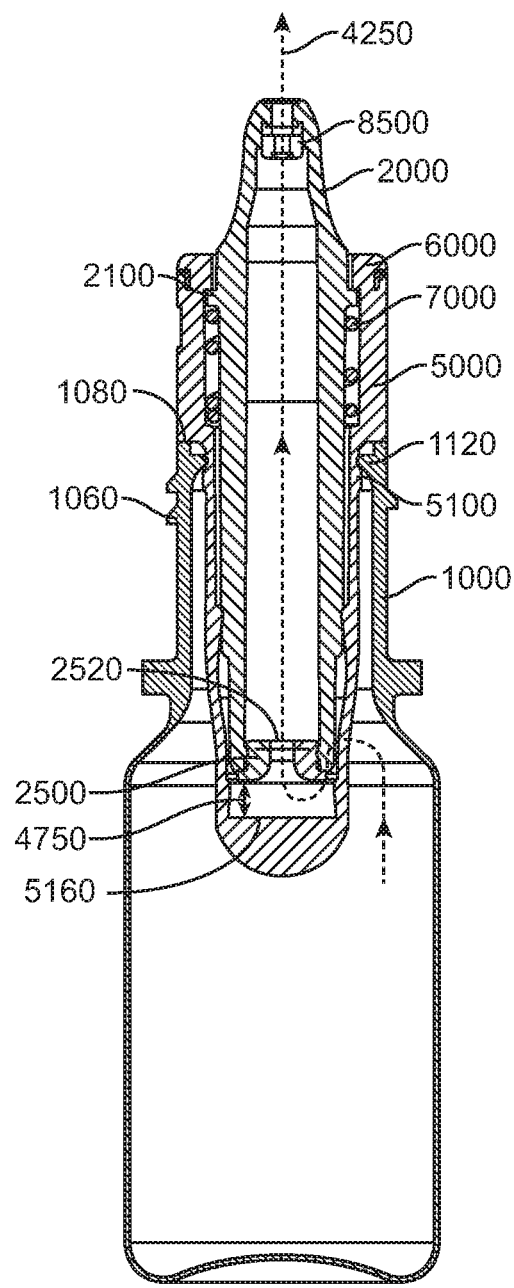

FIG. 16A and FIG. 16B illustrate slice views of the flow control device of FIG. 14 with a cap on and a cap off, respectively, in accordance with some embodiments. FIG. 16A and FIG. 16B illustrate slice views of a flow control device in a closed position and in an open position, in accordance with some embodiments. Translation of the nozzle may prevent flow of the ophthalmic formulation between the interior of the nozzle and the reservoir, thereby stabilizing a concentration of the preservative in the ophthalmic formulation. In some cases, the flow control device may comprise an axis of translation 4500.

The nozzle assembly may comprise a bead seal configuration. As shown, when a cap 3000 is in place a nozzle 2000 may slide along axis of translation 4500 compressing spring element 7000. In some cases, when a cap is fully in place bead seal elements 2160 on a reservoir interface-facing surface of the nozzle are in contact with a nozzle-facing wall of the reservoir interface 5000. In some cases, when a cap is fully in place bead seal elements 5060, 5080 on a nozzle-facing surface of the reservoir interface are in contact with a reservoir interface-facing wall of the nozzle 2000. The bead seal elements 2160 and 5060, 5080 may comprise a fluidic seal. In some case, a fluidic seal may comprise contact between a bottom surface of nozzle cap 2500 and surface 5160 of reservoir interface 5000.

A translation distance 4750 is illustrated in FIG. 16B. In some cases, surface 5160 may comprise a first translation stop. In some cases, bead seal elements 2160 and 5060 may comprise a first translation stop. In some cases, threads of cap 3000 may comprise a first translation stop. A second translation stop may comprise an interaction between outlet 2020 and a seal cap 3120 of cap 3000. A second translation stop may comprise an interaction between retention features 2100 on a reservoir seal-facing surface of nozzle 2000 with nozzle interface 6000. Nozzle interface 6000 may comprise a retention ring. Nozzle interface 6000 may be ultrasonically welded, heat sealed, glued, or bonded to reservoir interface 5000. In some cases, nozzle interface 6000 may be removable. In some cases, nozzle interface 6000 may comprise a thread, a snap fit, a press fit, etc. A spring element 7000 may be compressed between retention feature 2100 and a shelf 5200 of the reservoir interface.

Translation of the nozzle along the axis of translation 4500 relative to the reservoir may fluidically connect the one or more apertures 5020 in the reservoir interface 5000 with the one or more apertures in the nozzle cap 2520. Looking at apertures 5020 and apertures 2520, in FIG. 16B, it is illustrated that both apertures are fluidically connected allowing for fluid passage between reservoir 1000 and nozzle 2000. Looking at apertures 5020 and nozzle 2000, in FIG. 16A, it is illustrated that nozzle cap 2500 abuts a bottom surface 5160 of the reservoir interface, thereby impeding fluid passage between reservoir 1000 and nozzle 2000. FIG. 16B illustrates flow path 4250 through the device.

FIG. 16B also illustrates an interaction between reservoir interface 5000 and reservoir 1000. The reservoir interface 5000 may comprise one or more retention features 5100 and 5180. The mouth of the reservoir may comprise one or more retention features 1120 which may receive the one or more retention features 5100 of the reservoir interface 5000. When the reservoir interface is in place within a mouth of the reservoir, an orientation of the reservoir interface relative to the reservoir may be rotationally fixed. The retention features 5100, 5180 may comprise a snap fit, an interference fit, a press fit, a screw, etc. Rotational fixation of the reservoir interface may be aided by a glue, a weld, a heat seal, etc. In some cases, the reservoir interface may be removable. The reservoir interface 5000 may comprise a cavity 5140 in which a nozzle 2000 may translate.

As illustrated, the flow control device may comprise a reservoir 1000. The reservoir may comprise an ophthalmic formulation disposed therein. The ophthalmic formulation may comprise an ophthalmic agent and a preservative, as described elsewhere herein for example in the sections "Ophthalmic Agent" and "Preservative". The ophthalmic formulation may comprise any of the example formulations disclosed herein, for example in the section "Solution, Emulsion, or Suspension". Reservoir 1000 may comprise a compressible bottle, for example the reservoir of a commercial eyedrop bottle. In some cases, reservoir 1000 may utilize a commonly available commercial bottle. In other cases, reservoir 1000 may be a proprietary bottle designed for a specific application, such as the systems, methods, devices, and kits disclosed herein.

A reservoir of the present disclosure may comprise an interior volume which may contain an ophthalmic formulation as disclosed herein. A reservoir may comprise an interior volume of about 2.5 cc. A reservoir may comprise an interior volume of about 8 cc. A reservoir may comprise an interior volume of at least about 0.2 cubic centimeters (cc), at least about 0.5 cc, at least about 1 cc, at least about 1.5 cc, at least about 2 cc, at least about 2.5 cc, at least about 3 cc, at least about 4 cc, at least about 5 cc, at least about 6 cc, at least about 7 cc, at least about 8 cc, at least about 10 cc, or more. A reservoir may comprise an interior volume between about 0.1 cc and about 10 cc, between about 1 cc and about 10 cc, between about 2 cc and about 10 cc, between about 2.5 cc and about 10 cc, etc. For example, an 8 cc bottle may dispense about 5 cc of an ophthalmic formulation. For example, a 2.5 cc about, may dispense about 2 cc of an ophthalmic formulation.

In some cases, an ophthalmic formulation may at least partially fill an interior volume of a reservoir. An ophthalmic formulation may fill at least about 1%, at least about 2%, at least about 5%, at least about 10%, at least about 20%, at least about 50%, at least about 70%, at least about 80%, at least about 90%, at least about 95%, or more of an interior volume of the reservoir. An ophthalmic formulation may fill between about 1% and about 99%, about 10% and about 98%, about 25% and about 50%, about 10% and about 50%, etc. of an interior volume of the reservoir.

A reservoir of the present disclosure may be made of a plastic. A plastic may be compressible. A plastic may comprise one or combination of various polyolefins, polypropylenes, polyethylenes, etc. A reservoir may comprise a low-density polyethylene (e.g. Nalgene™). A reservoir may comprise a reservoir of a compressible bottle. The bottle may be made of a material which is sufficiently flexible for a person to at least partially collapse the sides of the reservoir, thereby increasing a pressure within the reservoir.

Figure 17A:
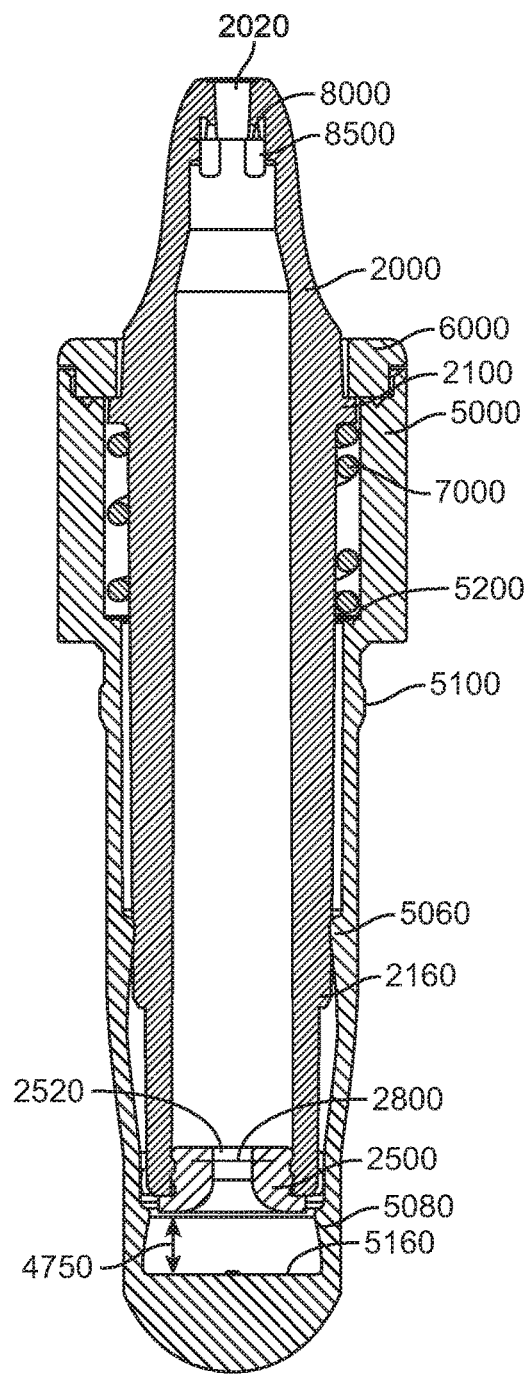
FIG. 17A, FIG. 17B illustrate a slice view and an exterior view, respectively, of a nozzle assembly of the flow control device of FIG. 14, in accordance with some embodiments.
Figure 17B:
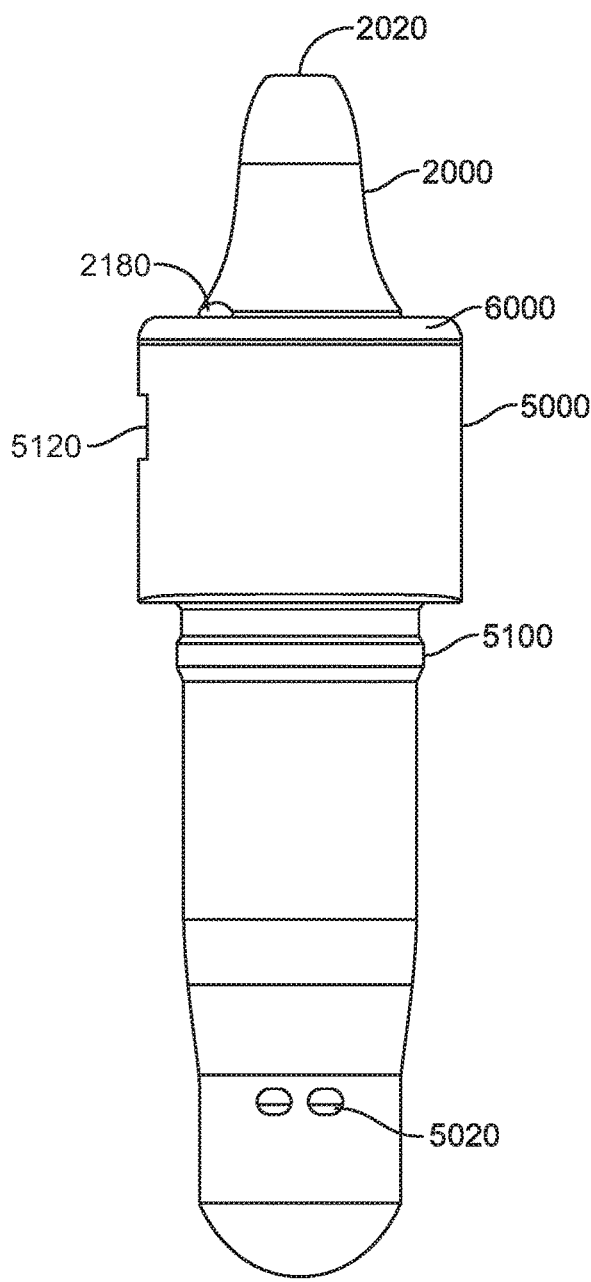

FIG. 17A and FIG. 17B illustrate a slice view and an exterior view, respectively, of a nozzle assembly, in accordance with some embodiments. A nozzle 2000 may translate as a piston within reservoir interface 5000. In some cases, a nozzle 2000 and reservoir interface 5000 may comprise portions of a nozzle assembly which may be removable from a reservoir in order to fill a reservoir. In some cases, once a reservoir interface 5000 is attached to a nozzle 2000, it may not be removed. Reservoir interface 5000 may also comprise one or more apertures 5020. In some case, an exterior of the reservoir interface 5000 may comprise an alignment feature 5120 to aid in assembly of the device, e.g. rotation and/or translation of reservoir interface 5000 relative to reservoir 1000.

FIG. 17A also illustrates a filter 2800 within nozzle cap 2500. In some cases, a nozzle cap may comprise a filter 2800. A filter may comprise a mesh or a screen. A filter may comprise a polyester mesh. A filter may comprise a paper mesh. A filter 2800 may be disposed within nozzle cap 2500. A filter may be disposed adjacent a nozzle cap 2500. A filter may comprise a mesh size of about 25 microns. A filter may comprise a mesh size of at least about 1 micron, at least about 2 microns, at least about 5 microns, at least about 10 microns, at least about 20 microns, at least about 50 microns, at least about 100 microns or more. A filter may comprise a mesh size of at most about 1 mm, at most about 500 microns, at most about 250 microns, at most about 100 microns, at most about 50 microns, at most about 25 microns, or less. A filter may comprise a mesh size of between about 1 and about 50 microns, between about 10 and about 50 microns, between about 1 and about 30 microns, between about 20 and about 30 microns, etc.

Figure 18A:
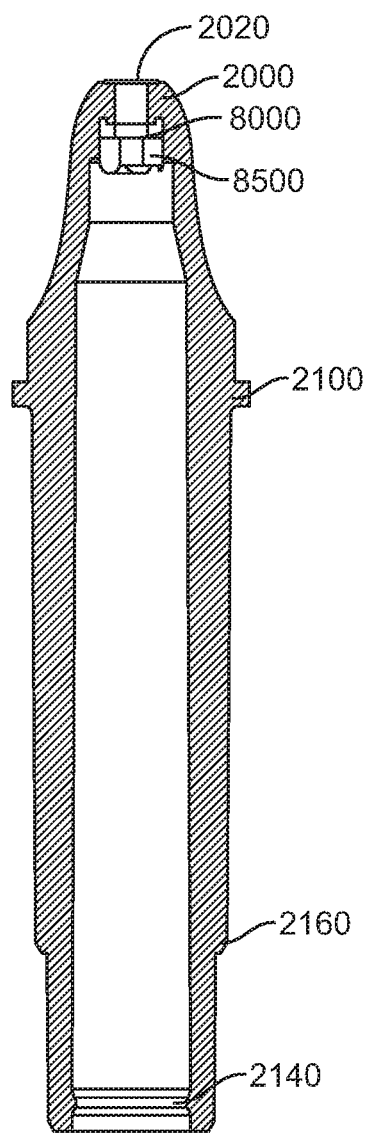
FIG. 18A, FIG. 18B illustrate a slice view and an exterior view, respectively, of a nozzle of the flow control device of FIG. 14, in accordance with some embodiments.
Figure 18B:
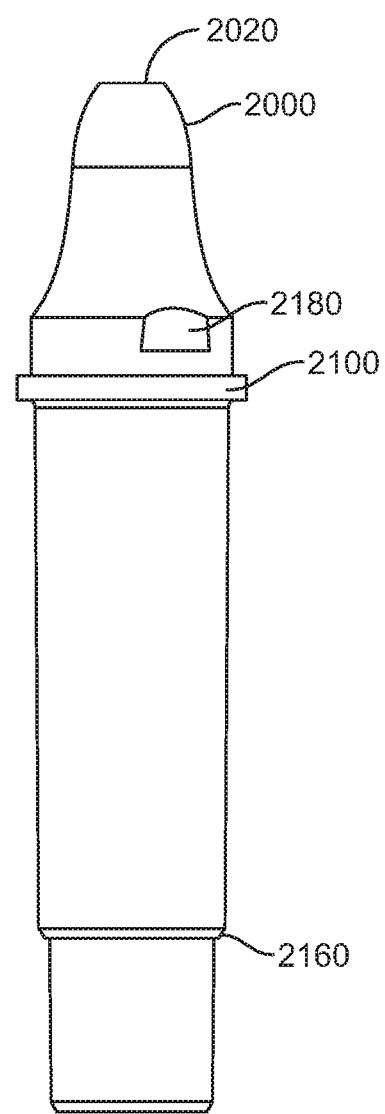

FIG. 18A and FIG. 18B illustrate a slice view and an exterior view, respectively, of a nozzle 2000, in accordance with some embodiments. The flow control device may comprise a nozzle 2000. The nozzle may comprise at least one outlet 2020. In some embodiments, the nozzle 2000 may comprise one or more retention features on an exterior surface of the nozzle. The retention features 2100 may abut a spring 7000 which may in turn abut shelf 5020 of the reservoir interface 5000. In some cases, the nozzle may be removable. The nozzle may be removable with a nozzle cap in place. In some cases, an exterior of nozzle 2000 may comprise an alignment feature 2180 to aid in assembly of the device, e.g. rotation and/or translation of nozzle 2000 relative to reservoir interface 5000.

The nozzle 2000 may comprise an interior volume, which interior volume may comprise a preservative removing device. A preservative removing device may comprise any example of a preservative removing device as disclosed herein, for example, the preservative removal agent and matrices as disclosed in the section "Preservative Removal Agent" elsewhere herein. A nozzle may comprise an interior volume of about 0.5 cc. A nozzle may comprise an interior volume of about 0.1 cc. A nozzle may comprise an interior volume of about 1 cc. A nozzle may comprise an interior volume of at least about 0.05 cubic centimeters (cc), at least about 0.1 cc, at least about 0.2 cc, at least about 0.3 cc, at least about 0.4 cc, at least about 0.5 cc, at least about 0.6 cc, at least about 0.7 cc, at least about 0.8 cc, at least about 1 cc, at least about 1.5 cc, at least about 2 cc, at least about 5 cc, or more. A reservoir may comprise an interior volume between about 0.01 cc and about 5 cc, between about 0.1 cc and about 5 cc, between about 0.5 cc and about 1.5 cc, between about 0.5 cc and about 5 cc, etc.

In some cases, a preservative removing device may at least partially fill an interior volume of a nozzle. For example, a preservative removing device may comprise a polymeric matrix. A preservative removing device may fill at least about 1%, at least about 2%, at least about 5%, at least about 10%, at least about 20%, at least about 50%, at least about 70%, at least about 80%, at least about 90%, at least about 95%, or more of an interior volume of the nozzle. A preservative removing device may fill between about 1% and about 99%, about 10% and about 98%, about 25% and about 50%, about 10% and about 50%, etc. of an interior volume of the nozzle.

The nozzle 2000 may comprise and outlet 2020. The outlet may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The outlet may comprise an aperture diameter of between about 10 and about 5000 microns, between about 10 and about 2500 microns, between about 10 and about 1000 microns, between about 10 and about 500 microns, etc.

Also illustrated in FIG. 18A is outlet filter 8000. A filter may comprise a mesh or a screen. A filter may comprise a polyester mesh. A filter may comprise a paper mesh. A filter 8000 may be disposed within outlet cap 8500. A filter may be disposed adjacent outlet cap 8500. A filter may comprise a mesh size of about 25 microns. A filter may comprise a mesh size of at least about 1 micron, at least about 2 microns, at least about 5 microns, at least about 10 microns, at least about 20 microns, at least about 50 microns, at least about 100 microns or more. A filter may comprise a mesh size of at most about 1 mm, at most about 500 microns, at most about 250 microns, at most about 100 microns, at most about 50 microns, at most about 25 microns, or less. A filter may comprise a mesh size of between about 1 and about 50 microns, between about 10 and about 50 microns, between about 1 and about 30 microns, between about 20 and about 30 microns, etc.

Outlet filter 8000 may be held in place by outlet cap 8500. In some cases, the outlet cap 250 is rotationally fixed relative to the nozzle 2000. In some cases, the outlet cap is rotationally fixed relative to the nozzle by one or more retention features. The retention features may comprise a snap fit, an interference fit, a press fit, a screw, etc. Rotational fixation of the outlet cap may be aided by a glue, a weld, a heat seal, etc. In some cases, the outlet cap may be removable. The outlet cap may aid in retention of a preservative removing device within an interior volume of the nozzle. In some cases, outlet cap 8500 may be insert molded into a nozzle.

Figure 19A:
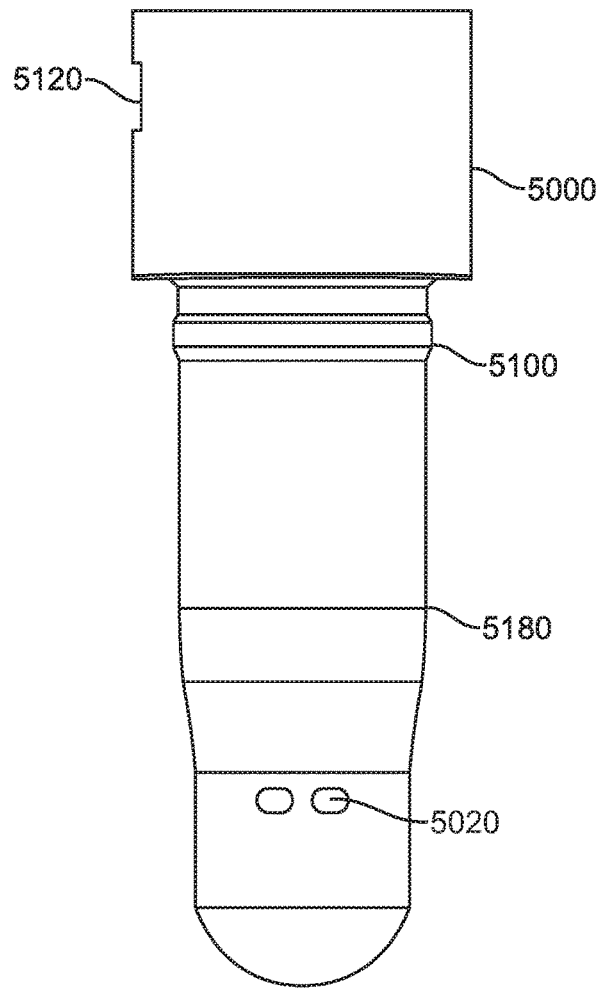
FIG. 19A, FIG. 19B illustrate exterior and slice views, respectively, of a reservoir interface of the flow control device of FIG. 14, in accordance with some embodiments.
Figure 19B:
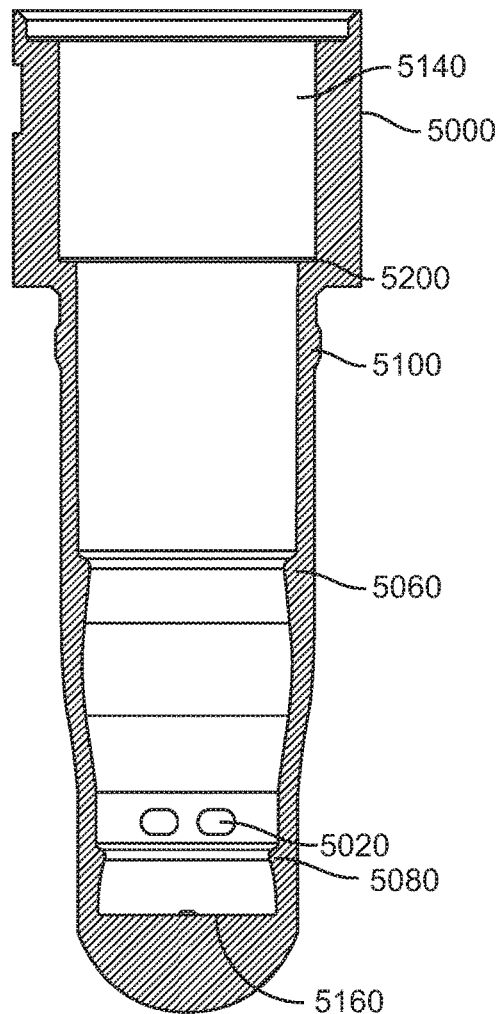

FIG. 19A and FIG. 19B illustrate exterior and slice views, respectively, of a reservoir interface 5000, in accordance with some embodiments. A described herein, a nozzle 2000 may translate as a piston within reservoir interface 5000. Reservoir interface 5000 may comprise bead seal elements 5080, and 5060. Reservoir interface 5000 may also comprise one or more apertures 5020. In some cases, an exterior of the reservoir interface 5000 may comprise an alignment feature 5120 to aid in assembly of the device, e.g. rotation and/or translation of reservoir interface 5000 relative to reservoir 1000.

As described herein, the nozzle assembly may comprise a bead seal configuration. When a cap 3000 is in place a nozzle 2000 may slide along axis of translation 4500 compressing spring element 7000. In some cases, when a cap is fully in place bead seal elements 2160 on a reservoir interface-facing surface of the nozzle are in contact with a nozzle-facing wall of the reservoir interface 5000. In some cases, when a cap is fully in place bead seal elements 5060, 5080 on a nozzle-facing surface of the reservoir interface are in contact with a reservoir interface-facing wall of the nozzle 2000. The bead seal elements 2160 and 5060, 5080 may comprise a fluidic seal. In some case, a fluidic seal may comprise contact between a bottom surface of nozzle cap 2500 and surface 5160 of reservoir interface 5000. The reservoir interface 5000 may comprise one or more retention features 5100 and 5180.

The reservoir interface may comprise one or more apertures 5020. The one or more apertures in the reservoir interface may fluidically connect an interior of the reservoir with an exterior of the reservoir. The one or more aperture may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

Figure 20:
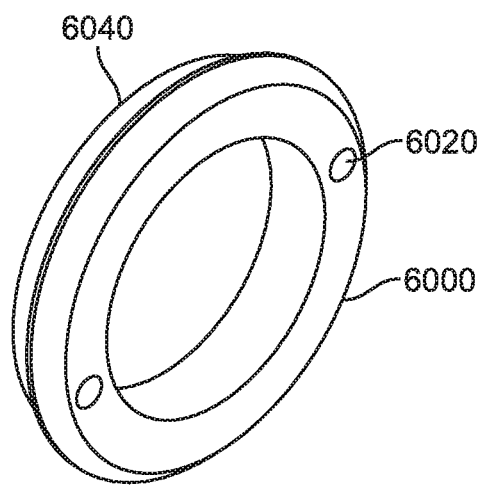
FIG. 20 illustrates an isomorphic view of a nozzle interface of the flow control device of FIG. 14, in accordance with some embodiments.

FIG. 20 illustrates an isomorphic view of a nozzle interface 6000, in accordance with some embodiments. Nozzle interface 6000 may comprise a retention ring. Nozzle interface 6000 may secure nozzle 2000 within reservoir interface 5000. Nozzle interface 6000 may comprise a mating surface 6040. Nozzle interface 6000 may be ultrasonically welded, heat sealed, glued, or bonded to reservoir interface 5000 at mating surface 6040. In some cases, nozzle interface 6000 may be removable. In some cases, nozzle interface 6000 may comprise a thread, a snap fit, a press fit, etc. In some case, an exterior of the nozzle interface 6000 may comprise an alignment feature 6020 to aid in assembly of the device, e.g. rotation and/or translation of nozzle interface 6000 relative to reservoir interface 5000.

Figure 21:
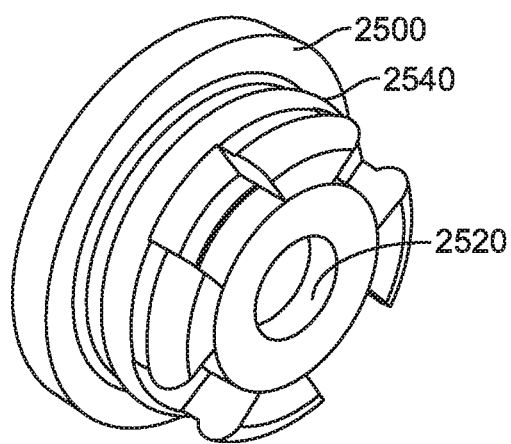
FIG. 21 illustrates an isomorphic view of a nozzle cap of the flow control device of FIG. 14, in accordance with some embodiments.

FIG. 21 illustrates an isomorphic view of a nozzle cap 2500, in accordance with some embodiments. The nozzle cap 2500 may comprise one or more apertures 2520. The one or more apertures in the nozzle cap may fluidically connect to an interior of the nozzle 2000 which may be fluidically connected to the outlet 2020 and an exterior of the nozzle. The one or more apertures in the nozzle cap may fluidically connect to a reservoir interface-facing surface of the nozzle. The one or more aperture may comprise at least 1 aperture, at least 2 apertures, at least about 5 apertures, at least about 10 apertures, at least about 20 apertures, at least about 50 apertures, at least about 100 apertures, or more. In some cases, the one or more apertures comprises the openings of a filter. The one or more apertures may comprise a number of apertures within a range from about 1 to about 100, from about 1 to about 50, from about 1 to about 10, from about 5 to about 100, from about 10 to about 100, from about 2 to about 20, etc.

The one or more apertures may comprise a diameter of at least about 1 micron, at least about 2 microns, at least about 5 microns, at least about 10 microns, at least about 20 microns, at least about 50 microns, at least about 100 microns, at least about 500 microns, at least about 1 mm, at least about 2 mm, at least about 5 mm, at least about 10 mm, or more. The one or more apertures may comprise an aperture diameter of between about 10 and about 5000 microns, between about 10 and about 2500 microns, between about 10 and about 1000 microns, between about 10 and about 500 microns, etc.

In some cases, the nozzle cap 2500 is rotationally fixed relative to the nozzle 2000. In some cases, the nozzle cap is rotationally fixed relative to the nozzle by one or more retention features 2540. The retention features 2540 may comprise a snap fit, an interference fit, a press fit, a screw, etc. Rotational fixation of the nozzle cap may be aided by a glue, a weld, a heat seal, etc. In some cases, the nozzle cap may be removable. The nozzle cap may aid in retention of a preservative removing device within an interior volume of the nozzle.

Figure 22A:
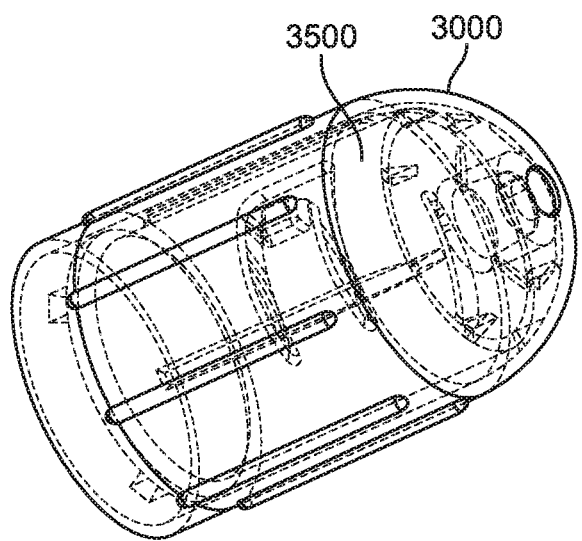
FIG. 22A, FIG. 22B, FIG. 22C show a cap of the flow control device of FIG. 14, in accordance with some embodiments
Figure 22B:
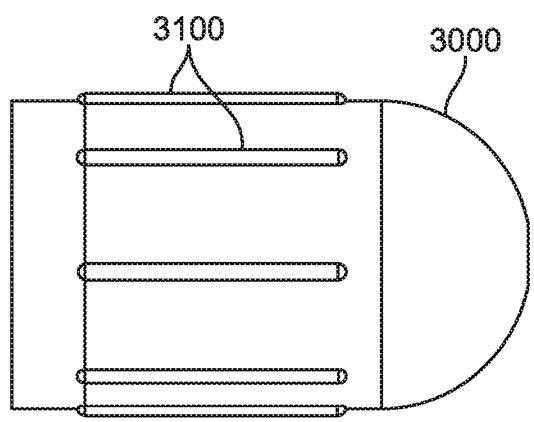
Figure 22C:
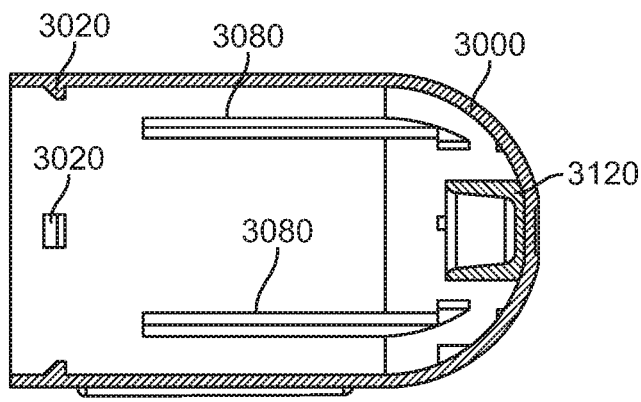

FIG. 22A, FIG. 22B, FIG. 22C, FIG. 23A, FIG. 23B, and FIG. 23C show cap 3000, in accordance with some embodiments. Cap 3000 may comprise an interior cap 3500. FIG. 22A shows an isomorphic view of cap 3000. The exterior portion of cap 3000 is transparent and interior cap 3500 is solid. Cap 3000 may comprise a spring element 3540 which may create an audible and/or tactile click when a cap is in place. FIG. 22B shows an exterior view of cap 3000. The exterior may comprise exterior features 3100 which may aid in removing or applying the cap. In some cases, cap 3000 comprises a closure assembly which is resistant to manipulation from a child. In some cases, cap 3000 produces an audible or tactile click when moved into a closed state. FIG. 22C shows a slice view of an exterior portion of cap 3000. Cap 3000 may comprise retention elements 3020 which may retain interior cap 3500. Retention elements 3020 may be shaped to allow the cap portions to slide together but may resist being removed from one another. Cap 3000 may comprise click elements 3080 which may create a stop for a spring element 3540, thereby creating a click. Cap 3000 may comprise seal cap 3120 which may receive an outlet extension. When seal cap 3120 receives an outlet extension, outlet 2020 may sealed. Seal cap 3120 may provide an air tight and/or water tight seal. One or membranes or coatings may be deposited inside of the seal cap to aid in a quality of a seal.

Figure 23A:
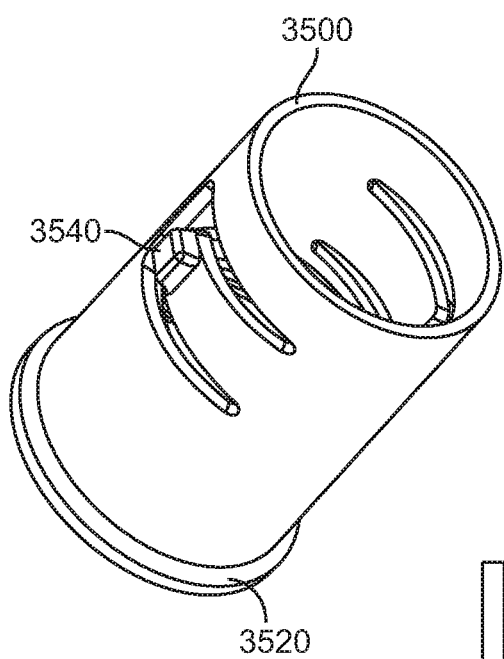
FIG. 23A, FIG. 23B, and FIG. 23C show an interior cap of the flow control device of FIG. 14, in accordance with some embodiments
Figure 23B:
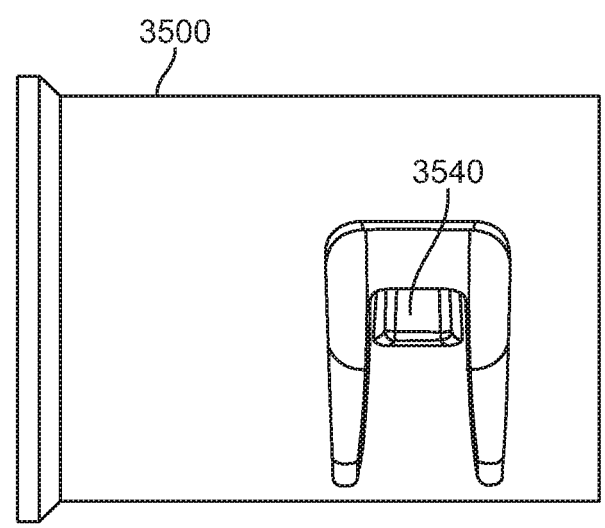
Figure 23C:
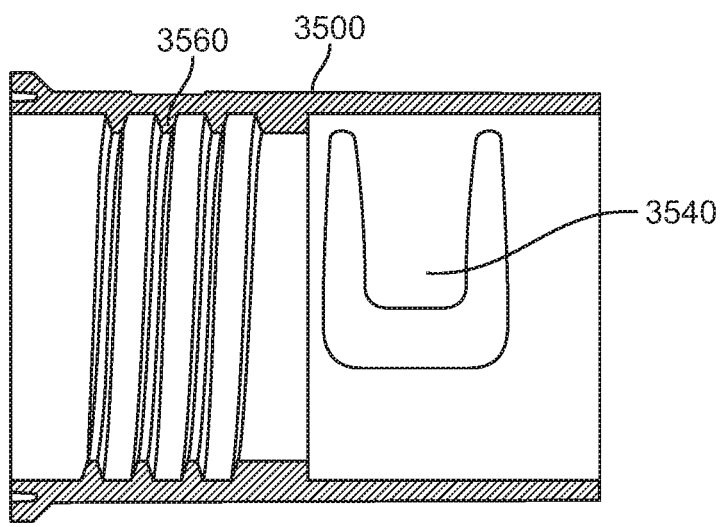
Figure 24A:
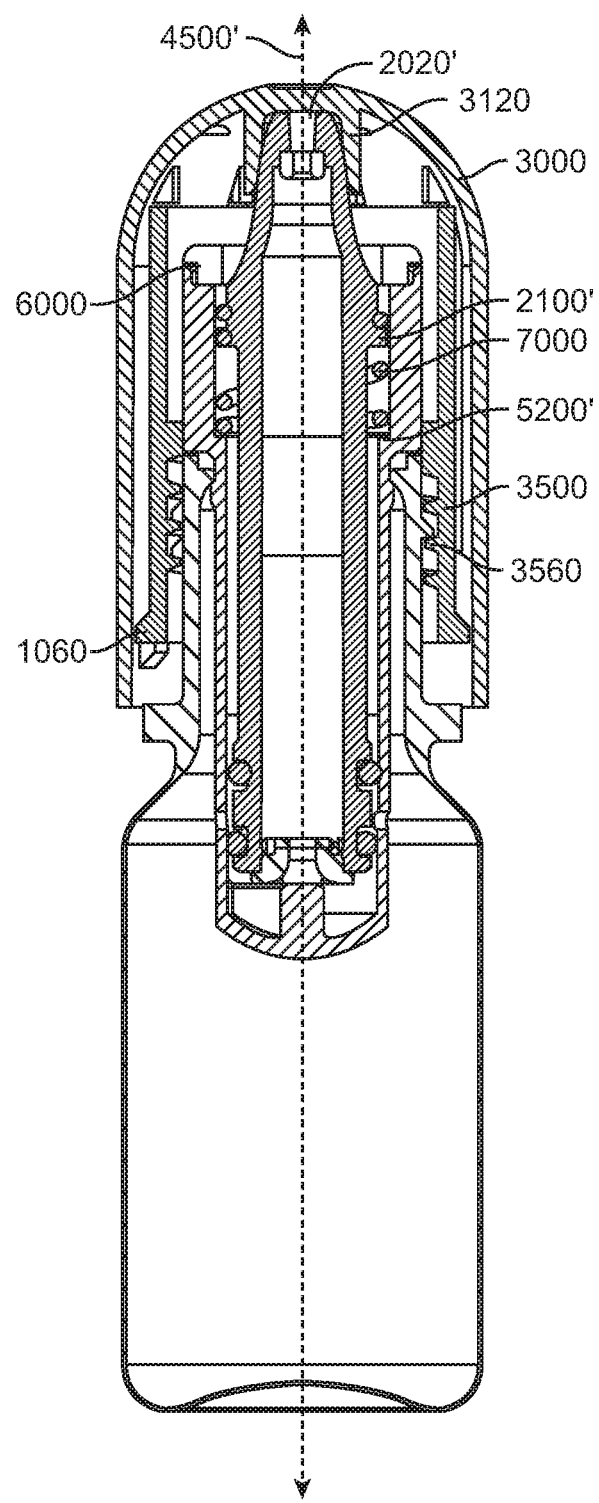
FIG. 24A and FIG. 24B illustrate a variation on the nozzle design of FIG. 14 comprising an o-ring seal, in accordance with some embodiments.
Figure 24B:
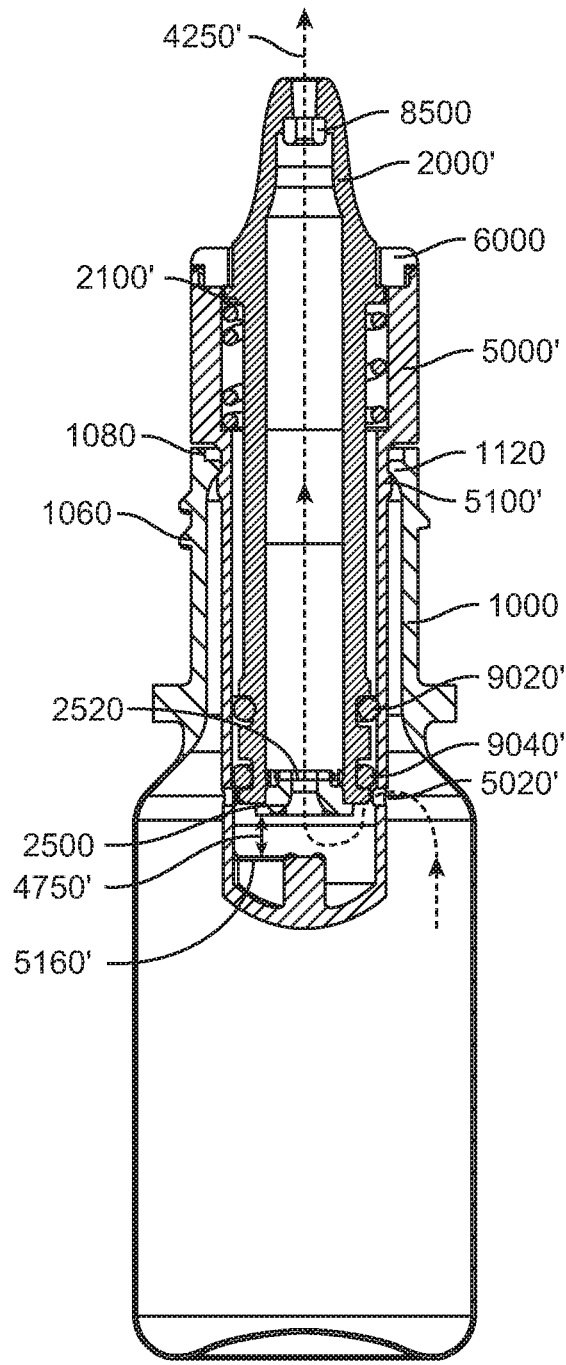

FIG. 23A, FIG. 23B, and FIG. 23C illustrate interior views of interior cap 3500, in accordance with some embodiments. FIG. 23A illustrates an isomorphic view of interior cap 3500. Interior cap 3500 may comprise spring element 3540 and ridge 3520. Spring element 3540 may create a click when it traverses click element 3080. Ridge 3520 may reinforce a lower wall of the interior cap, which may help prevent separation of the interior and exterior portions of cap 3000. FIG. 3B and FIG. 3C illustrate an exterior view and a slice view respectively of interior cap 3500. Interior cap 3500 may comprise threads 3560 which may interface with threads 1060 of a reservoir 1000.

FIG. 24A and FIG. 24B illustrate a variation on the nozzle design of FIG. 14 are illustrated in FIG. 15A, FIG. 15B, FIG. 16A, FIG. 16B, FIG. 17A, FIG. 17B, FIG. 18A, FIG. 18B, FIG. 19A, FIG. 19B, FIG. 20, FIG. 21, FIG. 22A, FIG. 22B, FIG. 22C, FIG. 23A, FIG. 23B, and FIG. 23C. Whereas the flow control device of FIGS. 14-23C show a bead seal design, the device of FIG. 24A and FIG. 24B comprises an o-ring seal. Reservoir interface 5000' and nozzle 2000' of the o-ring seal design may distinct from the bead seal design, while the other elements may remain substantially the same from the bead seal design. Like reference numbers refer to like elements.

The nozzle assembly may comprise o-ring seal configuration. Nozzle 2000' may slide within reservoir interface 5000' along an axis of translation 4500'. Translation of the nozzle may prevent flow of the ophthalmic formulation between the interior of the nozzle and the reservoir, thereby stabilizing a concentration of the preservative in the ophthalmic formulation. An o-ring seal may have additional parts; however, an o-ring seal may provide a more reliable seal and/or may absorb issues with manufacturing tolerances. A bead seal may comprise fewer parts and/or may be easier to manufacture.

As shown, when a cap 3000 is in place a nozzle 2000' may slide along axis of translation 4500' compressing spring element 7000. In some cases, when a cap is fully in place o-rings 9020' and 9040' may contact a reservoir interface-facing surface of the nozzle 2000' and contact a nozzle-facing wall of the reservoir interface 5000'. The o-rings 9020' and 9040' may comprise a fluidic seal. The o-rings may comprise a natural rubber, a synthetic rubber, an elastomeric polymer, PTFE, Nitrile (Buna), Neoprene, EPDM Rubber and Fluorocarbon (Viton), etc.

A translation distance 4750' is illustrated in FIG. 24B. In some cases, surface 5160' may comprise a first translation stop. In some cases, threads of cap 3000 may comprise a first translation stop. A second translation stop may comprise an interaction between outlet 2020' and a seal cap 3120 of cap 3000. A second translation stop may comprise an interaction between retention features 2100' on a reservoir seal-facing surface of nozzle 2000' with nozzle interface 6000. Nozzle interface 6000 may comprise a retention ring. Nozzle interface 6000 may be ultrasonically welded, heat sealed, glued, or bonded to reservoir interface 5000'. In some cases, nozzle interface 6000 may be removable. In some cases, nozzle interface 6000 may comprise a thread, a snap fit, a press fit, etc. A spring element 7000 may be compressed between retention feature 2100' and a shelf 5200' of the reservoir interface.

Translation of the nozzle along the axis of translation 4500' relative to the reservoir may fluidically connect the one or more apertures 5020' in the reservoir interface 5000' with the one or more apertures in the nozzle cap 2520'. Looking at apertures 5020' and apertures 2520', in FIG. 24B, it is illustrated that both apertures are fluidically connected allowing for fluid passage between reservoir 1000 and nozzle 2000'. Looking at apertures 5020" and nozzle 2000, in FIG. 24A, it is illustrated that nozzle cap 2500 abuts a bottom surface 5160' of the reservoir interface, thereby impeding fluid passage between reservoir 1000 and nozzle 2000'. FIG. 24B illustrates flow path 4250' through the device.

FIG. 24B also illustrates an interaction between reservoir interface 5000' and reservoir 1000. The reservoir interface 5000' may comprise one or more retention features 5100'. The mouth of the reservoir may comprise one or more retention features 1120 which may receive the one or more retention features 5100' of the reservoir interface 5000'. When the reservoir interface is in place within a mouth of the reservoir, an orientation of the reservoir interface relative to the reservoir may be rotationally fixed. The retention features 5100' may comprise a snap fit, an interference fit, a press fit, a screw, etc. Rotational fixation of the reservoir interface may be aided by a glue, a weld, a heat seal, etc. In some cases, the reservoir interface may be removable. The reservoir interface 5000' may comprise a cavity in which a nozzle 2000' may translate.

In another aspect, the present disclosure provides a method of controlling a preservative concentration within an ophthalmic formulation. The method may comprise: receiving the bottle of any aspect or embodiment and rotating the nozzle or the bottle cap relative to the reservoir.

In another aspect, the present disclosure provides a method of fabricating the flow control device of aspect or embodiment. The method may comprise: filling the reservoir with the ophthalmic formulation; placing the reservoir interface on the reservoir; placing the nozzle cap on the nozzle; and placing the nozzle at the mouth of the reservoir. In some embodiments, the method further comprises placing a bottle cap on the nozzle. The method may comprise providing a preservative removing device within an interior volume of the nozzle. The preservative removing device may be formulated as a plug which partially fills the nozzle volume. In some cases, a preservative removing device may be filled as a liquid which may be solidified within the interior volume. In some cases, a preservative removing device may be a powder which is compressed within the interior volume.

In another aspect, the present disclosure provides methods of using a flow control device of any aspect or embodiment disclosed herein. A method of use may comprise removing a cap, allowing a flow control device to proceed to an open position, and applying a pressure to a compressible bottle to form a drop of an ophthalmic formulation. An ophthalmic formulation may comprise a reduced amount of a preservative. A method of use may further comprise forming subsequent drops of an ophthalmic formulation, wherein a concentration of a preservative within the reservoir is substantially unchanged. A concentration of a preservative may be substantially unchanged to within about 50%, to within about 10%, to within about 5%, to within about 1%, or less. A method of use may comprise providing the flow control device of any aspect or embodiment to a subject, wherein a concentration of a preservative within the reservoir is configured to be substantially unchanged over a plurality of instillations. A concentration of a preservative may be substantially unchanged to within about 50%, to within about 10%, to within about 5%, to within about 1%, or less. In some cases, the concentration of a preservative within the reservoir may be substantially unchanged to within about 50%, to within about 40%, to within about 30%, to within about 20%, to within about 15%, to within about 10%, to within about 9%, to within about 8%, to within about 7%, to within about 6%, to within about 5%, to within about 4%, to within about 3%, to within about 2%, to within about 1%, or less compared to an initial concentration after at least 5, at least 10, at least 15, at least 20, at least 30, at least 40, or at least 50 instillations, in accordance with the methods and apparatuses and devices disclosed herein.

In another aspect a kit comprising the flow control device of any aspect or embodiment and a packaging is provided. In some embodiments, the kit further comprises a label, wherein the label comprises an indication of a contents of the ophthalmic formulation disposed within the reservoir.

Preservative Removal Agent

The present disclosure provides a preservative removal agent (also referred to herein as a preservative removing device (e.g. a matrix)). A preservative removal agent may rapidly and selectively remove preservatives of the present disclosure from a solution, emulsion, or suspension comprising an ophthalmic agent. The preservative removal agent may rapidly and selectively extract the preservative, allowing the eye drop formulation to flow through the plug with minimal pressure drop, yet with sufficient time to remove the preservative and with sufficient surface area and chemistry to adsorb the preservative. The matrix may comprise a material with a high affinity for the preservative, such as, for example, benzalkonium chloride (BAK), and at the same time a low affinity for a drug or other ophthalmological agent especially when the drug is also in a complex with a capping agent. The preservative removal agent may be sufficiently selective, such that at least 50 percent of the preservative is removed and at least 50 percent of the drug is retained by the solution. BAK (benzalkonium chloride) can also go under a number of synonyms: alkylbenzyldimethylammonium chloride, alkyldimethylbenzylammonium chloride, benzyl ammonium chloride to name a few. It is also defined by a structure such as Formula: $C_6H_5CH_2N(CH_3)_2RCl$ ($R=C_8H_{17}$ to $C_{18}H_{37}$) with a CAS Number: 63449-41-2. For most purposes in ophthalmic applications and formulations PharmaGrade, EP, USP, JP, manufactured under appropriate GMP controls for pharma or biopharmaceutical production is used.

Non-limiting examples of a preservative removal agents may comprise solid, gel, and/or particulate matrices. The preservative removal agent may act as a physical barrier or filter. Additionally, or alternatively, the preservative removal agent may chemically remove a preservative such as by adsorption of the preservative onto the matrix. The preservative removal agent may be disposed in the outlet of a container, which container may contain the solution, emulsion, or suspension.

In some embodiments, a matrix disposed within a nozzle may be a porous polymeric matrix. The porous polymeric matrix may comprise a variety of materials. Such material may be safe and biocompatible. Such material may comprise but is not limited to, for example, Poly(2-hydroxyethyl methacrylate) (pHEMA), poly(hydroxylethyl methacrylate-co-methacrylic acid), crosslinked polyacrylamide, dimethyl acrylamide, methyl methacrylate, silicones, and/or any combination of the preceding materials.

In some embodiments, the matrix may be highly porous. The pore size in the matrix may be small enough so that the molecules, which may initially be far from the surface of the polymer in the matrix, may diffuse towards the polymer and adsorb. A matrix may have large interconnected pores which may allow flow of solution and adsorption of the preservative into the pores. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix may comprise a packed bed of pHEMA or crosslinked polyacrylamide or other polymeric particles. The particles may be macroporous. The particles may be spherical or non-spherical. In some embodiments, the polymeric matrix may comprise nano or micron sized polymeric particles (e.g., nanogels or microgels). In some embodiments, the polymeric matrix may comprise a cryogel. In some embodiments, the polymeric matrix may be termed a hydrogel, be hydrophilic and absorb water readily. In some embodiments, the particles themselves may directly impart the preservative effect, such as colloidal silver nanoparticles.

In certain embodiments, particles of the formulations described herein have an average diameter from about 1 nm to about 10 μm, about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, greater than 80% of the particles, such as greater than 90% or greater than 95% of the particles in the formulation have an average largest particle diameter of from about 1 nm to about 1000 μm, about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700 nm, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, particles of the porous polymeric matrix described herein have an average diameter from about 100 nm to about 10 μm, about 100 nm to about 10 μm, about 100 nm to about 5 μm, about 100 nm to about 2 μm, about 100 nm to about 1 μm, about 100 nm to about 900 nm, about 100 nm to about 800 nm, about 100 nm to about 700, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80% of the particles of the porous polymeric matrix, greater than 90% of the particles of the porous polymeric matrix, or greater than 95% of the particles of the porous polymeric matrix have an average diameter from about 100 nm to about 10 μm, about 100 nm to about 10 μm, about 100 nm to about 5 μm, about 100 nm to about 2 μm, about 100 nm to about 1 μm, about 100 nm to about 900 nm, about 100 nm to about 800 nm, about 100 nm to about 700, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80% of the particles of the porous polymeric matrix, greater than 90% of the particles of the porous polymeric matrix, or greater than 95% of the particles in the formulation have an average diameter from about 10 μm to about 100 μm, about 50 μm to about 200 μm, about 90 μm to about 180 μm, about 150 μm to about 250 μm, about 200 μm to about 350 μm about 250 μm to about 500 μm, about 350 μm to about 800 μm, about 500 μm to about 1000 μm In certain embodiments, the average diameter is the average largest diameter or the average equivalent diameter. The particles may be irregular, regular, spherical, ovoid, or generally of any shape and the size can be defined as passing through a certain sized screen sieve.

The matrix may comprise a tortuosity such that the flow path of a solution, emulsion, or suspension through the nozzle may be significantly increased. In an embodiment where the matrix is a packed bed of macroporous particles, the packed beds of macroporous particles may have three levels of porosity: the space between the particles, the macropores in the particles, and the inherent porosity of the polymer. In such an embodiment, all three levels of porosity may contribute to the tortuosity of the matrix.

In some embodiments, a matrix disposed within a nozzle may be a porous polymeric matrix. Applying a pressure behind the nozzle may cause fluid to flow through the nozzle via the flow path, along which path the preservative may be removed by adsorption onto the matrix. The polymer material, the hydraulic permeability, the partition coefficient, the adsorption rate, and the pore size in combination may aid in the absorption of all or most of the preservative from the solution and thus patient eye drops. The reduced preservative solution may subsequently be delivered directly to the eye. The porous polymeric matrix may rapidly and selectively extract the preservative, allowing the eye drop formulation to flow through the plug with minimal pressure drop, yet with sufficient time to remove the preservative and with sufficient surface area to adsorb the preservative. The matrix may comprise a material with a high affinity for the preservative, such as for example benzalkonium chloride (BAK), and low affinity for a drug or other ophthalmological agent. The porous polymeric matrix may comprise a high affinity for the preservative, such that at least 50 percent of the preservative may be removed and at least 50 percent of the drug may be retained by the solution. In some cases, the methods and devices disclosed herein are configured to remove at least 50%, at least 60%, at least 70%, at least 80%, at least 90%, at least 95%, at least 96%, at least 97%, at least 98%, or at least 99% or more of the preservative, while also retaining at least 50%, at least 60%, at least 70%, at least 80%, at least 90%, at least 95%, at least 96%, at least 97%, at least 98%, or at least 99% or more of the drug during instillation or delivery of the eye drop formulation.

The porous polymeric matrix may comprise a variety of materials. Such materials may be safe and biocompatible. A polymer of the present disclosure may comprise various monomers, for example, Poly(2-hydroxyethyl methacrylate) (pHEMA) and/or and/or acrylamide (AM), dimethyl acrylamide (DMA) and/or methyl methacrylate (MMA) and/or N-Vinylpyrrolidone (NVP) and/or 2-acrylamido-2-methyl-propane sulfonic acid (AMPS) and/or polyvinyl alcohol (PVA) and/or polymethylpropane sulfonic acid (PAWS) and/or 2-sulfoethyl methacrylate (SEM) and/or acrylic acid (AA) and/or vinylphosphonic acid (VP) and/or t-butyl methacrylate (TBM) and/or Methacryloxypropyltris(trimethylsiloxy)silane (TRIS) and/or t-amyl methacrylate and/or n-octyl methacrylate and/or iso-decyl methacrylate and/or n-decyl methacrylate and/or n-dodecyl acrylate and/or n-hexyl acrylate and/or n-dodecyl acrylate and/or N-(n-Octadecyl)acrylamide and/or silicones and/or any combination of the preceding materials. The polymeric matrix may further comprise a cross linker. A crosslinker may comprise N,N'-methylenebis(acrylamide) (MBAM) and/or triacrylamido triazine (TATZ) and/or SR 351 and/or SR9035 and/or any combination of the preceding materials.

In some embodiments, the matrix material is a copolymer. A copolymer may comprise more than one species of monomer. Copolymers may be branched. Copolymers may be linear. Copolymers may comprise crosslinkers. Copolymers may be block copolymers, may be alternating copolymers, may be periodic copolymers, may be gradient copolymers may be statistical copolymers, may be stereoblock copolymers. The copolymers may exhibit phases of differing hydrophobicity or hydrophilicity. The hydrophobicity and/or hydrophilicity of the one or more monomers or cross-linkers may control the binding of a therapeutic agent or a preservative to the plug material.

In some embodiments, the polymeric matrix is polyvinyl alcohol crosslinked with citric acid or other suitable crosslinking agent to render it a hydrophilic hydrogel. In some embodiments, the polymeric matrix is crosslinked polyvinylpyrrolidone, crosslinked polyethylene oxide, crosslinked polyacrylamides, crosslinked copolymers of methacrylic acid, polyacrylic acid and copolymers such as poly (acrylic acid-co-acrylamide), or poly (methacrylic acid-co-acrylamide).

Polymers of the present disclosure may generally follow an A/B/C formula where A and B are monomers, C is one or more cross-linkers, and A and B are not the same monomer. In some examples, A may be an anionic hydrophilic monomer. In an A/B/C formula, monomers of type A may comprise AM or NVP. In some examples, B may be an ionic hydrophilic monomer. In an A/B/C formula, monomers of type B may comprise MAA, AMPS, SEM, AA, or VP. In some examples, C may be a crosslinker. In an A/B/C formula, monomers of type C may comprise one or more of MBAM, TATZ, or SR 351. Polymers of the present disclosure may generally follow an A/C formula where A is a monomer as described above and C is one or more cross-linkers as described above. Polymers of the present disclosure may generally follow a B/C formula where B is a monomer as described above and C is one or more cross-linkers as described above.

Polymers of the present disclosure may also comprise grafted copolymers such that components such as monomer A and with a cross-linker C are first copolymerized to form a crosslinked copolymer that can be isolated as a small bead or other shaped particle. These beads or particles can then be reswollen in water and a monomer of B type can added and then polymerized into or onto the bead or particle through the use a free radical "grafting" polymerization. In this embodiment the particles are made up of A/C copolymer with a "grafted" B polymer as part of the copolymer structure.

The following is a non-exhaustive list of examples of polymers of the present disclosure. The following includes polymer components and percent compositions, separated by slashes, respectively, and an identifier corresponding to an example polymer in the following list. Polymers of the present disclosure may comprise: AMPS/MBAM/TATZ 7.5/82.5/10 (D-322-018-AW), AMPS/MBAM/TATZ 7.5/77.5/15 (D-322-020-AW), AMPS/MBAM 7.5/92.5 (D-322-022-AW), BioRad Beads /AMPS 1 g/0.5 (D-322-028-C-AW), AMPS/MBAM 7.5/92.5 (D-322-002-AG-W), AMPS/MBAM/TATZ 7.5/87.5/5.0 (D-322-006-AW), SEM/MBAM 7.5/92.5 (D-322-010-AW), AM/2-Sulfoethyl MA(SEM)/MBAM 30/10/60 (D-298-132-A), AMPS/MBAM 7.5/92.5 (D-298-190-AW); AMPS/MBAM 7.5/92.5 (D-298-196-A), AMPS/MBAM 7.5/92.5 (D-298-196-AW), AMPS/MBAM 7.5/92.5 (D-298-178-AW), PVA/PAMPS/CA 4.8/1.2/2.4 IPN (D-298-182-A), AMPS/MBAM 7.5/92.5 ISP (D-298-184-AW), NVP/AMPS/MBAM/TATZ 30/10/30/30 (D-298-186-A), AMPS/MBAM 7.5/92.5 (D-298-152-AW), N-vinylpyrrolidinone/AMPS/MBAM 30/10/60 (D-298-120-AW), AA/SR351 40/60 (D-298-146-A), AA/MBAM/SR351 60/30/10 (D-298-148-A), AM/2-Sulfoethyl MA (SEM)/MBAM 15/25/60 (D-298-134-A), AA/MBAM 40/60 (D-298-140-A), AA/MBAM 50/50 (D-298-142-A), and VP/AA/MBAM 10/45/45 (D-298-144-A).

Any matrix material and any drug in association with a complexing agent may be used such that the drug/complex partition coefficient into the matrix may be lower by at least an order of magnitude or 2 orders of magnitude than the matrix's affinity for the preservative. For example, pHEMA, or SO3— or PO3H— or COO— groups on the polymer (or matrix) may bind BAK with a partition coefficient of about 100-500, or in some embodiments, 1000 depending on the BAK concentration and the structure of the matrix and the % content of those groups. In some embodiments, the matrix may comprise a partition coefficient for the preservative from the solution, emulsion, or suspension of, for example, at least 10, at least 50, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10,000, or within a range defined by any two of the preceding values. Additionally, or alternatively, the adsorption rate constant may be sufficiently high so that the time for adsorption of a drug molecule to the polymer may be less than the time to form a drop. The time to form a drop may comprise a time within a range from 0.1 to 10 seconds.

The matrix may display a high hydraulic permeability such that relatively little pressure may be required to dispense a fluid. The hydraulic permeability may depend on the design of the filter. Larger pores in the matrix may allow for higher flow for a given pressure drop. In some embodiments, hydraulic permeability may be larger than about 0.01 Darcy. A nozzle may comprise a permeability of about 0.1 Darcy. A hydraulic permeability of 1 to 10 Darcy may allow fluid to be retained in the filter during instances when the pressure may be lowered subsequent to formation of a drop. A larger hydraulic permeability may allow the same plug to work for a wide range of formulations including, for example, high viscosity formulations, such as rewetting eye drops. In some embodiments, the porous polymeric matrix comprises a hydraulic permeability of, for example, 0.01 Da, 0.1 Da, 1 Da, 10 Da, 100 Da, 1000 Da or a hydraulic permeability within a range defined by any two of the preceding values.

In some embodiments, the matrix may be highly porous. The pore size in the matrix may be small enough so that the molecules, which may initially be far from the surface of the polymer in the matrix, may diffuse towards the polymer and adsorb. A matrix may comprise large interconnected pores which may allow flow of solution and adsorption of the preservative into the pores. The matrix may be formed as a porous gel, as a packed bed, and/or a structure formed by 3D printing soft lithography, electrospinning of a fiber, or any other appropriate method. In some embodiments, the matrix may comprise a microporous gel. In some embodiments, the matrix may comprise a packed bed of pHEMA or cross-linked polyacrylamide with an anionic moiety or functionality as part of the polymer or other polymeric particles. The particles may be macroporous. The particles may be spherical or non-spherical. In some embodiments, the polymeric matrix may comprise nano or micron sized or 10s of microns or 100s of microns of polymeric particles (e.g., nanogels or microgels). In some embodiments, the polymeric matrix may comprise a cryogel. In some embodiments, the particles themselves may directly impart the preservative effect, such as colloidal silver nanoparticles.

In some embodiments, the particles may need to be stably held in the nozzle and prevented from eluting from the nozzle. The particles may be attached to the container walls through long polymeric chains and/or by placing a filter at the exit from the device. Additionally, or alternatively, the walls of the container or other surfaces may comprise preservative attached thereupon and/or incorporated therein. In such embodiments, the preservative source comprises a pHEMA membrane with 1-10% by volume equilibrated with BAK. In some embodiments, the matrix comprises pre-loaded with BAK at a concentration to inhibit microbial growth over time.

In some embodiments, the porous matrix material may comprise a tortuosity such that the flow path of a solution, emulsion, or suspension through the nozzle increases. In some embodiments where the matrix comprises a packed bed of macroporous particles, the packed beds of macroporous particles may comprise three levels of porosity: the space between the particles, the macropores in the particles, and the inherent porosity of the polymer. In such embodiments, all three levels of porosity may contribute to the tortuosity of the matrix. The tortuosity of the porous material combined with the geometry nozzle itself may increase the flow path in accordance with a multiplicative factor of a first flow path length corresponding to flow defined by the nozzle geometry and a second flow path length corresponding to the tortuosity of the porous material.

The pressure needed for drop creation may exceed the Young Laplace pressure during drop creation, which may be about $2\sigma/R_d$ where $\sigma$ is the surface tension and $R_d$ is the radius of the drop. Estimating $R_d$~0.5 mm based on a drop volume of 30 microliter (µL), and using the surface tension of water may yield a Young Laplace pressure of about 100 Pa. The pressure to form a drop may additionally exceed the pressure needed to displace 30 µL of volume. Typical drop volumes may comprise a volume within a range between 1 µL and 100 µL. The minimum pressure to form a drop may be ~0.01 Atm (1000 Pa) based on an ideal gas estimate using a 3 mL bottle at atmospheric pressure but may be lower for larger bottles at varying pressures. Maximum pressure to form a drop may be limited by a patient strength. The pressure to form a drop may be within a range between 0.01 Atm and 0.5 Atm.

The rate of liquid flow through the plug may depend on the applied pressure as well as the design parameters of the matrix including, but not limited to, length, area, porosity, hydraulic permeability, flow path length, etc. These design parameters may be considered individually or in combination to remove preservative without excessive squeeze pressure. The rate of liquid flow may affect the time to form a drop.

Solution, Emulsion, or Suspension

Provided herein are ophthalmic formulations comprising an ophthalmic agent, a complexing agent, and a preservative. In some embodiments, ophthalmic formulations provided herein are solutions, emulsions, and/or suspensions of an ophthalmic agent, a complexing agent, and a preservative. In some embodiments, provided herein are compositions comprising a therapeutically effective amount of any ophthalmic therapeutic compound, or salt of any one of the preservatives, ophthalmic agents, and/or complexing agents of the present disclosure. In some embodiments, a solution, emulsion, or suspension may be used in any of the methods described herein. The solution, emulsion, or suspension may additionally comprise one or more pharmaceutically acceptable excipients.

In some embodiments, a composition of complexing agent, therapeutic agent, and/or a preservative may be used for the treatment of a therapeutic disorder such as, dry eye, bacterial infection, glaucoma, hypertension, inflammation, allergic conjunctivitis, hypotrichosis of the eyelashes, fungal infection, etc. Additionally, or alternatively, a composition of a preservative, therapeutic agent, and/or a complexing agent may be used during a preventative, diagnostic, or therapeutic ophthalmological procedure, for example, local anesthetic, pupil dilation, etc. A solution, emulsion, or suspension administered to the eye may be administered topically, for example, with an eye drop. In some embodiments, the compounds, or salts thereof, of the disclosure with low aqueous solubility may be formulated as aqueous suspensions.

Ophthalmic Agent

Embodiments of the present disclosure may provide an ophthalmic agent for delivery to an eye. The ophthalmic agent may be a therapeutic agent. The therapeutic agent may comprise one or more ophthalmic agents. In some embodiments, the disclosure provides solutions, emulsions, or suspensions of a preservative, a complexing agent, and an ophthalmic agent. In some embodiments, the solutions, emulsions, or suspension may comprise a preservative removal agent, (e.g. in embodiments where the preservative removal agent may comprise a portion of a solution, emulsion, or suspension comprising an ophthalmic agent and a preservative). In other embodiments, the preservative removal agent may be separate from the solution, emulsion, or suspension comprising the ophthalmic agent, the complexing agent, and the preservative (e.g. in embodiments where the preservative removal agent may be located within the neck of a bottle). Ophthalmic agents may comprise compounds and salts, for use in the treatment of ophthalmic diseases. Optionally, in any embodiment, the solution, emulsion, or suspension may additionally comprise one or more pharmaceutically acceptable excipients. The disclosed compounds and salts can be used, for example, for the treatment or prevention of vision disorders and/or for use during ophthalmological procedures for the prevention and/or treatment of ophthalmic disorders. The flowing list of examples is not intended to be limiting.

An ophthalmic agent may be integrated into a fluid, which may flow from a container to an eye through an outlet of a compressible bottle. In some embodiments, the fluid may comprise a solution, emulsion, or suspension comprising an ophthalmic agent. The solution, emulsion, or suspension may comprise the ophthalmic agent. Example ophthalmic agents which may be used in conjunction with a compressible bottle include but are not limited to: timolol, dorzolamide, dexamethasone phosphate, dexamethasone, Betimol, olopatadine, brimonidine, tetrahydrozoline, latanoprostene bunod, latanoprost, bimatoprost, travoprost and combinations of any two or more thereof. Ophthalmic agents may comprise brand name drugs and formulations including, but not limited to, Timoptic, Xalatan, Combigan, Lumigan, Pataday, Pazeo, Trusopt, Cosopt, Alphagan, Visine, Vyzulta, Vesneo, and other agents described herein such as in the following tables. The ophthalmic agents may be dissolved in aqueous solution. The solution may be sterilized and buffered to appropriate pH. In some embodiments, the solution may comprise inactive ingredients such as sodium chloride, sodium citrate, hydroxyethyl cellulose, sodium phosphate, citric acid, sodium dihydrogen phosphate, polyoxyl 40 hydrogenated castor oil, tromethamine, boric acid, mannitol, glycerine edetate disodium, sodium hydroxide, and/or hydrochloric acid. In some embodiments, the fluid comprises a preservative in addition to an ophthalmic agent. Example preservatives include but are not limited to: benzalkonium chloride (BAK), alcohols, parabens, methyl paraben, polyparaben, EDTA, chlorhexidine, quaternary ammonium compounds, Purite®, stabilized oxychloro complexes, Sofzia®, sorbic acid, Sodium perborate, polyquaternium-1, chlorobutanol, cetrimonium chloride, edetate disodium, etc.

In some embodiments the ophthalmic agent is latanoprost. In some embodiments the ophthalmic agent is bimatoprost. In some embodiments the ophthalmic agent is travoprost. In some embodiments the ophthalmic agent is latanoprost and the preservative is benzalkonium chloride (BAK). In some embodiments the ophthalmic agent is bimatoprost and the preservative is benzalkonium chloride (BAK). In some embodiments the ophthalmic agent is travoprost and the preservative is benzalkonium chloride (BAK).

Ophthalmic agents for the treatment of, for example, dry eye, bacterial infection, glaucoma, hypertension, inflammation, allergic conjunctivitis, hypotrichosis of the eyelashes, fungal infection, etc. and ophthalmic agents used for local anesthetic, pupil dilation, etc. may be administered to a patient as a solution, emulsion, or suspension delivered to an eye topically via a compressible bottle, a dropper bottle, or similar delivery mechanism. The solution, emulsion, or suspension may be subject to contamination such as microbial, fungal, or particulate contamination, which may be averse to patient health. In order to prevent such contamination a preservative may be added to the solution, emulsion, or suspension; however, patient exposure to preservatives may have adverse effects to eye health. It may be advantageous to limit patient exposure to preservative by providing a preservative removing device which may remove a preservative from the solution, emulsion, or suspension.

In some embodiments, the ophthalmic agent to be dispensed comprises an active ingredient selected from cyclosporine and lifitegrast. In such embodiments, the ophthalmic agent may be an active ingredient in the treatment of dry eye.

In some embodiments, the ophthalmic agent to be dispensed comprises an active ingredient selected from sulfacetamide sodium, ofloxacin, gatifloxacin, ciprofloxacin, moxifloxacin, tobramycin, levofloxacin, prednisolone acetate, polymyxin B sulfate, and trimethoprim. In some embodiments, the ophthalmological formulation to be dispensed comprises the active ingredients sulfacetamide sodium and prednisolone acetate. In some embodiments, the ophthalmological formulation to be dispensed comprises the active ingredients polymyxin B sulfate and trimethoprim. In such embodiments, the ophthalmic agent may be an active ingredient in the treatment of a bacterial infection.

In some embodiments, the ophthalmic agent to be dispensed comprises an active ingredient selected from brimonidine tartrate, bimatoprost, levobunolol hydrochloride, brinzolamide, betaxolol hydrochloride, pilocarpine hydrochloride, apraclonidine, travoprost, timolol maleate, latanoprost, dorzolamide hydrochloride, timolol maleate, and tafluprost. In some embodiments, the ophthalmological formulation to be dispensed comprises the active ingredients brimonidine tartrate and timolol maleate. In some embodiments, the ophthalmological formulation to be dispensed comprises the active ingredients brinzolamide and brimonidine tartrate. In such embodiments, the ophthalmic agent may be an active ingredient in the treatment of glaucoma or hypertension.

In some embodiments, the ophthalmic agent to be dispensed comprises an active ingredient selected from ketorolac tromethamine, fluorometholone, prednisolone acetate, difluprednate, fluorometholone acetate, nepafenac, dexamethasone, diclofenac sodium, bromfenac, gentamicin, tobramycin, neomycin, and polymyxin B sulfate. In some embodiments, the ophthalmological formulation to be dispensed comprises the active ingredients gentamicin and prednisolone acetate. In some embodiments, the ophthalmological formulation to be dispensed comprises the active ingredients tobramycin and dexamethasone. In some embodiments, the ophthalmological formulation to be dispensed comprises the active ingredients neomycin, polymyxin B sulfate and dexamethasone. In such an embodiment, the ophthalmic agent may be an active ingredient in the treatment of inflammation.

In some embodiments, the ophthalmic agent to be dispensed comprises an active ingredient selected from nedocromil sodium, epinastine HCl, alcaftadine, lodoxamide tromethamine, emedastine difumarate, and olopatadine hydrochloride. In such embodiments, the ophthalmic agent may be an active ingredient in the treatment of allergic conjunctivitis.

In some embodiments, the ophthalmic agent to be dispensed comprises an active ingredient selected from proparacaine hydrochloride and tetracaine hydrochloride. In such embodiments, the ophthalmic agent may be a local anesthetic.

In some embodiments, the ophthalmic agent to be dispensed comprises an active ingredient selected from cyclopentolate hydrochloride, atropine sulfate, and tropicamide. In some embodiments, the ophthalmological formulation to be dispensed comprises the active ingredients cyclopentolate hydrochloride and phenylephrine hydrochloride. In such embodiments, the ophthalmic agent may dilate pupils.

In some embodiments, the ophthalmic agent to be dispensed comprises the active ingredient natamycin. In such embodiments, the ophthalmic agent may be an active ingredient in the treatment of fungal infection.

In some embodiments, the ophthalmic agent to be dispensed comprises an active ingredient selected from lipoic acid choline ester chloride, rebamipide, pilocarpine, ketorolac, aceclidine, tropicamide, sodium hyaluronate, diclofenac sodium, pilocarpine HCl, and ketorolac. In some embodiments, the ophthalmological formulation to be dispensed comprises the active ingredients aceclidine and tropicamide. In some embodiments, the ophthalmological formulation to be dispensed comprises the active ingredients sodium hyaluronate and diclofenac sodium and pilocarpine HCl. In some embodiments, the ophthalmological formulation to be dispensed comprises the active ingredients pilocarpine and ketorolac. In such embodiments, the ophthalmic agent may be an active ingredient in the treatment of presbyopia.

In some embodiments, solutions, emulsions, or suspensions of the disclosure comprise a compound or salt of any ophthalmic agent of the present disclosure, wherein the compound or salt of the ophthalmic agent is largely free of impurities, such as at least about 80 percent by weight (wt %) pure, at least about 81% pure, at least about 82% pure, at least about 83% pure, at least about 84% pure, at least about 85% pure, at least about 86% pure, at least about 87% pure, at least about 88% pure, at least about 89% pure, at least about 90% pure, at least about 91% pure, at least about 92% pure, at least about 93% pure, at least about 94% pure, at least about 95% pure, at least about 96% pure, at least about 97% pure, at least about 98% pure, at least about 99% pure, at least about 99.1% pure, at least about 99.2% pure, at least about 99.3% pure, at least about 99.4% pure, at least about 99.5% pure, at least about 99.6% pure, at least about 99.7% pure, at least about 99.8% pure, or at least about 99.9% pure.

In some embodiments, solutions, emulsions, or suspensions of the disclosure comprise a compound or salt of any ophthalmic agent of the present disclosure, wherein the ophthalmic agent is about 70% to about 99.99%, about 80% to about 99.9%, about 85% to about 99%, about 90% to about 99%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

The amount of the compound or salt of the ophthalmic agent in a solution, emulation, or suspension of the present disclosure can be measured as a percentage of mass per volume. In some embodiments, a solution, emulsion, or suspension such as an aqueous solution of the disclosure, comprises from about 0.05 wt % to about 10 wt % of the compound or salt of any of the ophthalmic agents disclosed herein. In some embodiments, a solution, emulsion, or suspension such as an aqueous solution of the disclosure, comprises about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4 wt %, about 4.1 wt %, about 4.2 wt %, about 4.3 wt %, about 4.4 wt %, about 4.5 wt %, about 5 wt %, about 6 wt %, about 7 wt %, about 8 wt %, about 9 wt %, or about 10 wt % of a compound or salt of the ophthalmic agent described herein.

A compound or salt of the ophthalmic agent described herein can be present in a solution, emulsion, or suspension of the present disclosure at a concentration of, for example, about 500 nanoMolar (nM), about 600 nM, about 700 nM, about 800 nM, about 900 nM, about 1 micromolar (μM), about 2 μM, about 3 μM, about 4 μM, about 5 μM, about 6 μM, about 7 μM, about 8 μM, about 9 μM, about 10 μM about 20 μM, about 30 μM, about 40 μM, about 50 μM, about 60 μM, about 70 μM, about 80 μM, about 90 μM, about 100 μM, about 150 μM, about 200 μM, about 250 μM, about 300 μM, about 350 μM, about 400 μM, about 450 μM, about 500 μM, about 550 μM, about 600 μM, about 650 μM, about 700 μM, about 750 μM, about 800 μM, about 850 μM, about 900 μM, about 1 millimolar (mM), about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of an ophthalmic agent described herein may be present in a solution, emulsion, or suspension within a range of concentrations, the range being defined by an upper and lower value selected from any of the preceding concentrations. For example, the compound or salt of an ophthalmic agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Preservative

The present disclosure provides formulations comprising one or more preservatives for solutions, emulsions, or suspensions of ophthalmic agents of the present disclosure. Preservatives may comprise compounds and salts, for use as preservatives for solutions, emulsions, or suspensions of ophthalmic agents. The one or more preservatives may for example prevent microbial and/or fungal growth. The one or more preservatives may for example prevent physical or chemical deterioration of an ophthalmic agent.

Non-limiting examples of preservative agents include benzalkonium chloride, ethylenediaminetetraacetic acid (EDTA), chlorobutanol, phenylmercuric acetate, phenylmercuric nitrate, chlorhexidine acetate, thimerosal, benzethonium chloride, sorbic acid, alcohols, parabens (e.g., methylparaben, polyparaben), chlorhexidine, quaternary ammonium compounds, cetrimonium bromide, cetramide, cetyltrimethylammonium bromide, hexadecyltrimethylammonium bromide polyquaternium-1 (Polyquad®), stabilized oxychloro complexes (Purite®), solutions of borate, sorbitol, propylene glycol, and zinc (Sofzia®), sodium perborate (GenAqua®), cetrimonium chloride, edetate disodium, etc. In some embodiments, a formulation of the disclosure comprises the preservative of quaternary ammonium compounds. In some embodiments the preservative is benzalkonium chloride (BAK).

In some embodiments, the particulate plug may further include a preservative removing compound or a preservative deactivating compound. Preservative removing or deactivating compounds can decrease toxicity of a formulation to be delivered through typical separation methods including, but not limited to, adsorption, ion exchange, chemical precipitation, or solvent extraction. Preservative removing or deactivating compounds can include, but are not limited to, activated charcoal, antioxidants, ethylenediaminetetraacetic acid (EDTA), anionic hydrogels, cationic compounds, neutralizing agents, or combinations thereof.

The Purite® preservative system includes Stabilized Oxychloro Complex (SOC), a combination of chlorine dioxide, chlorite, and chlorate. When exposed to light, SOC dissociates into water, oxygen, sodium, and chlorine free radicals which cause oxidation of intracellular lipids and glutathione, interrupting vital enzymes for cell function and maintenance. For preservatives such as Purite® which produce chlorine free radicals, the particulate plug of the disclosure can include a material that has a high affinity for free radicals such as activated charcoal or antioxidants such as vitamin E.

The SofZia® preservative system in Travatan Z (Alcon Laboratories, Fort Worth, Tex.) contains borate, sorbitol, propylene glycol, and zinc. Without intending to be bound by theory, it is believed that the preservative effect is from a combination of borate and zinc. For preservatives including borate and zinc, such as SofZia®, the particulate plug of the disclosure can include a metal chelating agent such as EDTA, anionic hydrogels that can extract cationic zinc through electrostatic interactions, cationic hydrogels or resins that can extract anionic borate ions through electrostatic interactions, or a neutralizing agent that can neutralize boric acid.

In some embodiments, solutions, emulsions, or suspensions of the disclosure comprise a compound or salt of any preservative of the present disclosure, wherein the compound or salt of the preservative is largely free of impurities, such as at least about 80% pure, at least about 81% pure, at least about 82% pure, at least about 83% pure, at least about 84% pure, at least about 85% pure, at least about 86% pure, at least about 87% pure, at least about 88% pure, at least about 89% pure, at least about 90% pure, at least about 91% pure, at least about 92% pure, at least about 93% pure, at least about 94% pure, at least about 95% pure, at least about 96% pure, at least about 97% pure, at least about 98% pure, at least about 99% pure, at least about 99.1% pure, at least about 99.2% pure, at least about 99.3% pure, at least about 99.4% pure, at least about 99.5% pure, at least about 99.6% pure, at least about 99.7% pure, at least about 99.8% pure, or at least about 99.9% pure.

In some embodiments, solutions, emulsions, or suspensions of the disclosure comprise a compound or salt of any preservative of the present disclosure, wherein the preservative is about 70% to about 99.99%, about 80% to about 99.9%, about 85% to about 99%, about 90% to about 99.9%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

The amount of the compound or salt of the preservative in a solution, emulation, or suspension of the present disclosure can be measured as a percentage of mass per volume. In some embodiments, a solution, emulsion, or suspension such as an aqueous solution of the disclosure, comprises from about 0.05 wt % to about 10 wt % of the compound or salt of any of the preservatives disclosed herein. In some embodiments, a solution, emulsion, or suspension such as an aqueous solution of the disclosure, comprises about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4 wt %, about 4.1 wt %, about 4.2 wt %, about 4.3 wt %, about 4.4 wt %, about 4.5 wt %, about 5 wt %, about 6 wt %, about 7 wt %, about 8 wt %, about 9 wt %, or about 10 wt % of a compound or salt of the preservative described herein.

A compound or salt of the preservative described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a preservative described herein may be present in a solution, emulsion, or suspension within a range of concentrations, the range being defined by an upper and lower value selected from any of the preceding concentrations. For example, the compound or salt of an preservative of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Complexing Agent

In some embodiments, solutions, emulsions, or suspensions of the present disclosure further comprise a complexing agent. In some embodiments, the compound or salt of an ophthalmic agent of the disclosure exhibits high affinity for the matrix material and the addition of a complexing agent reduces the affinity of the ophthalmic agent for the matrix material. In some embodiments, the solution, emulsion, or suspension comprises a cyclodextrin, a linoleic acid, a lipid mixture, an oleic acid, a cholesterol, an arachidonic acid, a cod liver oil, fatty acid, etc. In some embodiments, the solution, emulsion, or suspension is an aqueous solution comprising a complexing agent. In some embodiments, a solution, emulsion, or suspension for topical administration to the eye comprises a complexing agent.

In some embodiments, the ophthalmic agent is hydrophobic. In some embodiments, a polymer matrix material designed to absorb a preservative such as Benzalkonium chloride (BAK) may also absorb a hydrophobic ophthalmic agent. A complexing agent may decrease the affinity of the ophthalmic agent for the matrix material. The matrix material may selectively remove a preservative from the solution, emulsion, or suspension. A complexing agent may be used to tune the interaction between the ophthalmic agent and the matrix. Utilizing a complexing agent, such as cyclodextrin, may change the relative hydrophobicity (hydrophilicity) of the ophthalmic agent relative to the polymer matrix material, thereby decreasing the affinity of the ophthalmic agent for the matrix. Utilizing a complexing agent may keep the ophthalmic agent soluble in the water phase such that it may not be absorbed on or in the polymer matrix material.

As a secondary effect, the capping agent (also called the complexing agent) may increase the solubility of the ophthalmic agent. Due to the relatively low concentrations of ophthalmic agents used herein, solubility may typically not be a concern even if a complexing agent is not used. As an additional secondary effect, the capping agent may increase the stability of a solution comprising the ophthalmic agent and the preservative. As an additional secondary effect, the capping agent may improve the delivery of the ophthalmic agent to certain areas of the body.

In some embodiments, the complexing agent (or capping agent) forms a guest-host complex with the ophthalmic agent. The complexing agent may have a hydrophobic interior and a hydrophilic exterior. In some embodiments, the complexing agent is a cyclodextrin. In some embodiments, the complexing agent is a crown ether. In some embodiments, the complexing agent is a zeolite.

In some embodiments, the complexing agent is a cyclodextrin. A cyclodextrin may comprise glucopyranose sub units. A cyclodextrin may comprise 6, 7, 8, or more glucopyranose units. A cyclodextrin which comprises 6 glucopyranose units may be an alpha cyclodextrin. A cyclodextrin which comprises 7 glucopyranose units may be a beta cyclodextrin. A cyclodextrin which comprises 8 glucopyranose units may be a gamma cyclodextrin. A cyclodextrin may be toroidal in shape with the C2- and C3-hydroxyls forming the larger opening and the C6-hydroxyls forming the smaller opening. The interior of the torus may be hydrophobic. The size of the hydrophobic cavity within the cyclodextrin may be a function of the number of glucopyranose units.

Typical cyclodextrins are constituted by 6-8 glucopyranoside units. These subunits are linked by 1,4 glycosidic bonds. The cyclodextrins have toroidal shapes, with the larger and the smaller openings of the toroid exposing to the solvent secondary and primary hydroxyl groups respectively. Because of this arrangement, the interior of the toroids is not highly hydrophobic, but considerably less hydrophilic than the aqueous environment and thus able to host other hydrophobic molecules. In contrast, the exterior is sufficiently hydrophilic to impart cyclodextrins (or their complexes) water solubility. In some embodiments, the cyclodextrin may be modified by chemical substitution of the hydroxyl groups of the glucopyranose units. Each glucopyranose unit has 3 hydroxyl groups that are available to be reacted and substituted with. In some embodiments multiple of these hydroxyls can be reacted, which is described as degree of substitution. The degree of substitution (DS) describes the number of hydroxyls (on average) that have been reacted. Hydropropoxidation is an example of this type of substitution reaction to create so called hydroxypropyl cyclodextrins of various DS depending how many of the hydroxy groups are reacted. In some embodiments, the cyclodextrin may be (2-hydroxypropyl)-β-cyclodextrin. The cyclodextrin may be (2-hydroxypropyl)-α-cyclodextrin, (2-hydroxypropyl)-γ-cyclodextrin, α-cyclodextrin, β-cyclodextrin, γ-cyclodextrin, methyl-α-cyclodextrin, methyl-β-cyclodextrin, methyl-γ-cyclodextrin, or another substituted cyclic glucose polymer. In other embodiments, the cyclodextrin is chosen from dimethyl-beta-cyclodextrin, highly sulphated-beta-cyclodextrin, 6-monodeoxy-6-N-mono(3-hydroxy)propylamino-beta-cyclodextrin. In other embodiments, the cyclodextrin is a randomly or selectively substituted at the hydroxyls with any chemistry and to any required degree for alpha, beta or gamma or any ring size cyclodextrin. In other embodiments other types of and degrees of substitution on the cyclodextrin rings are also known and possible. Any of these can used as complexing agents. In some embodiments commercial products are possible such as CAVASOL® W7 HP PHARMA is pharmaceutical grade hydroxypropyl-beta-cyclodextrin from Wacker Chemie AG. CAVASOL® W7 HP PHARMA is a highly soluble beta-cyclodextrin derivative. Hydroxypropyl Betadex is another example of this same commercial type cyclodextrin.

In some embodiments, the solution, emulsion, or suspension may comprise the cyclodextrin at a 5000% molar excess over the ophthalmic agent (e.g. a 50 to 1 ratio of cyclodextrin to the ophthalmic agent). The solution, emulsion, or suspension may comprise the cyclodextrin at a greater concentration than the ophthalmic agent. The solution, emulsion, or suspension may comprise the cyclodextrin at a molar excess of greater than 100%, greater than 500%, greater than 1000%, greater than 2000%, greater than 5000%, greater than 10000 or more. The concentration of cyclodextrin may be greater than the ophthalmic agent by a factor of more than 10, by a factor of more than 20, or more.

The molar ratio of a complexing agent of the present disclosure to an ophthalmic agent in a solution, emulsion, or suspension of the present disclosure can be about 200:about 1, about 175:about 1, about 150:about 1, about 125:about 1, about 100:about 1, about 75:about 1, about 65:about 1, about 60:about 1, about 55 about 1, about 50:about 1, about 45:about 1, about 40:about 1, about 30 about 1, about 25:about 1, about 10:about 1, about 9.5:about 1, about 9.0:about 1, about 8.5:about 1, about 8.0:about 1, about 7.5:about 1, about 7.0:about 1, about 6.5:about 1, about 6.0:about 1, about 5.5:about 1, about 5.0:about 1, about 4.5:about 1, about 4.0:about 1, about 3.5:about 1, about 3.0:about 1, about 2.5:about 1, about 2.0:about 1, about 1.9:about 1, about 1.8:about 1, about 1.7:about 1, about 1.6:about 1, about 1.5:about 1, about 1.4:about 1, about 1.3:about 1, about 1.2:about 1, about 1.19:about 1, about 1.18:about 1, about 1.17:about 1, about 1.16:about 1, about 1.15:about 1, about 1.14:about 1, about 1.13:about 1, about 1.12:about 1, about 1.11:about 1. The ratio of a complexing agent to an ophthalmic agent in a solution, emulsion, or suspension of the present disclosure can be within the range of between about 100:about 1 and about 10 to about 1, between about 80:about 1 and about 10:about 1, between about 100:about 1 and about 20:about 1.

In some embodiments, the solution, emulsion, or suspension may comprise the cyclodextrin at a concentration of 127 µM (micromolar). In some embodiments, the solution, emulsion, or suspension may comprise the cyclodextrin at a concentration of greater than 1 µM, 2 µM, 5 µM, 10 µM, 20 µM, 50 µM, 100 µM, or more. In some embodiments, the solution, emulsion, or suspension may comprise the cyclodextrin at a concentration of less than 500 µM, or it may be at a concentration of about 1 mM (millimolar), 2 mM, 5 mM, 10 mM, 20 mM, 50 mM, 100 mM, or less.

In some embodiments, the complexing agent may comprise a mixture of cyclodextrins comprising one or more cyclodextrins disclosed elsewhere herein.

In some embodiments, the complexing agent may comprise a micelle forming compound. In some embodiments, the complexing agent may comprise a surfactant. The complexing agent may generally comprise an amphiphilic compound. The micelle forming compound may comprise a hydrophilic head group and a hydrophobic tail. The hydrophilic head group may form an exterior surface of the micelle with the hydrophobic tail forming an interior surface of the micelle. The hydrophobic drug may be located inside of the micelle.

The complexing agent may comprise one or more of a linoleic acid, a lipid mixture, an oleic acid, cholesterol, an arachidonic acid, cod liver oil, a fatty acid, etc. In some embodiments a fatty acid may include caprylic acid, capric acid, lauric acid, myristic acid, palmitic acid, stearic acid, arachidic acid, behenic acid, lignoceric acid, or cerotic acid Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid or the like.

In some embodiments, a preservative of the present disclosure may be a surfactant. For example, preservatives comprising quaternary ammonium compounds may be surfactants. Purite may be a surfactant. Cetrimide may be a surfactant. In some embodiments, benzalkonium chloride may be a cationic surfactant. Benzalkonium chloride may form micelles. The addition of benzalkonium chloride may stabilize and/or increase the solubility of hydrophobic ophthalmic agents in solution, e.g. latanoprost, bimatoprost, travoprost, etc. Accordingly, hydrophobic ophthalmic agents may be sufficiently solubilized and/or stabilized in formulation comprising benzalkonium chloride. Formulations of hydrophobic ophthalmic agents comprising cyclodextrin may comprise ratios of about 1:1 (agent to cyclodextrin) or may not comprise cyclodextrin at all, as a hydrophobic ophthalmic agent may be sufficiently solubilized without cyclodextrin. For example, marketed ophthalmic formulations of latanoprost may not comprise cyclodextrin as a solubilizing agent.

Without being limited by theory, removal of benzalkonium chloride by the preservative removing device may reduce solubility of a hydrophobic ophthalmic agent in a formulation. In such cases, an amount of a hydrophobic agent, e.g. latanoprost, bimatoprost, travoprost, etc., which may pass through the preservative removing device may be reduced, which may reduce a concentration of the ophthalmic agent in a dose. The addition of a cyclodextrin of the present disclosure may decrease interaction between the hydrophobic agent and a matrix material of the present disclosure. The addition of a cyclodextrin of the present disclosure may maintain solubility of the hydrophobic agent in the formulation as it passes through a matrix material of the present disclosure.

In some embodiments, solutions, emulsions, or suspensions of the disclosure comprise a compound or salt of any complexing agent of the present disclosure, wherein the compound or salt of the complexing agent is largely free of impurities, such as at least about 80 wt % pure, at least about 81% pure, at least about 82% pure, at least about 83% pure, at least about 84% pure, at least about 85% pure, at least about 86% pure, at least about 87% pure, at least about 88% pure, at least about 89% pure, at least about 90% pure, at least about 91% pure, at least about 92% pure, at least about 93% pure, at least about 94% pure, at least about 95% pure, at least about 96% pure, at least about 97% pure, at least about 98% pure, at least about 99% pure, at least about 99.1% pure, at least about 99.2% pure, at least about 99.3% pure, at least about 99.4% pure, at least about 99.5% pure, at least about 99.6% pure, at least about 99.7% pure, at least about 99.8% pure, or at least about 99.9% pure.

In some embodiments, solutions, emulsions, or suspensions of the disclosure comprise a compound or salt of any complexing agent of the present disclosure, wherein the complexing agent is about 70% to about 99.99%, about 80% to about 99.9%, about 85% to about 99%, about 90% to about 99%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

The amount of the compound or salt of the complexing agent in a solution, emulation, or suspension of the present disclosure can be measured as a percentage of mass per volume. In some embodiments, a solution, emulsion, or suspension such as an aqueous solution of the disclosure, comprises from about 0.05 wt % to about 10 wt % of the compound or salt of any of the complexing agents disclosed herein. In some embodiments, a solution, emulsion, or suspension such as an aqueous solution of the disclosure, comprises about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4 wt %, about 4.1 wt %, about 4.2 wt %, about 4.3 wt %, about 4.4 wt %, about 4.5 wt %, about 5 wt %, about 6 wt %, about 7 wt %, about 8 wt %, about 9 wt %, or about 10 wt % of a compound or salt of the complexing agent described herein.

A compound or salt of the complexing agent described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400

μM, about 450 μM, about 500 μM, about 550 μM, about 600 μM, about 650 μM, about 700 μM, about 750 μM, about 800 μM, about 850 μM, about 900 μM M, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a complexing agent described herein may be present in a solution, emulsion, or suspension within a range of concentrations, the range being defined by an upper and lower value selected from any of the preceding concentrations. For example, the compound or salt of a complexing agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

Excipients

Devices and methods of the present disclosure may comprise formulating the solution, emulsion, or suspension with one or more inert, pharmaceutically-acceptable excipients. Liquid compositions include, for example, solutions in which a compound is dissolved, emulsions comprising a compound, or a solution containing liposomes or micelles comprising an ophthalmic agent as disclosed herein. These compositions can also contain minor amounts of nontoxic, auxiliary substances, such as wetting or emulsifying agents, pH buffering agents, tonicity agents and other pharmaceutically-acceptable additives.

In some embodiments, solutions, emulsions, or suspensions of the present disclosure further comprise one or more physiologically acceptable carriers including excipients and auxiliaries which facilitate processing of the pharmaceutical agent into preparations which are used pharmaceutically. Proper formulation is dependent upon the route of administration chosen.

Pharmaceutically acceptable carriers include, for example, aqueous solutions such as water or physiologically buffered saline or other solvents or vehicles such as glycols, glycerol, oils such as olive oil, or organic esters. The excipients can be chosen, for example, to effect delayed release of an agent or to selectively target one or more cells, tissues, or organs. The composition can also be present in a solution suitable for topical administration, such as an eye drop.

Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, hydroxypropyl methylcellulose, hypromellose, Methocel, methyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In some embodiments, the solutions, emulsions, or suspensions of the disclosure may include one or more additional excipients. The amount of the excipient in a pharmaceutical formulation of the disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of the compound in the solution, emulsion, or suspension. The amount of the excipient in a solution, emulsion, or suspension of the disclosure can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass of the compound in the solution, emulsion, or suspension.

The amount of the excipient in a solution, emulsion, or suspension of the present disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form. The amount of the excipient in a solution, emulsion, or suspension can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass or by volume of the unit dosage form.

The ratio of a compound of an ophthalmic agent of the present disclosure to an excipient in a pharmaceutical formulation of the present disclosure can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The ratio of a compound of an ophthalmic agent to an excipient in a solution, emulsion, or suspension of the present disclosure can be within the range of between about 100:about 1 and about 1 to about 10, between about 10:about 1 and about 1:about 1, between about 5:about 1 and about 2:about 1.

In some embodiments, a solution, emulsion, or suspension of the present disclosure comprises an agent for adjusting the pH of the formulation. In some embodiments, the agent for adjusting the pH could be an acid, e.g., hydrochloric acid or boric acid, or a base, e.g., sodium hydroxide or potassium hydroxide. In some embodiments, the agent for adjusting the pH is an acid such as boric acid. The formulation may comprise about 0.05 wt % to about 5 wt %, about 0.1% to about 4%, about 0.1% to about 3 wt %, about 0.1 wt % to about 2 wt %, or about 0.1 wt % to about 1 wt % of an agent for adjusting the pH.

Solutions, emulsions, or suspensions of the disclosure can be formulated at any suitable pH. In some embodiments, the pH of the solution emulsion or suspension is about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9 pH units. In some embodiments, the pH of the solution, emulsion, or suspension is from about 4 to about 10, about 4.75 to about 7.40, about 5 to about 9, about 6 to about 8, about 6.5 to about 8, about 7 to about 8, about 7.2 to about 8, about 7.2 to about 7.8, about 7.3 to about 7.5, or about 7.35 to about 7.45. In some embodiments the pH of the solution, emulsion, or suspension is about 7.4.

In some embodiments, the addition of an excipient to a pharmaceutical formulation of the present disclosure can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the addition of an excipient to a pharmaceutical formulation of the present disclosure can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the viscosity change falls within can be created by combining any two of the preceding percentages. For example, the addition of an excipient can increase or decrease the viscosity of the composition by 5% to 99%, by 10% to 95%, by 20% to 70% or by 35% to 55%.

In some embodiments, an excipient that increases a viscosity may comprise polyvinyl alcohol, poloxamers, hyaluronic acid, carbomers, and polysaccharides, that is, cellulose derivatives, hydroxymethyl cellulose, hypromellose, Methacel, gellan gum, and xanthan gum. In some embodiments, an excipient that increases mucoadhesive properties may be added. Excipients that increase mucoadhesion may include polyacrylic acid, hyaluronic acid, sodium carboxymethyl cellulose, lectins, and chitosan.

In some embodiments, solutions, emulsions, or suspensions of the present disclosure further comprise an agent for adjusting the osmolarity of the solution, emulsion, or suspension, e.g., mannitol, sodium chloride, sodium sulfate, dextrose, potassium chloride, glycerin, propylene glycol, calcium chloride, and magnesium chloride. In some embodiments, the solution, emulsion, or suspension comprises from about 0.1 wt % to about 10 wt %, about 0.5 wt % to about 8 wt %, about 1 wt % to about 5 wt %, about 1 wt % to about 4 wt %, or about 1 wt % to about 3 wt % of an agent for adjusting the osmolarity of the solution, emulsion, or suspension. In some embodiments, the solution, emulsion, or suspension of the disclosure has an osmolarity from about 10 milliOsomols (mOsm) to about 1000 mOsm, about 100 mOsm to about 700 mOsm, about 200 mOsm to about 400 mOsm, about 250 mOsm to about 350 mOsm or about 290 mOsm to about 310 mOsm.

In some embodiments, solutions, emulsions, or suspensions of the present disclosure further comprise a buffering agent, such as tromethamine, potassium phosphate, sodium phosphate, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino)propanesulfonic acid buffer (MOPS), and piperazine-N,N'-bis(2-ethanesulfonic acid) buffer (PIPES), sodium acetate-boric acid stock solution, boric acid-sodium carbonate with sodium chloride solution, boric acid-sodium borate buffer, sodium and potassium phosphate buffers, boric acid-sodium carbonate with potassium chloride, or combinations thereof. In some embodiments, the solution, emulsion, or suspension comprises from about 0.05 wt % to about 5 wt %, about 0.1 wt % to about 4 wt %, about 0.1 wt % to about 3 wt %, about 0.1 wt % to about 2 wt %, or about 0.1 wt % to about 1 wt % of an agent for buffering the solution, emulsion, or suspension.

In some embodiments, the solution emulsion or suspension provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Salts

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The compounds may be synthesized using conventional techniques. Advantageously, these compounds are conveniently synthesized from readily available starting materials. Synthetic chemistry transformations and methodologies useful in synthesizing the compounds described herein are known in the art.

The present disclosure provides salts of any one or both of an ophthalmic agent and a preservative. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is an ammonium salt, a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrazole, pipyrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrazole salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucuronic acid, saccharic acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

The methods and formulations described herein include the use of amorphous forms as well as crystalline forms (also known as polymorphs). Active metabolites of compounds or salts of any one of the compounds of the present disclosure having the same type of activity are included in the scope of the present disclosure. In addition, the compounds described herein can exist in unsolvated as well as solvated forms with pharmaceutically acceptable solvents such as water, ethanol, and the like. The solvated forms of the compounds and salts presented herein are also considered to be disclosed herein.

In some embodiments, an aqueous solutions, emulsions, or suspensions of the disclosure comprises at least 90 wt % water, such as at least 91 wt %, at least 92 wt %, at least 93 wt %, at least 94 wt %, at least 95 wt %, at least 96 wt %, at least 97 wt %, at least 98 wt %, or even at least 99 wt % of water.

Dosage

The dosage and frequency (single or multiple doses) administered to a mammal may vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents may be used in conjunction with the methods and compounds of this disclosure. Adjustment and manipulation of established dosages (e.g., frequency and duration) are well within the ability of those skilled in the art.

Dosages may be varied depending upon the requirements of the patient and the compound being employed. The dose administered to a patient, in the context of the present disclosure should be sufficient to affect a beneficial therapeutic response in the patient over time. The size of the dose also may be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals may be adjusted individually to provide levels of the administered compound effective for the particular clinical indication being treated. This may provide a therapeutic regimen that is commensurate with the severity of the individual's disease state While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A flow control device for delivering an ophthalmic formulation, the device comprising: a reservoir, the reservoir comprising the ophthalmic formulation disposed therein, the ophthalmic formulation comprising an ophthalmic agent and a preservative; a nozzle, the nozzle comprising: an outlet, an interior volume comprising a preservative removing device, and one or more nozzle apertures fluidically connecting the interior volume with an exterior of the nozzle; a reservoir interface positioned between the reservoir and the nozzle, the reservoir interface comprising one or more reservoir apertures fluidically connecting an interior of the reservoir with an exterior of the reservoir, wherein upon rotation or translation of the nozzle relative to the reservoir interface, the one or more nozzle apertures are fluidically connected or disconnected from the one or more reservoir apertures; and a spring disposed between the reservoir interface and the nozzle such that the spring provides a restoring force opposing a compressing motion by the nozzle upon rotation or translation of the nozzle relative to the reservoir interface;

a bottle cap, wherein the one or more nozzle apertures are fluidically connected with the one or more reservoir apertures when the bottle cap is removed and wherein the one or more nozzle apertures are fluidically disconnected with the one or more reservoir apertures when the bottle cap is coupled to the nozzle.

2. The flow control device of claim 1, wherein the preservative removing device comprises a polymeric matrix comprising absorbed molecules of the preservative from the ophthalmic formulation.

3. The flow control device of claim 2, wherein upon rotation or translation of the nozzle, the one or more nozzle apertures are fluidically connected or disconnected from the one or more reservoir apertures, thereby allowing or preventing flow of the ophthalmic formulation between the interior volume of the nozzle and the reservoir and stabilizing a concentration of the preservative in the ophthalmic formulation disposed within the reservoir.

4. The flow control device of claim 1, further comprising a bottle cap, wherein rotation of the bottle cap relative to the reservoir rotates or translates the nozzle relative to the reservoir.

5. The flow control device of claim 4, wherein the bottle cap produces an audible or tactile click when moved into a closed state.

6. The flow control device of claim 4, wherein the bottle cap comprises a closure assembly which is resistant to manipulation from a child.

7. The flow control device of claim 1, wherein the nozzle comprises an outlet filter adjacent the outlet.

8. The flow control device of claim 7, wherein the outlet filter comprises a mesh or a screen.

9. The flow control device of claim 1, wherein the nozzle comprises an inlet filter adjacent the one or more nozzle apertures.

10. The flow control device of claim 9, wherein the inlet filter comprises a mesh or a screen.

11. The flow control device of claim 1, wherein, when the bottle cap is removed, the nozzle is in an aligned rotational position.

12. The flow control device of claim 11, wherein rotation of the bottle cap about an axis of rotation relative to the reservoir rotates the nozzle about the axis of rotation relative to the reservoir.

13. The flow control device of claim 1, wherein the nozzle comprises one or more alignment features on a bottle-cap facing surface, the one or more alignment features receivable by the bottle cap.

14. The flow control device of claim 13, wherein the bottle cap comprises one or more alignment channels on an interior surface of the bottle cap, the one or more alignment features on the bottle-cap facing surface of the nozzle received within the one or more alignment channels.

15. The flow control device of claim 1, wherein, when the bottle cap is removed, the nozzle is in an aligned translational position.

16. The flow control device of claim 15, wherein the restoring force of the spring translates the nozzle to the aligned translational position when the bottle cap is removed.

17. The flow control device of claim 16, wherein, when the bottle cap is in a closed state, the nozzle is not in the aligned position.

18. The flow control device of claim 17, wherein, when the bottle cap is in a closed state, the spring is at least partially compressed.

19. The flow control device of claim 17, further comprising a translation stop.

20. The flow control device of claim 19, wherein the translation stop comprises a plug configured to seal the one or more nozzle apertures.

21. The flow control device of claim 19, wherein the translation stop comprises a rotation stop for the bottle cap.

22. The flow control device of claim 1, wherein the nozzle comprises a housing configured to contain the preservative removing device, wherein the housing is translated in relation to an exterior surface of the reservoir interface.

23. The flow control device of claim 2, wherein the polymeric matrix comprises at least one monomer selected from the group consisting of hydroxyethyl methacrylate (HEMA), methacrylic acid (MAA), N-vinyl-pyrrolidone (NVP), dimethylacrylamide (DMA), t-butyl methacrylate (TBM), 2-sulfoethyl methacrylate (SEM), acrylamide (AM), and Methacryloxypropyltris(trimethylsiloxy)silane (TRIS).

24. The flow control device of claim 1, wherein the ophthalmic agent comprises at least one of Timolol Maleate, Levofloxacin, Dorzolamide, Brimonidine Tartrate, Bimatoprost, Tetrahydrozolin, Latanoprost, or Olopatadine.

25. The flow control device of claim 1, wherein the preservative comprises at least one of benzalkonium chloride, solutions of borate, sorbitol, propylene glycol, cetrimonium chloride, cetrimonium bromide, or stabilized oxychloro complexes.

26. A method of controlling a preservative concentration within an ophthalmic formulation comprising:

receiving a bottle comprising: a reservoir comprising the ophthalmic formulation disposed therein, the ophthalmic formulation comprising an ophthalmic agent and the preservative;

a nozzle comprising: an outlet, an interior volume comprising a preservative removing device, and one or more nozzle apertures fluidically connecting the interior volume with an exterior of the nozzle;

a reservoir interface positioned between the reservoir and the nozzle, the reservoir interface comprising one or more reservoir apertures fluidically connecting an interior of the reservoir with an exterior of the reservoir, wherein upon rotation or translation of the nozzle relative to the reservoir interface, the one or more nozzle apertures are fluidically connected or disconnected from the one or more reservoir apertures; and a spring disposed between the reservoir interface and the nozzle such that the spring provides a restoring force opposing a compressing motion by the nozzle upon rotation or translation of the nozzle relative to the reservoir interface; and rotating or translating the nozzle relative to the reservoir interface, thereby fluidically connecting or disconnecting the one or more nozzle apertures with the one or more reservoir apertures a bottle cap, wherein the one or more nozzle apertures are fluidically connected with the one or more reservoir apertures when the bottle cap is removed and wherein the one or more nozzle apertures are fluidically disconnected with the one or more reservoir apertures when the bottle cap is coupled to the nozzle.

* * * * *

UNITED STATES PATENT AND TRADEMARK OFFICE
CERTIFICATE OF CORRECTION

| | | |
|---|---|---|
| PATENT NO. | : 11,564,832 B2 | Page 1 of 1 |
| APPLICATION NO. | : 16/833368 | |
| DATED | : January 31, 2023 | |
| INVENTOR(S) | : Howard L. Golub et al. | |

It is certified that error appears in the above-identified patent and that said Letters Patent is hereby corrected as shown below:

In the Claims

Claim 1: Column 51, Line 13-23. Please correct as follows:
disconnected from the one or more reservoir apertures; a spring disposed between the reservoir interface and the nozzle such that the spring provides a restoring force opposing a compressing motion by the nozzle upon rotation or translation of the nozzle relative to the reservoir interface; and
a bottle cap, wherein the one or more nozzle apertures are fluidically connected with the one or more reservoir apertures when the bottle cap is removed and wherein the one or more nozzle apertures are fluidically disconnected with the one or more reservoir apertures when the bottle cap is coupled to the nozzle.

Claim 26: Column 52, Line 63 - Column 53, Line 10. Please correct as follows:
disconnected from the one or more reservoir apertures;
a spring disposed between the reservoir interface and the nozzle such that the spring provides a
    restoring force opposing a compressing motion by the nozzle upon rotation or translation of
    the nozzle relative to the reservoir interface; and a bottle cap, wherein the one or more nozzle
    apertures are fluidically connected with the one or more reservoir apertures when the bottle
    cap is removed and wherein the one or more nozzle apertures are fluidically disconnected
    with the one or more reservoir apertures when the bottle cap is coupled to the nozzle; and
rotating or translating the nozzle relative to the reservoir interface, thereby fluidically connecting or
    disconnecting the one or more nozzle apertures with the one or more reservoir apertures.

Signed and Sealed this
Eleventh Day of April, 2023

*Katherine Kelly Vidal*
Katherine Kelly Vidal
*Director of the United States Patent and Trademark Office*